US009394289B2

(12) United States Patent
Illig et al.

(10) Patent No.: US 9,394,289 B2
(45) Date of Patent: Jul. 19, 2016

(54) INHIBITORS OF C-FMS KINASE

(71) Applicant: Janssen Pharmaceutica NV, Beerse (BE)

(72) Inventors: Carl R. Illig, Phoenixville, PA (US); Shelley K. Ballentine, Lansdale, PA (US); Jinsheng Chen, Exton, PA (US); Renee Louise Desjarlais, Saint Davids, PA (US); Sanath K. Meegalla, Garnet, NJ (US); Mark Wall, Lansdale, PA (US); Kenneth Wilson, Vineland, NJ (US); Bruce E. Tomczuk, Collegeville, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/480,944

(22) Filed: Sep. 9, 2014

(65) Prior Publication Data
US 2014/0378457 A1    Dec. 25, 2014

Related U.S. Application Data

(62) Division of application No. 11/736,644, filed on Apr. 18, 2007, now Pat. No. 8,859,602.

(60) Provisional application No. 60/793,667, filed on Apr. 20, 2006.

(51) Int. Cl.
| C07D 409/12 | (2006.01) |
| C07D 207/34 | (2006.01) |
| C07D 233/90 | (2006.01) |
| C07D 401/12 | (2006.01) |
| C07D 401/14 | (2006.01) |
| C07D 405/12 | (2006.01) |
| C07D 405/14 | (2006.01) |
| C07D 413/12 | (2006.01) |
| C07D 413/14 | (2006.01) |
| C07D 493/08 | (2006.01) |
| C07D 403/12 | (2006.01) |
| C12N 9/99 | (2006.01) |

(52) U.S. Cl.
CPC ............ *C07D 409/12* (2013.01); *C07D 207/34* (2013.01); *C07D 233/90* (2013.01); *C07D 401/12* (2013.01); *C07D 401/14* (2013.01); *C07D 403/12* (2013.01); *C07D 405/12* (2013.01); *C07D 405/14* (2013.01); *C07D 413/12* (2013.01); *C07D 413/14* (2013.01); *C07D 493/08* (2013.01); *C12N 9/99* (2013.01)

(58) Field of Classification Search
CPC .................................................... C07D 409/12
USPC .............................. 548/315.1, 311.1; 514/397
See application file for complete search history.

(56) References Cited

U.S. PATENT DOCUMENTS

| 2,466,420 A | 4/1949 | Hagemeyer et al. |
| 3,226,394 A | 12/1965 | Schipper |
| 4,551,540 A | 11/1985 | Hechenbleikner et al. |
| 5,101,440 A | 3/1992 | Watanabe et al. |
| 5,190,541 A | 3/1993 | Abele et al. |
| 5,474,765 A | 12/1995 | Thorpe |
| 5,534,940 A | 7/1996 | Sato et al. |
| 5,666,164 A | 9/1997 | Kondo et al. |
| 5,762,918 A | 6/1998 | Thorpe |
| 5,855,866 A | 1/1999 | Thorpe et al. |
| 5,874,442 A | 2/1999 | Doll et al. |
| 5,940,132 A | 8/1999 | Kondo et al. |

(Continued)

FOREIGN PATENT DOCUMENTS

| CN | 101017260 | 8/2007 |
| EP | 1566379 A1 | 8/2005 |

(Continued)

OTHER PUBLICATIONS

Guillory (in Brittain ed.), "Polymorphism in Pharmaceutical Solids.," NY: Marcel Dekker, Inc., 1999, 1-2, 125-181, 183-226.*

(Continued)

*Primary Examiner* — Patricia L Morris

(57) ABSTRACT

The invention is directed to compounds of Formula I:

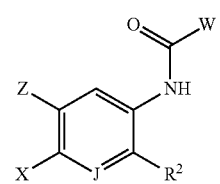

wherein Z, X, J, $R^2$ and W are set forth in the specification, as well as solvates, hydrates, tautomers and pharmaceutically acceptable salts thereof, that inhibit protein tyrosine kinases, especially c-fms kinase. Methods of treating autoimmune diseases; and diseases with an inflammatory component; treating metastasis from ovarian cancer, uterine cancer, breast cancer, prostate cancer, lung cancer, colon cancer, stomach cancer, hairy cell leukemia; and treating pain, including skeletal pain caused by tumor metastasis or osteoarthritis, or visceral, inflammatory, and neurogenic pain; as well as osteoporosis, Paget's disease, and other diseases in which bone resorption mediates morbidity including rheumatoid arthritis, and other forms of inflammatory arthritis, osteoarthritis, prosthesis failure, osteolytic sarcoma, myeloma, and tumor metastasis to bone with the compounds of Formula I, are also provided.

9 Claims, No Drawings

(56) References Cited

U.S. PATENT DOCUMENTS

| | | |
|---|---|---|
| 5,944,718 A | 8/1999 | Austin et al. |
| 5,968,952 A | 10/1999 | Venet et al. |
| 6,037,350 A | 3/2000 | Venet et al. |
| 6,100,254 A | 8/2000 | Budde et al. |
| 6,117,432 A | 9/2000 | Ganne et al. |
| 6,169,096 B1 | 1/2001 | Venet et al. |
| 6,187,786 B1 | 2/2001 | Venet et al. |
| 6,235,746 B1 | 5/2001 | Davis et al. |
| 6,342,219 B1 | 1/2002 | Thorpe et al. |
| 6,346,625 B1 | 2/2002 | Karabelas et al. |
| 6,383,790 B1 | 5/2002 | Shokat |
| 6,420,387 B1 | 7/2002 | Venet et al. |
| 6,458,800 B1 | 10/2002 | Angibaud et al. |
| 6,596,746 B1 | 7/2003 | Das et al. |
| 6,692,491 B1 | 2/2004 | Phan |
| 6,710,781 B1 | 3/2004 | Saito |
| 6,987,119 B2 | 1/2006 | Gaiba et al. |
| 7,039,254 B1 | 5/2006 | Maenaka et al. |
| 7,157,456 B2 | 1/2007 | Straub et al. |
| 7,208,493 B2 | 4/2007 | Wrasidlo et al. |
| 7,427,683 B2 | 9/2008 | Player et al. |
| 7,429,603 B2 | 9/2008 | Player et al. |
| 7,645,755 B2 | 1/2010 | Illig et al. |
| 7,662,837 B2 | 2/2010 | Illig et al. |
| 7,790,724 B2 | 9/2010 | Player et al. |
| 7,795,279 B2 | 9/2010 | Ballentine et al. |
| 7,973,035 B2 | 7/2011 | Illig et al. |
| 8,497,376 B2 * | 7/2013 | Illig et al. ............... 546/112 |
| 2002/0016625 A1 | 2/2002 | Falotico et al. |
| 2002/0019414 A1 | 2/2002 | Altmann et al. |
| 2002/0028028 A1 | 3/2002 | Michel |
| 2002/0119962 A1 | 8/2002 | Jacobs et al. |
| 2003/0130280 A1 | 7/2003 | O'Farrell et al. |
| 2003/0153610 A1 | 8/2003 | Straub et al. |
| 2003/0169247 A1 | 9/2003 | Kawabe et al. |
| 2004/0049032 A1 | 3/2004 | Charrier et al. |
| 2005/0004112 A1 | 1/2005 | Player et al. |
| 2005/0113566 A1 | 5/2005 | Player et al. |
| 2005/0184952 A1 | 8/2005 | Konno et al. |
| 2005/0219188 A1 | 10/2005 | Kawabe et al. |
| 2006/0040995 A1 | 2/2006 | Bacque et al. |
| 2006/0055661 A1 | 3/2006 | Kawaguchi |
| 2006/0100619 A1 | 5/2006 | McClurken et al. |
| 2006/0122181 A1 | 6/2006 | Ikemoto et al. |
| 2006/0132383 A1 | 6/2006 | Galley et al. |
| 2006/0148812 A1 | 7/2006 | Illig et al. |
| 2006/0189623 A1 | 8/2006 | Illig et al. |
| 2006/0258724 A1 | 11/2006 | Straub et al. |
| 2006/0281771 A1 | 12/2006 | Baumann et al. |
| 2006/0281788 A1 | 12/2006 | Baumann et al. |
| 2007/0121039 A1 | 5/2007 | Tago et al. |
| 2007/0179125 A1 | 8/2007 | Fraysse et al. |
| 2007/0182682 A1 | 8/2007 | Hong et al. |
| 2007/0249593 A1 | 10/2007 | Illig et al. |
| 2007/0249608 A1 | 10/2007 | Illig et al. |
| 2007/0249649 A1 | 10/2007 | Illig et al. |
| 2007/0249680 A1 | 10/2007 | Illig et al. |
| 2007/0259869 A1 | 11/2007 | Binch et al. |
| 2008/0051402 A1 | 2/2008 | Illig et al. |
| 2008/0068402 A1 | 3/2008 | Ioka et al. |
| 2008/0100554 A1 | 5/2008 | Mori |
| 2008/0106641 A1 | 5/2008 | Chou |
| 2008/0284719 A1 | 11/2008 | Yoshida |
| 2009/0105296 A1 | 4/2009 | Illig et al. |
| 2009/0197913 A1 | 8/2009 | Baumann et al. |
| 2011/0037785 A1 | 2/2011 | Shiomi |
| 2011/0195960 A1 | 8/2011 | Illig et al. |

FOREIGN PATENT DOCUMENTS

| | | |
|---|---|---|
| EP | 1705636 | 9/2006 |
| EP | 1936600 | 6/2008 |
| GB | 1189719 | 4/1970 |
| JP | 01/346070 | 12/2001 |
| JP | 3243861 | 1/2002 |
| JP | 02/064704 | 2/2002 |
| JP | 02/099250 | 4/2002 |
| JP | 03/255915 | 9/2003 |
| JP | 04/184937 | 7/2004 |
| JP | 04/212503 | 7/2004 |
| JP | 05/293265 | 10/2005 |
| JP | 05/309338 | 11/2005 |
| JP | 05/346639 | 12/2005 |
| JP | 06/84710 | 3/2006 |
| JP | 3766231 | 4/2006 |
| JP | 06/308665 | 11/2006 |
| JP | 07/140404 | 6/2007 |
| JP | 07/225871 | 9/2007 |
| JP | 07/310319 | 11/2007 |
| JP | 07/322944 | 12/2007 |
| JP | 08/021207 | 1/2008 |
| JP | 08/107715 | 5/2008 |
| JP | 08/116554 | 5/2008 |
| JP | 09/031585 | 2/2009 |
| JP | 08/287118 | 11/2009 |
| RU | 05/129914 | 4/2007 |
| WO | WO 94/10138 | 5/1994 |
| WO | WO 96/11932 | 4/1996 |
| WO | WO 96/21452 | 7/1996 |
| WO | WO 96/32907 | 10/1996 |
| WO | WO 97/16443 | 5/1997 |
| WO | WO 97/21701 | 6/1997 |
| WO | WO 97/30992 | 8/1997 |
| WO | WO 98/06700 | 2/1998 |
| WO | WO 98/28264 | 7/1998 |
| WO | WO 98/28303 | 7/1998 |
| WO | WO 98/40383 | 9/1998 |
| WO | WO 98/49157 | 11/1998 |
| WO | WO 98/54174 | 12/1998 |
| WO | WO 99/45712 | 9/1999 |
| WO | WO 99/45912 | 9/1999 |
| WO | WO 00/01691 | 1/2000 |
| WO | WO 00/02871 | 1/2000 |
| WO | WO 00/12498 | 3/2000 |
| WO | WO 00/12499 | 3/2000 |
| WO | WO 00/27820 | 5/2000 |
| WO | WO 00/39082 | 7/2000 |
| WO | 01/49667 A1 | 7/2001 |
| WO | WO 01/47897 | 7/2001 |
| WO | WO 01/47919 A1 | 7/2001 |
| WO | WO 01/49667 | 7/2001 |
| WO | WO 02/32861 A2 | 4/2002 |
| WO | WO 02/068406 | 9/2002 |
| WO | WO 02/092599 A1 | 11/2002 |
| WO | WO 03/024931 A1 | 3/2003 |
| WO | WO 03/024969 A1 | 3/2003 |
| WO | WO 03/035009 A1 | 5/2003 |
| WO | WO 03/037347 A1 | 5/2003 |
| WO | WO 03/057690 A1 | 7/2003 |
| WO | WO 03/099771 A2 | 12/2003 |
| WO | WO 03/099796 | 12/2003 |
| WO | WO 2004/005281 A1 | 1/2004 |
| WO | WO 2004/016597 A2 | 2/2004 |
| WO | 2004/022525 A1 | 3/2004 |
| WO | WO 2004/018419 A2 | 3/2004 |
| WO | WO 2004/022525 | 3/2004 |
| WO | WO 2004/039782 A1 | 5/2004 |
| WO | WO 2004/043389 A2 | 5/2004 |
| WO | WO 2004/045548 | 6/2004 |
| WO | WO 2004/045549 | 6/2004 |
| WO | WO 2004/046120 A2 | 6/2004 |
| WO | WO 2004/058749 A1 | 7/2004 |
| WO | WO 2004/085388 | 10/2004 |
| WO | 2004/096795 A3 | 11/2004 |
| WO | WO 2004/096795 | 11/2004 |
| WO | WO 2005/012220 | 2/2005 |
| WO | WO 2005/040139 | 5/2005 |
| WO | WO 2005/047273 | 5/2005 |
| WO | WO 2005/073225 | 8/2005 |
| WO | WO 2006/047277 A2 | 5/2006 |
| WO | WO 2006/047504 A1 | 5/2006 |
| WO | WO 2006/135630 | 12/2006 |
| WO | WO 2006/135636 | 12/2006 |

(56) References Cited

FOREIGN PATENT DOCUMENTS

| WO | WO 2006/135713 | 12/2006 |
|----|----|----|
| WO | WO 2006/135718 | 12/2006 |
| WO | WO 2006/138155 A1 | 12/2006 |
| WO | WO 2007/048088 | 4/2007 |
| WO | 2004/096795 A2 | 5/2008 |
| WO | WO 2009/058968 | 5/2009 |
| WO | WO 2009/157224 | 12/2009 |

OTHER PUBLICATIONS

Yu et al., "Physical characterization of, etc.," PSTT, vl. 1(3), 118-127 (1998).*
Vippagunta et al., "Crystalline Solids", Advanced Drug Delivery Reviews 48 (2001) 3-26.*
Braga et al., "Making crystals from . . . " J. Royal Soc. Chem. Commun. p. 3635-3645 (2005).*
Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Invanisevic et al. "Use of X-ray . . . " Pharm. Sci. Encycl. p. 1-42 (2010).*
Bhattacharya excerpt fr Brittain, H. ed., Polymorphism in Pharmaceutical SolidsDrugs and the Pharmaceutical Sciences ; V. 95 New York Marcel Dekker, Inc., 1999.*
Ivanisevic, I. Pharm. Form. Qual. 2011, pp. 30-33.*
Kirk-Othmer "Crystallization" Encyclopedia of Chem. Tech. v. 8, p. 95-147 (2002).*
Seddon "Pseudopolymorph . . . " Crystal Growth & design v.4(6) p. 1087 (2004) (2 pages from internet).*
U.S. Office Action mailed Jan. 24, 2013 for corresponding U.S. Appl. No. 12/736,660.
Abstract of Japanese Patent Publication JP06-178277 published on Jun. 24, 1994.
Abarbri et al., J. Org. Chem. (2000), 65, 4618-4634.
Abdel-Magid et al, "Reductive Amination of Aldehydes and Ketones with Sodium Triacetoxyborohydride.Studies on Direct and Indirect Reductive Amination Procedures", J Org. Chem., vol. 61 pp. 3849-3862 (1996).
Aboutaleb et al., International Sem in Surgical Oncol 6(17): 1-3, 2006.
Acute myeloid leukemia: MedlinePlus Medical Encyclopedia. Retrieved on Dec. 28, 2010. Electronic Resource: http://www.nlm.nih.gov/medlineplus/ency/article/000542.htm].
Advani, A., Curr Hematologic Malignancy Reports 1:101-107,2006.
Altman et al. The Cancer Dictionary, 1992, pp. 30-32.
Ansari-Lari, A. et al., "FLT3 mutations in myeloid sarcoma" British Journal of Haematology. Sep. 2004 126(6):785-91.
Armstrong, S.A. et al., (2004) "FLT3 mutations in childhood acute lymphoblastic leukemia." Blood. 103: 3544-6.
Arnon et al., "Monoclonal Antibodies for Immunotargeting of Drugs in Cancer Therapy", in Monoclonal Antibodies and Cancer Therapy, Reisfeld et al. (eds.), pp. 243-256 (Alan R. Liss, Inc. 1985).
Auewarakul et al., Ann Hematol, 85:108-112, 2006.
Barkenbus et al., Journal of Organic Chemistry (1951), 16, 232-8.
Baumann et al.. J Biochem Biophys Methods. 2004; 60:69-79.
Beletskaya et al., Chem. Rev., 100:3009 (2000).
Beller et al., Applied Homogeneous Catalysis with Organometallic Compounds, Cornils, B. and Herrmann, W. A. (Eds.), 2, 1009-1024, VCH, Weinheim, Germany (1996).
Berenbaum et al. What is synergy? Pharmacological Reviews, 1989.
Berge, S., et al, "Pharmaceutical Salts", J. Pharm. Sci., Jan. 1977, 66(1): 1-19.
Blouin et al. Rat models of bone metastases. Clin. Exp. Metastasis, 2005, 22: 605-614.
Bodansky, M. et al., "The Practice of Peptide Synthesis", Springer-Verlag, NY (1984).
Brase et al., Angew. Chemie Int. Ed., 44(33), 5188-5240, (2005).

Brase et al., Metal-Catalyzed Cross-Coupling Reactions (2nd Edition), p. 217-315, A. de Meijere, F. Diederich, Eds., Wiley-VCH, Weinheim (2004).
British Journal of Haematology, "Flt3 mutations and leukemia", 2003,122(4):523-38.
Brown et al., J. Chem. Soc., Perkin Trans. 2, 1039-1051 (2002).
Buchner T., W. Hiddemann, et al. (2002). "Acute myeloid leukemia: treatment over 60." Rev Clin Exp Hematol. 6(1):46-59.
Buchwald, E.L. et al., Top. Curr. Chem., 219:131-209 (2001).
Burnett, A. K. (2002). "Acute myeloid leukemia: treatment of adults under 60 years." Rev Clin Exp Hematol 6(1): 26-45.
Byrn et al., Solid-State Chemistry of Drugs, Second Edition, 1999, pp. 233-247.
Canibano, V. et al., Synthesis 14, 2175 (2001).
ChemBlink. Tipifarnib. Electronic Resource. Retrived on Dec. 18, 2010: [http://www.chemblink.com/products/192185-72-1.htm].
Chou TC, Talalay P. (1984) "Quantitative analysis of dose-effect relationships: the combined effects of multiple drugs or enzyme inhibitors." Adv Enzyme Regul. 22:27-55.
Clohlsy et al. Bone Cancer Pain. (Presented at the Third North American Symposium on Skeletal Complications of Malignancy, Bethesda, Maryland; Apr. 25-27, 2002).
Coll. Czech. Chem. Commun.: 31(11), 4432-41, (1966), Palecek, J.
Comprehensive Organic Transformations: Larock, R.S.; Wiley and Sons Inc., USA 1999.
Corey et al., Tetrahedron Lett., 29, 995 (1988).
Cortes. Farnesyltransferase inhibitors in acute myeloid leukemia and myelodysplastic syndromes. Clinical Lymphoma, vol. 4, Suppl. 1, S30-S35, 2003.
Couturier et al., Organic Process Research & Development, 2002, 6, 42-48.
Crandall et al., J. Am. Chem. Soc. (1968), 90, 6251-6253.
Cummins et al., Tetrahedron (1988), 44(16), 5151.
Dib, et al., European Journal of Pharmacology. 2006, pp. 27-33, 551.
Dirlam et al., J. Heterocyclic Chem, 17, 409, (1980).
Dolan, S., et al, J. Chem., Soc., Chem. Commun., 1588-9 (1985).
Drexler, H. G. et al. (2004), "FLT3: receptor and ligand"; Growth Factors 22(2):71-3.
Drexler, H.G., "The Leukemia-Lymphoma Cell Line Factsbook", Academic Pres:SanDiego, CA, 2000.
Eastwood, P., Tetrahedron Lett. (2000), 41, 3705-8.
Ferrara et al., "Prognostic factors and therapeutic options for relapsed or refractory acute myeloid leukemia." Haematologica. Aug. 2004, vol. 89, No. 8, Aug. 2004; pp. 998-1008.
Fohlisch et al, Liebigs Annalen der Chemie, (1), 1-5 (1987) [English Abstract provided].
Galemmo et al., J. Med. Chem., 33(10), 2828-41; (1990).
Gavezzotti, "Are Crystal Structures Predictable?" Accounts of Chemical Research, vol. 27, pp. 309-314 (1994).
Gilliand, G., et.al, "The roles of FLT3 in mematopoiesis and leukemia", Blood. 2002; 100:1532-42.
Gotlib, J (2005) "Farnesyltransferase inhibitor therapy in acute myelogenous leukemia." Curr. Hematol. Rep.;4(1):77-84.
Gould, P., "Salt selection for basic drugs", Ref. International J. Pharm. 1986, 33, 201-217.
Gray, M. et al., Tetrahedron Lett., 41:6237-40 (2000).
Griswold, I. J. et al., "Effects of MLN518, A Dual FLT3 and KIT inhibitor, on Normal and Malignant Hematopoiesis" Blood, Jul. 2004 [Epub ahead of print].
Guanti et al., Tetrahedron, 46 (20), 7081, (1990).
Guanti et al., Tetrahedron: Asymmetry 8(13), 2175-2187, (1997).
Haluska P., G.K. Dy, A.A. Adjei. (2002) "Farnesyl transferase inhibitors as anticancer agents." Eur J Cancer. 38(13):1685-700.
Han, J., Advances in Characterization of Pharmaceutical Hydrates, Trends in Bio/PharmaceuticalIndustry, pp. 25-29. Mar. 2006.
Harmata et al., Org. Lett. (2000), 2, 2703-2705.
Hartwig, J.F., "Organopalladium Chemistry for Organic Synthesis," Wiley Interscience, NY (2002).
Hayakawa et al., Bioorg. Med. Chem. Lett., 14(2): 455-8 (2004).
Hellstrom et al., "Antibodies for Drug Delivery", in Controlled Drug Delivery (2nd Ed.), Robinson et al. (eds.), pp. 623-653 (Marcel Dekker, Inc. 1987).

(56) References Cited

OTHER PUBLICATIONS

Hengartner, MO. (2000) "The biochemistry of apoptosis." Nature 407:770-76.
Hess et al., J. Am. Chem. Soc. (1998), 120, 12310.
Hill et al., J. Am. Chem. Soc. (1973), 95, 1338.
Hogermeier et al., Chem. Eur. J., 2007, 13, 2410.
Hulkenberg et al., *Tetrahedron Lett.*, 23(14), 1505-08; (1982).
Iddon. B. et al., J. Chem. Soc. Perkin Trans. 1., 1370, (1980).
Illig, et al., "Discovery of novel FMS Kinase Inhibitors As Anti-inflammatory Agents" Bioorganic & Medicinal Chemistry Letters, Pergamon, 2008, pp. 1642-1648 vol. 18, No. 5.
Ishikubo et al (Jpn J Clin Oncol 36:494-498, 2006.
Itsuno et al., *Synthesis*, 12, 995-6, (1988).
Johnson et al., Brit J Cancer, 84:1424-1431 (2001).
Johnson et al., J. Org. Chem. (1970), 35(3), 584-592.
Kamwakami J., et al. "A Convenient Synthesis of 4(5)-Alkylacyl-1 H-imidazoles from 4(5)-Imidazolecarboxaldehyde" Synthesis, No. 5, pp. 677-680 (2003).
Katritsky, A. et al., "*para*-Formylation of Nitroarenes via Vicarious Nucleophilic Substitution of Hydrogen with Tris(benzotriazol-1-yl)methane", Tetrahedron Lett., 37:347-50 (1996).
Khanapure et al, *J. Med. Chem.*, 48(11): 3930-34 (2005).
Kim et al., European Journal of Organic Chemistry (2000), 12, 2195-2201.
Kolder, C.R., et al, "Synthesis and Reactivity of 5-Chloro-2,4-Dihydrosypyridine", x Recl. Trav. Chim. Pays-Bas; 285 (1953).
Koutek, et al, *Synth. Commun.*, 6 (4), 305-8 (1976).
Lancet J.E., J.D. Rosenblatt, J.E. Karp. (2003) "Farnesyltransferase inhibitors and myeloid malignancies: phase I evidence of Zarnestra activity in high-risk leukemias." Semin Hematol. 39(3 Suppl 2):31-5.
Larock, R.C., Comprehensive Organic Transformations, $2^{nd}$ Ed., Wiley-VCH, NY, (1999), pp. 996-1003.
Lee, K. and Cha, J. K., J. Amer. Chem. Soc., 123: 5590-5591 (2001).
Leonard et al., *J. Org. Chem.*, 28, 3021, (1963).
Levis, M. et al. 2001, "A FLT3 tyrosine kinase inhibitor is selectively cytoxic to acute myeloid leukemia blasts harboring FLT3 internal tandem duplication mutations", Blood 98(3):885-7.
Levis, M. et al., "Novel FLT3 tyrosine kinase inhibitors" Expert Opin. Investing. Drugs (2003) 12 (12) 1951-1962.
Levis, M. et al., "Small Molecule FLT3 Tyrosine Kinase Inhibitors" Current Pharmaceutical Design, 2004, 10, 1183-1193.
Levis, M., et al. (2004) "In vitro studies of a FLT3 inhibitor combined with chemotherapy: sequence of administration is important to achieve synergistic cytotoxic effects." Blood. 104(4):1145-50.
Lewis, et al. "Diacetoxypiperidinium Analogs of Acetylcholine", Junal of Medicinal Chemistry, 1973, vol. 16, No. 2 pp. 156-159.
Lipshutz et al., Tetrahedron Lett. (1988), 29, 3411-3414.
Liu et al., *J. Am. Chem. Soc.* 2004, 126, 5182.
Loader, C., et al, Can. J. Chem, 59, 2673 (1981).
Lovborg H, Gullbo J, Larsson R. (2005) "Screening for apoptosis-classical and emerging techniques." Anticancer Drugs 16:593-9.
Lyon, R., et al., "Synthesis and Evaluation of Phenyl-and Benzoylpiperazines as Potential Serotonergic Agents", J. Med. Chem., 29: 630-4 (1986).
Major, R., et al. "1-Alkoxy-4-phenyl-4-propionoxypiperdines and Their 3-Methyl Homologs as New Analgesics", vol. 26, pp. 1867-1847, (1961).
Martinez_Teipel et al., *QSAR & Combinatorial Science*, 23(10), 854-858 (2004).
McBee et al., Journal of the American Chemical Society (1957), 79, 2323-5.
McKenna, H.J. et al., "Mice lacking flt3 ligand having deficient hematopoiesis affecting hematopoietic progenitor cells, dendritic cells and natural killer cells", Blood Jun. 2000; 95:3489-3497.
Meltzer et al., Bioorganic & Medicinal Chemistry (2002), 10(11) and 3583-3591.
Miyaura, N. et al., "Palladium-Catalyzed Cross-Coupling Reactions of Organoboron Compounds", Chem. Rev. 95:2457 (1995).
Mock et al., *J. Phys. Org. Chem.*, 16(3), 175-182 (2003).

Modern Amination Methods: Ricci, A., Ed., Wiley-VCH: Weinheim, 2000.
Muci, et al., "Practical Palladium Catalysts for C-N and C-O Bond Formation", Top. Curr., Chem. 219-131-209 (2001).
Murata, K. et al., "Selective cytotoxic mechanism of GTP-14564, a novel tyrosine kinase inhibitor in leukemia cells expressing a constitutively active Fms-like tyrosine kinase 3 (FLT3)" J Biol Chem. Aug. 29, 2003; 278(35):32892-8.
Murata, K. et al., "Synthesis of Alkenylboronates via Palladium-Catalyzed Borylation of Alkenyl Triflates (or Iodindes) with Pinacolborane" Synthesis, 2000, No. 6, pp. 778-780.
Murray, et al., "SU11248 inhibits tumor growth and CSF-1R-dependent osteolysis in an experimental breast cancer bone metastasis model", Clinical & Experimental Metastasis, 2003, pp. 757-766, vol. 20, No. 8.
Myles et al., *J. Org. Chem.*, 55, 1636 (1990).
Nguyen et al., *Tetrahedron*, 62(4), 647-651; (2006).
Nicolai, E., et al., "New Process for the Synthesis of Imidazo[4-5-b] pyridine Derivatives as Potent Orally Active Thromboxane $A_2$ Receptor Antagonists", J. Heterocyclic Chemistry, 31, (73) (1994).
Nose et al., *Chem. Pharm. Bull.*, 38(8), 2097-101, (1990).
Noyori et al., Org. React., 1983, 29, 163.
Nunez G, Benedict MA, Hu Y, Inohara N. (1998) "Caspases: the proteases of the apoptotic pathway." Oncogene 17:3237-45.
O'Farrell, A.M. et al. "SU11248 is a novel FLT3 tyrosine kinase inhibitor with potent activity in vitro and in vivo" Blood, May 2003; 101:3597-3605.
Olah, G.A. et al., "Formylating Agents", Chemical Reviews, vol. 87, No. 4, 1987.
Prendergast et al., (2001) "Farnesyl Transferase Inhibtors: Mechanism and Applications" Expert Opin Investig Drugs. 10(12):2105-16.
Protecting Groups, P, Kocienski Thieme Medical Publishers, 2000.
Pure Appl. Chem., 1976, 45:13-30.
Quentmeier H, et al. FLT3 mutations in acute myeloid leukemia cell lines. Leukemia. Jan. 2003;17:120-124.
Quintard et al., *J. Org. Chem.*, 48: 1559-60 (1983).
Reed et al., *Synthetic Communications*, 20(4), 563-71, (1990).
Regan, J., et al., Structure-Activity Relationships of the p38* MAP Kinsase Inhibitor 1-)5-*tert*-Butyl-2-*p*-tolyl-2h-pyrazol-3-yl)-3-[4-(2-morpholin-4-yl-ethoxy)naph-thalen-1-yl-)urea (BIRB 796)J. Med. Chem., 46:4676-86 (2003).
Reinecke et al., Chemistry—A European Journal (1995), 1(6), 368-73.
Romeo, G., et al, "New Pyrimido [5,4-b_indoles as Ligands for *1-Adrenoceptor Subtypes", J. Med. Chem., 46: 2877-2894 (2003).
Roush, W., *J. Am. Chem. Soc.* 102, 1390 (1980).
Sadick, M. et al., Analysis of Heregulin-Induced ErbB2 Phosphorylation with a High-Throughput Kinase Receptor Activation Enzyme-Linked Immunosorbent Assay, Analytical Biochemistry. 1996; 235:207-214.
Sasaki et al., Tett. Lett. (1982), 23, 1693.
Sato et al., Bulletin of the Chemical Society of Japan (1983), 56(9), 2680-99.
Sato et al., Bulletin of the Chemical Society of Japan (1984), 57(9), 2515-25.
Scheijen, B. et al. (2002), "Tyrosine kinase oncogenes innormal hematopoiesis and hematological disease", Oncogene 21(21):3314-33.
Schmid et al., Helv. Chim. Acta. (1974), 57, 1883 [see English Summary provided].
Sendelbach, et al, Journal of Organic Chemistry (1999), 64(10), 3398-3408.
Shih L. Y. et al., (2004) "Internal tandem duplication of fms-like tyrosine kinase 3 is associated with poor outcome in patients with myelodysplastic syndrome." Cancer, 101; 989-98.
Simpson WG, The calcium channel blocker verapamil and cancer chemotherapy. Cell Calcium. Dec. 1985;6(6):449-67.
Smith, B. D. et al., "Single-agent CEP-701, a novel FLT3 inhibitor, shows biologic and clinical activity in patients with relapsed or refractory acute myeloid leukemia" Blood, May 2004; 103:3669-3676.
Smith, P, "The Curtius Reaction", Organic Reactions 3:337 (1947).

(56) References Cited

OTHER PUBLICATIONS

Stille, J.K., "The Palladium-Catalyzed Cross-Coupling Reactions of Organotin Reagents with Organic Electrophiles", Angew, Chem, Int. Ed. Engl., 25:508-524 (1986).
Stirewalt, D.L. et al. (2003), "The role of FLT3 in haematopoietic malignancies", NatRev Cancer 3(9):650-65.
Stone, R.M. et al. "PKC 412 FLT3 inhibitor therapy in AML: results of a phase II trial" An Hematol 2004; 83 Suppl 1:S89-90.
Sundermeier, U., Doebler, C. and Beller, M., Modern Oxidation Methods, Baeckvall, J. (Ed.)., 1-20, Wiley-Verlag (2004) Weinheim, Germany (2004).
Suzuki, A., "Metal-Catalyzed Coupling Reactions" F. Deiderich, P. Stang, Eds., Wiley-VCH, Weinheim (1998).
Takada, Y., et al. (2004). "Protein farnesyltransferase inhibitor (SCH 66336) abolishes NF-kappaB activation induced by various carcinogens and inflammatory stimuli leading to suppression of NF-kappaB-regulated gene expression and up-regulation of apoptosis."J Biol Chem 279, 26287-99.
Takahashi, K., et al, Chem. Lett. (2000), 126-7.
Takaya et al., J Amer Chem Soc, (1978), 100(6), 1765-77.
Thalhammer et al. Duration of second complete remission in patients with acute myeloid leukemia treated with chemotherapy: a retrospective single-center study. Ann. Hematology, 1996, 72: 216-222.
Thompson et al., Journal of Industrial and Engineering Chemistry (Washington, D. C.) (1952), 44,1659-62.
Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985).
Tohma et al., *Adv. Syn. Catalysis*, 346, 111-124 (2004).
Tse, K.F. et al., "Inhibition of FLT3-mediated transformation by use of a tyrosine kinase inhibitor" Leukemia, Jul. 15, 2001(7):1001-10.
van Engeland M., L.J. Nieland ,et al. (1998) "Annexin V-affinity assay: a review on an apoptosis detection system based on phosphatidylserine exposure." Cytometry. 31(1):1-9.
Walker et al, Dermatol 212:70-72, 2006 (Abstract Only).
West et al., J. Org. Chem (1993), 58, 6795-6803.
Wilson et al., Reducing Ion Channel Activity in a Series of 4-Heterocyclic Arylamide FMS Inhibitors, 20 Bioorg. & Med. Chem. Letts. 3925-3929 (2010).
Wroblewski et al., Journal of the American Chemical Society (1996), 118, 10168-10174.
Wustrow, et al, "Coupling of Arylboronic Acids with a Partially Reduced Pyridine Derivative" Synthesis, 993 (1991).
Wustrow et al., Tetrahedron Lett., 35, 61-4 (1994).
www.cancer.org (accessed online Mar. 2, 2010), "Can Acute Myeloid Luchemia (AML) Be Prevented?".
Yee et al. Synergistic effect of SU11248 with cytarabine or daunorubicin on FLT3 ITD-positive leukemic cells. Blood, 2004, 104: 4202-4209. Published online Aug. 10, 2004.
Yee, K.W.H. et al., "SU5416 and SU5614 inhibit kinase activity of wild-type and mutant FLT3 receptor tyrosine kinase" Blood, Sep. 2002; 100:2941-294.
Zhu et al. Farnesyltransferase inhibitor R115777 (Zarnestra, Tipifarnib) synergizes with paclitaxel to induce apoptosis and mitotic arrest and to inhibit tumor growth of multiple myeloma cells. Blood, vol. 105, No. 12, 4759-4766, Published online Feb. 22, 2005.
Chemcats RN 93730-20-2, Nov. 28, 1988.
Chemcats RN 443895-82-7 Apr. 24, 2003.
Chemcats RN 701272-70-0, Jan. 1, 2004.
Chemcats RN 712290-43, Jan. 1, 2004.
Jonas, Nilsson W. et al., "Solid-Phase Synthesis of Libraries Generated from a 4-Phenyl-2-carboxy-piperazine Scaffold", J. Comb. Chem., 2001, 3, 546-553.
Moffett, Robert Bruce et al., "Antiulcer Agents. p-Aminobenzamido Aromatic Compounds", Journal of Medicinal Chemistry, 1971, vol. 14, No. 10, pp. 963-968.
Nilsson et al., J. Comb. Chem., vol. 3, pp. 546-553 (2001).
Rastelli et al. J. Med. Chem., 2003, 46, 2834-2845.
International Search Report dated Oct. 10, 2007 for PCT/US2007/066868.
International Search Report dated Oct. 10, 2007 for PCT/US2007/066870.
Braga, D., et al., "Making crystals from crystals: a green route to crystal engineering and polymorphism", J. Royal Soc. Chem. Commun. (2005), pp. 3635-3645.
Bernstein, J., "Polymorphism in Molecular Crystals", Clarendon Press Oxford, (2002), vol. 272, pp. 115-118.
Davidovich, M., et al., "Detection of Polymorphism by Powder X-Ray Diffraction; Interference by Preferred Orientation", Am. Pharm. Rev., (2004), vol. 7, No. 1, pp. 10, 12, 14, 16, 100.
Dean, J.A., "Analytical Chemistry Handbook", McGraw-Hill, Inc., (1995), pp. 10.24-10.26.
Ivanisevic, I., et al., "Uses of X-Ray Powder Diffraction in the Pharmaceutical Industry", Pharm. Sci. Encycl., (2010), pp. 1-42.
Bhattacharya excerpt fr Brittain, H., ed., Polymorphism in Pharmaceutical SolidsDrugs and the Pharmaceutical Sciences; vol. 95, New York Marcel Dekker, Inc. (1999).
Ivanisevic, I., et al., "Uses of X-Ray Powder Diffraction in the Pharmaceutical Industrty", Pharm. Form. Qual, (2011), pp. 30-33.
Kirk-Othmer "Crystallization", Encyclopedia of Chem. Tech, (2002), vol. 8, pp. 95-147, John Wiley & Sons, Inc.
Seddon, K.R., "Pseudopolymorph: A Polemic", Crystal Growth & Design, (2004), vol. 4, No. 6, p. 1087 (two pages from internet), American Chemical Society.

\* cited by examiner

INHIBITORS OF C-FMS KINASE

CROSS REFERENCE TO RELATED APPLICATION

This application is a divisional of U.S. patent application Ser. No. 11/736,644, filed Apr. 18, 2007, pending; which claims priority to U.S. Provisional Patent Application 60/793,667, filed Apr. 20, 2006.

BACKGROUND OF THE INVENTION

The invention relates to novel compounds that function as protein tyrosine kinase inhibitors. More particularly, the invention relates to novel compounds that function as inhibitors of c-fms kinase.

Protein kinases are enzymes that serve as key components of signal transduction pathways by catalyzing the transfer of the terminal phosphate from adenosine 5'-triphosphate (ATP) to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain. Receptor binding leads to the initiation of multiple intracellular tyrosine kinase dependent phosphorylation processes, which ultimately results in oncogene transcription. Breast, colorectal and prostate cancers have been linked to this family of receptors.

Insulin receptor ("IR") and insulin-like growth factor I receptor ("IGF-1R") are structurally and functionally related but exert distinct biological effects. IGF-1R overexpression has been associated with breast cancer.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy.

Fibroblast growth factor ("FGR") receptors consist of four receptors which are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF are designated as VEGFR-1 (Flt-1), VEGFR-2 (KDR), VEGFR-3 (Flt-4). A related group of receptors, tie-1 and tie-2 kinases, have been identified in vascular endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity. Thus, a need exists for selective and potent small-molecule protein tyrosine kinase inhibitors. U.S. Pat. Nos. 6,383,790; 6,346,625; 6,235,746; 6,100,254 and PCT International Applications WO 01/47897, WO 00/27820 and WO 02/068406 are indicative of recent attempts to synthesize such inhibitors.

SUMMARY OF THE INVENTION

The invention addresses the current need for selective and potent protein tyrosine kinase inhibitors by providing potent inhibitors of c-fms kinase. The invention is directed to the novel compounds of Formula I:

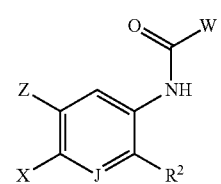

or a solvate, hydrate, tautomer or pharmaceutically acceptable salt thereof, wherein:
W is

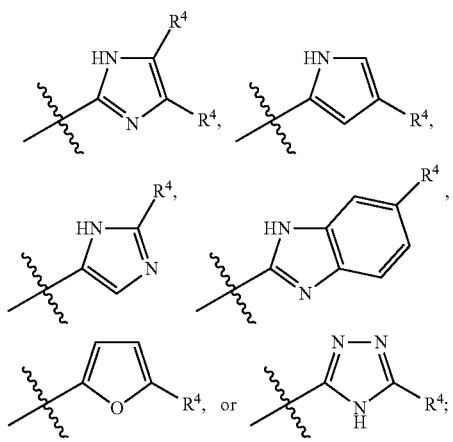

wherein each $R^4$ is independently H, F, Cl, Br, I, OH, $OCH_3$, $OCH_2CH_3$, $SC_{(1-4)}$alkyl, $SOC_{(1-4)}$alkyl, $SO_2C_{(1-4)}$alkyl, —$C_{(1-3)}$alkyl, $CO_2R^d$, $CONR^eR^f$, C≡$CR^g$, or CN;
  wherein $R^d$ is H, or —$C_{(1-3)}$alkyl;
    $R^e$ is H, or —$C_{(1-3)}$alkyl;
    $R^f$ is H, or —$C_{(1-3)}$alkyl; and
    $R^g$ is H, —$CH_2OH$, or —$CH_2CH_2OH$;

$R^2$ is cycloalkyl, spiro-substituted cycloalkenyl, heterocyclyl, spirosubstituted piperidinyl, thiophenyl, dihydrosulfonopyranyl, phenyl, furanyl, tetrahydropyridyl, or dihydropyranyl, any of which may be independently substituted with one or two of each of the following: chloro, fluoro, hydroxy, $C_{(1-3)}$alkyl, and $C_{(1-4)}$alkyl;

Z is H, F, or $CH_3$;

J is CH, or N;

X is

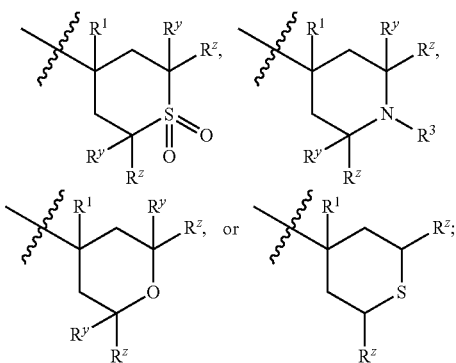

wherein $R^1$ is —$C_{(1-4)}$alkyl, —$OR^a$, —CN, —$NA^1A^2$, —$SO_2CH_3$, —$COOR^a$, —$CO_2CH_3$, —$CH_2$—$NA^1A^2$, —$CONA^1A^2$, —$CH_2OR^a$, —$OC_{(1-4)}$alkyl$OR^a$, —$NHCH_2CH_2CO_2R^a$, —$NHCH_2CH_2OR^a$, —$NR^aCH_2CH_2NA^1A^2$, —$OC_{(1-4)}$alkyl$NA^1A^2$, —$OCH_2CO_2R^a$, —$CH_2CO_2R^a$, —$CH_2CH_2SO_2C_{(1-4)}$alkyl, —$SO_2CH_2CH_2NA^1A^2$, —$SOCH_2CH_2NA^1A^2$, —$SCH_2CH_2NA^1A^2$, —$NHSO_2CH_2CH_2NA^1A^2$, phenyl, imidazolyl, thiazolyl, 4H-[1,2,4]oxadiazol-5-onyl, 4H-pyrrolo[2,3-b]pyrazinyl, pyridinyl, [1,3,4]oxadiazolyl, 4H-[1,2,4]triazolyl, tetrazolyl, pyrazolyl, [1,3,5]triazinyl, and [1,3,4]thiadiazolyl;

$R^z$ and $R^y$ are independently H or —$C_{(1-4)}$alkyl, wherein both $R^z$ may have either syn or anti stereochemistry; alternatively both $R^z$ in a syn relationship may be taken together to form —$(CH_2)_n$—, where n is 2 or 3;

$R^3$ is H, $C_{(1-4)}$alkyl, $C_{(1-3)}$alkyl-$CF_3$, $CH_2CH_2NH_2$, $CH_2CH_2OR^a$, —$COCH_3$, $CONH_2$, or $CO_2R^a$;

$A^1$ is H, —$C_{(1-4)}$alkyl, or $CH_2CH_2OR^a$;

$A^2$ is H, —$C_{(1-4)}$alkyl, $COR^a$, $CH_2CON(CH_3)_2$, —$CH_2CH_2OR^a$, —$CH_2CH_2SC_{(1-4)}$alkyl, —$CH_2CH_2SOC_{(1-4)}$alkyl, or —$CH_2CH_2SO_2C_{(1-4)}$alkyl;

alternatively, $A^1$ and $A^2$ may be taken together with their attached nitrogen to form a heterocyclic ring selected from the following:

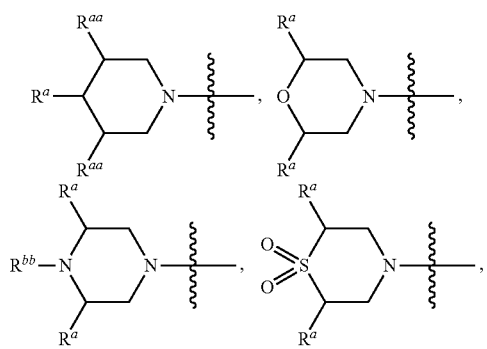

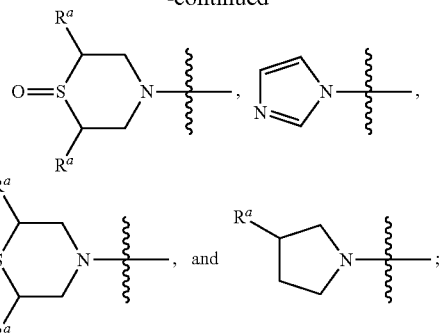

wherein $R^a$ is H or $C_{(1-4)}$alkyl;

$R^{aa}$ is H or $C_{(1-4)}$alkyl;

$R^{bb}$ is H, —$C_{(1-4)}$alkyl, —$CH_2CH_2OCH_2CH_2OCH_3$, —$CH_2CO_2H$, —$C(O)C_{(1-4)}$alkyl, or —$CH_2C(O)C_{(1-4)}$alkyl;

Herein and throughout this application, whenever a variable, for example $R^a$, appears more than once in an embodiment of Formula I, each such substitution is independently defined. Herein and throughout this application, the terms "Me", "Et", "Pr", and "Bu" refer to methyl, ethyl, propyl, and butyl respectively.

DETAILED DESCRIPTION OF THE INVENTION

The invention is directed to novel compounds of Formula I:

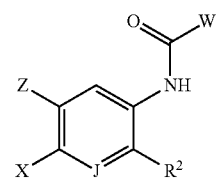

or a solvate, hydrate, tautomer or pharmaceutically acceptable salt thereof, wherein:

W is

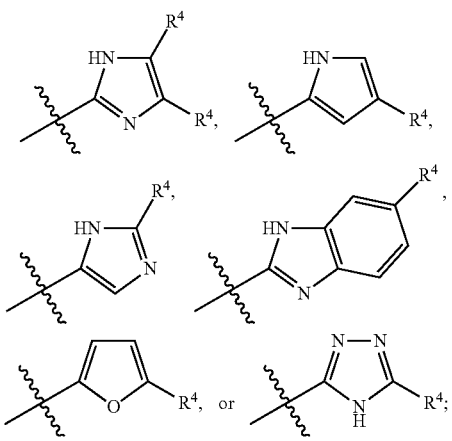

wherein each $R^4$ is independently H, F, Cl, Br, I, OH, $OCH_3$, $OCH_2CH_3$, $SC_{(1-4)}$alkyl, $SOC_{(1-4)}$alkyl, $SO_2C_{(1-4)}$alkyl, —$C_{(1-3)}$alkyl, $CO_2R^d$, $CONR^eR^f$, C≡$CR^g$, or CN;

wherein $R^d$ is H, or —$C_{(1-3)}$alkyl;
$R^e$ is H, or —$C_{(1-3)}$alkyl;
$R^f$ is H, or —$C_{(1-3)}$alkyl; and
$R^g$ is H, —$CH_2OH$, or —$CH_2CH_2OH$;

$R^2$ is cycloalkyl (including cyclohexenyl, and cycloheptenyl), spiro-substituted cycloalkenyl (including spiro[2.5]oct-5-enyl, spiro[3.5]non-6-enyl, spiro[4.5]dec-7-enyl, and spiro[5.5]undec-2-enyl) heterocyclyl (including piperidinyl), spirosubstituted piperidinyl (including 3-aza-spiro[5.5] undecanyl, and 8-aza-spiro[4.5]decanyl), thiophenyl, dihydrosulfonopyranyl, phenyl, furanyl, tetrahydropyridyl, or dihydropyranyl, any of which may be independently substituted with one or two of each of the following: chloro, fluoro, hydroxy, $C_{(1-3)}$alkyl, and $C_{(1-4)}$alkyl (said substituted cycloalkyls include 4,4-dimethyl cyclohexenyl, 4,4-diethyl cyclohexenyl, 4-methyl cyclohexenyl, 4-ethyl cyclohexenyl, 4-n-propyl cyclohexenyl, 4-iso-propyl cyclohexenyl, and 4-tert-butyl cyclohexenyl; said substituted piperidinyls include 4-methyl piperidinyl, 4-ethyl piperidinyl, 4-(1'hydroxyeth-2'yl)piperidinyl, and 4,4 dimethyl piperidinyl);

Z is H, F, or $CH_3$;
J is CH, or N;
X is

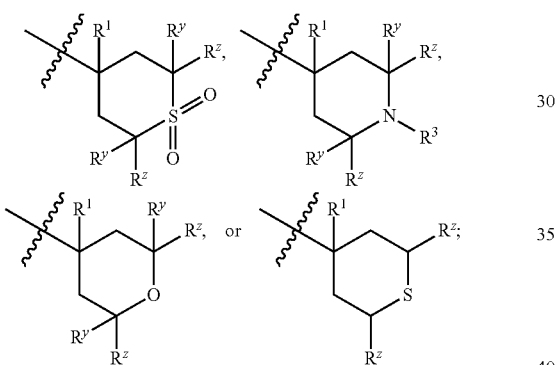

wherein $R^1$ is —$C_{(1-4)}$alkyl, —$OR^a$, —CN, —$NA^1A^2$, —$SO_2CH_3$, —$COOR^a$, —$CO_2CH_3$, —$CH_2$—$NA^1A^2$, —$CONA^1A^2$, —$CH_2OR^a$, —$OC_{(1-4)}$alkyl$OR^a$, —$NHCH_2CH_2CO_2R^a$, —$NHCH_2CH_2OR^a$, —$NR^aCH_2CH_2NA^1A^2$, —$OC_{(1-4)}$alkyl$NA^1A^2$, —$OCH_2CO_2R^a$, —$CH_2CO_2R^a$, —$CH_2CH_2SO_2C_{(1-4)}$alkyl, —$SO_2CH_2CH_2NA^1A^2$, —$SOCH_2CH_2NA^1A^2$, —$SCH_2CH_2NA^1A^2$, —$NHSO_2CH_2CH_2NA^1A^2$, phenyl, imidazolyl, thiazolyl, 4H-[1,2,4]oxadiazol-5-onyl, 4H-pyrrolo[2,3-b]pyrazinyl, pyridinyl, [1,3,4]oxadiazolyl, 4H-[1,2,4]triazolyl, tetrazolyl, pyrazolyl, [1,3,5]triazinyl, and [1,3,4]thiadiazolyl;

$R^z$ and $R^y$ are independently H or —$C_{(1-4)}$alkyl, wherein both $R^z$ may have either syn or anti stereochemistry; alternatively both $R^z$ in a syn relationship may be taken together to form —$(CH_2)_n$—, where n is 2 or 3;

$R^3$ is H, $C_{(1-4)}$alkyl, $C_{(1-3)}$alkyl-$CF_3$ (including —$CH_2CF_3$), $CH_2CH_2NH_2$, $CH_2CH_2OR^a$, —$COCH_3$, $CONH_2$, or $CO_2R^a$;

$A^1$ is H, —$C_{(1-4)}$alkyl, or $CH_2CH_2OR^a$;
$A^2$ is H, —$C_{(1-4)}$alkyl, $COR^a$, $CH_2CON(CH_3)_2$, —$CH_2CH_2OR^a$ (including —$CH_2CH_2OCH_3$), —$CH_2CH_2SC_{(1-4)}$alkyl (including —$CH_2CH_2SCH_3$), —$CH_2CH_2SOC_{(1-4)}$alkyl (including —$CH_2CH_2SOCH_3$), or —$CH_2CH_2SO_2C_{(1-4)}$alkyl (including —$CH_2CH_2SO_2CH_3$);

alternatively, $A^1$ and $A^2$ may be taken together with their attached nitrogen to form a heterocyclic ring selected from the following:

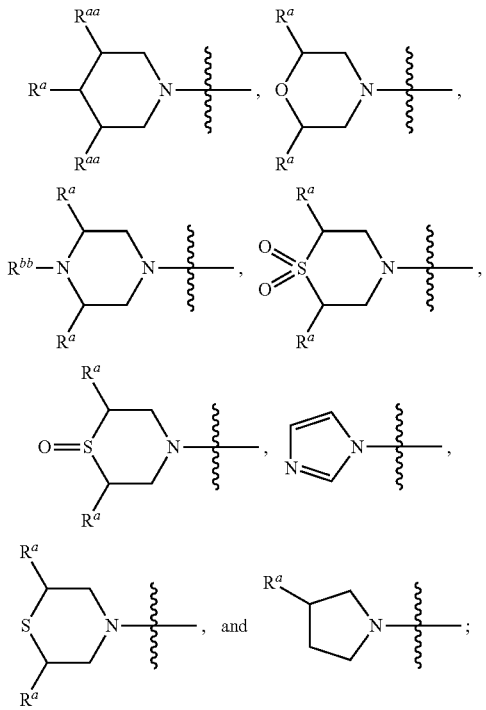

wherein $R^a$ is H or $C_{(1-4)}$alkyl;
$R^{aa}$ is H or $C_{(1-4)}$alkyl;
$R^{bb}$ is H, —$C_{(1-4)}$alkyl, —$CH_2CH_2OCH_2CH_2OCH_3$, —$CH_2CO_2H$, —$C(O)C_{(1-4)}$alkyl, or —$CH_2C(O)C_{(1-4)}$alkyl.

In a preferred embodiment of the invention:
W is

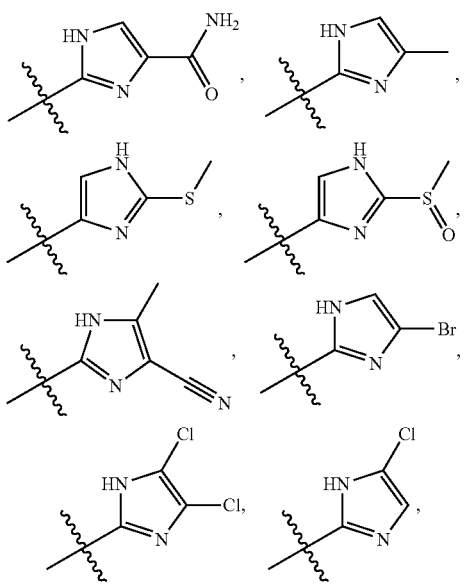

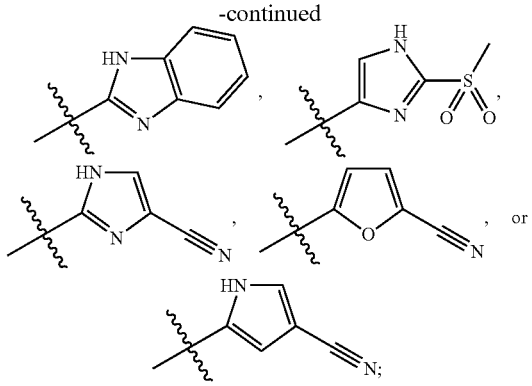

R² is

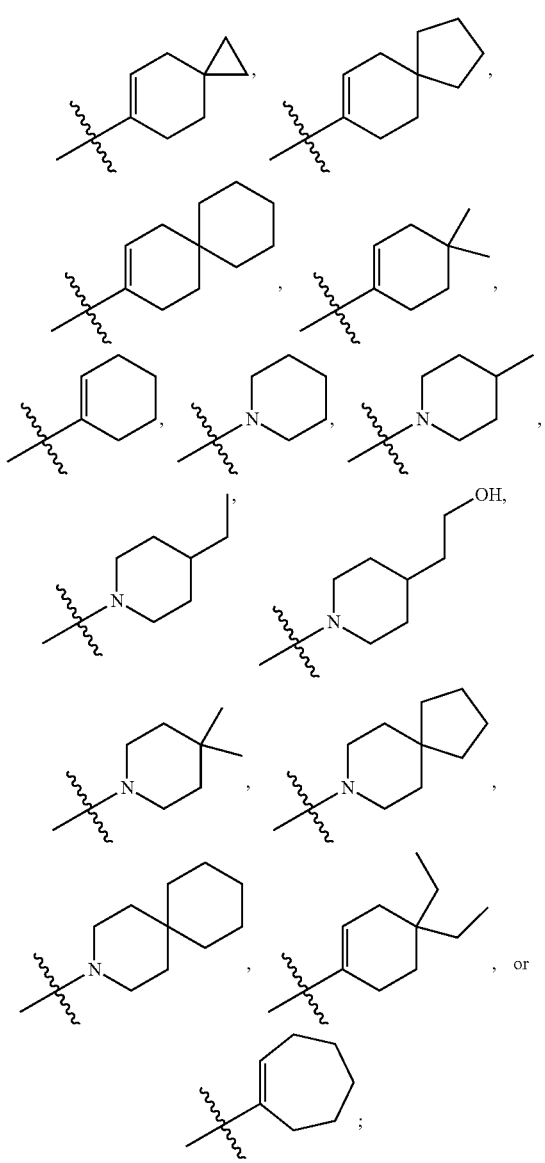

Z is H;
J is CH or N;

X is

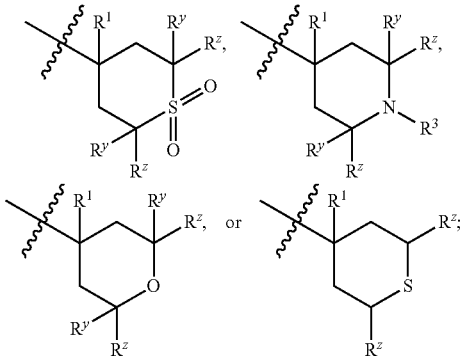

wherein R¹ is —OH, —CN, —NA¹A², —SO₂CH₃, —COOR$^a$, —CO₂CH₃, —CH₂—NA¹A², —CONA¹A², —CH₂OR$^a$, —NHCH₂CH₂CO₂R$^a$, —NHCH₂CH₂OR$^a$, —NHCH₂CH₂NA¹A², —OC$_{(1-4)}$alkylNA¹A², —OCH₂CO₂R$^a$, or tetrazolyl;
A¹ is H, or —CH₃;
A² is H, —CH₂CH₂OCH₃, —COCH₃, or —CH₃;
alternatively, A¹ and A² may be taken together with their attached nitrogen to form a heterocyclic ring selected from the following:

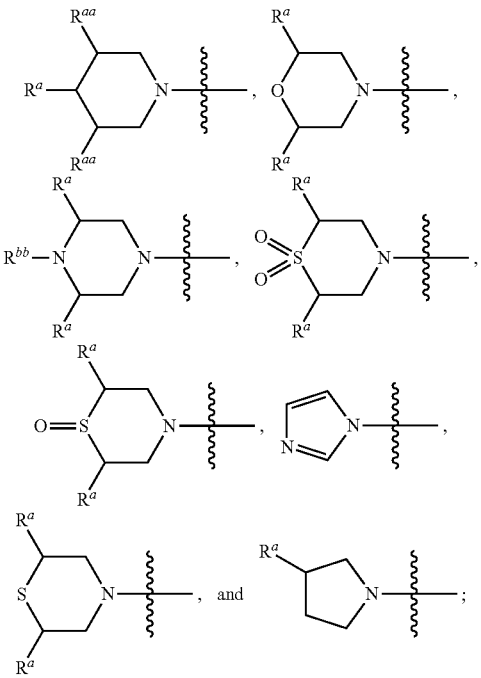

R$^a$ is H, or —C$_{(1-4)}$alkyl;
R$^{aa}$ is H, or —C$_{(1-4)}$alkyl;
R$^{bb}$ is H, —C$_{(1-4)}$alkyl, —CH₂CO₂H or —COCH₃;
R$^y$ is H, or —CH₃;
R$^z$ is H, —CH₃, or may be taken together as —CH₂CH₂—;
R³ is H, —COCH₃, —CH₂CF₃, —CH₃, —CO₂CH₃, —CONH₂, or —CO₂H.
as well as solvates, hydrates, tautomers and pharmaceutically acceptable salts thereof.

In another embodiment of the invention:
W is

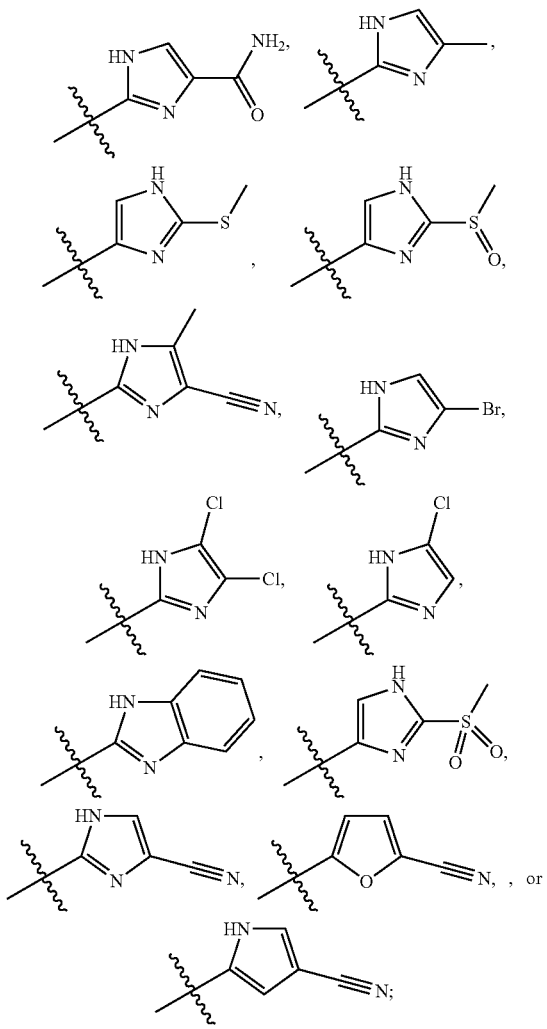

R² is

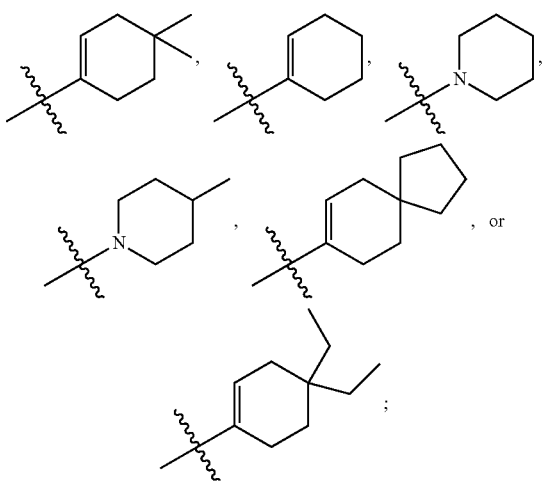

Z is H;
J is CH, or N;
X is

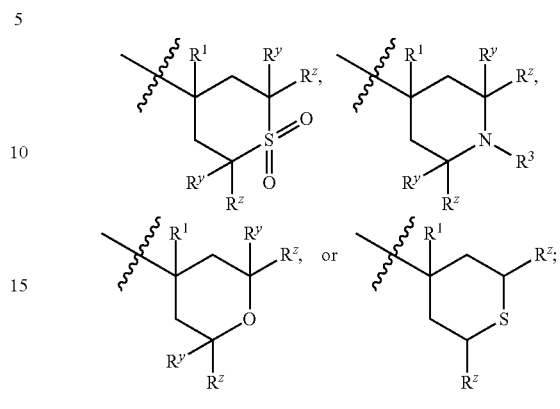

wherein R¹ is —OH, —CN, —NA¹A², —SO₂CH₃, —COOH, —CO₂CH₃, —CH₂—NA¹A², —CONH₂, —CON(CH₃)₂, —CH₂OH, —OCH₂CH₂N(CH₃)₂, —NHCH₂CH₂CO₂CH₃, —NHCH₂CH₂OCH₃, —NHCH₂CH₂NA¹A², —OC$_{(1-4)}$alkylNA¹A², —OCH₂CO₂H, or tetrazolyl;
A¹ is H, or —CH₃;
A² is H, —CH₂CH₂OCH₃, —COCH₃, or —CH₃;
alternatively, A¹ and A² may be taken together with their attached nitrogen to form a heterocyclic ring selected from the following:

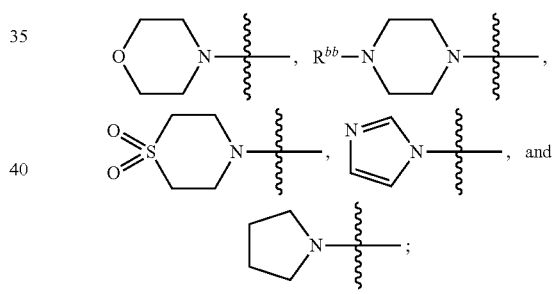

R$^{bb}$ is H, —C$_{(1-4)}$alkyl, —CH₂CO₂H or —COCH₃;
R$^y$ is H, or —CH₃;
R$^z$ is H, —CH₃, or may be taken together as —CH₂CH₂—;
R³ is H, —COCH₃, —CH₂CF₃, —CH₃, —CO₂CH₃, —CONH₂, or —CO₂H.
as well as solvates, hydrates, tautomers and pharmaceutically acceptable salts thereof.
In another embodiment of the invention:
W is

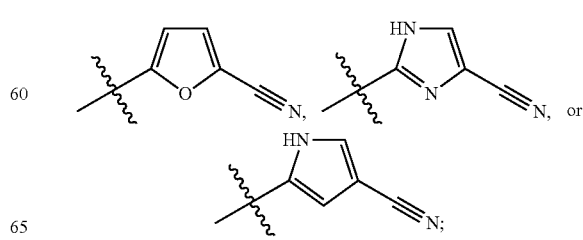

$R^2$ is

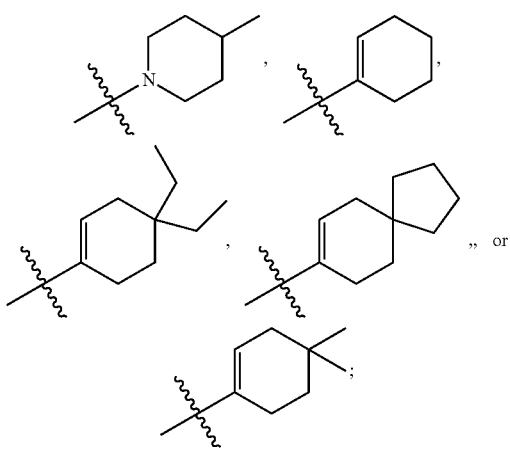

Z is H;
J is CH, or N;
X is

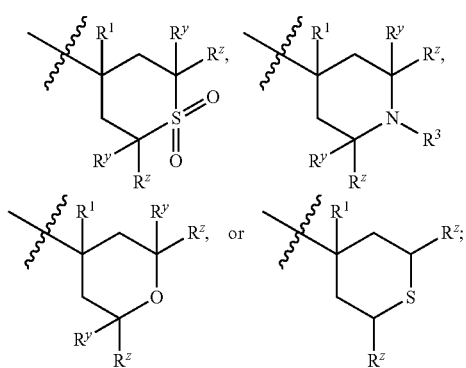

wherein $R^1$ is —OH, —CN, —$NA^1A^2$, —$SO_2CH_3$,
—COOH, —$CO_2CH_3$, —$CH_2$—$NA^1A^2$, —$CONH_2$,
—$CON(CH_3)_2$, —$CH_2OH$, —$OCH_2CH_2N(CH_3)_2$,
—$NHCH_2CH_2CO_2CH_3$, —$NHCH_2CH_2OCH_3$,
—$NHCH_2CH_2NA^1A^2$, —$OC_{(1-4)}$alkyl$NA^1A^2$,
—$OCH_2CO_2H$, or tetrazolyl;
$A^1$ is H, or —$CH_3$;
$A^2$ is H, —$CH_2CH_2OCH_3$, —$COCH_3$, or —$CH_3$;
alternatively, $A^1$ and $A^2$ may be taken together with their attached nitrogen to form a heterocyclic ring selected from the following:

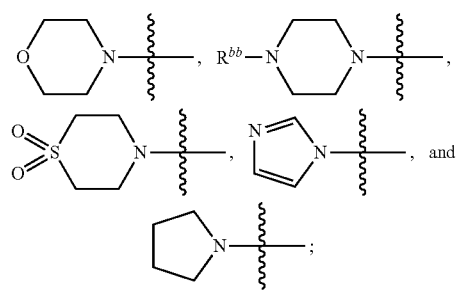

$R^{bb}$ is H, —$C_{(1-4)}$alkyl, —$CH_2CO_2H$ or —$COCH_3$;

$R^y$ is H, or —$CH_3$;
$R^z$ is H, —$CH_3$, or may be taken together as —$CH_2CH_2$—;
$R^3$ is H, —$COCH_3$, —$CH_2CF_3$, —$CH_3$, —$CO_2CH_3$, —$CONH_2$, or —$CO_2H$;

as well as solvates, hydrates, tautomers and pharmaceutically acceptable salts thereof.

In another embodiment of the invention:
W is

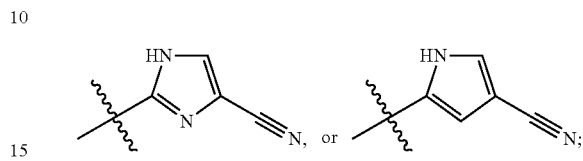

$R^2$ is

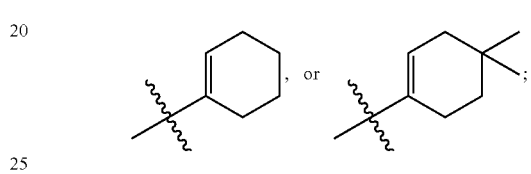

Z is H;
J is CH, or N;
X is

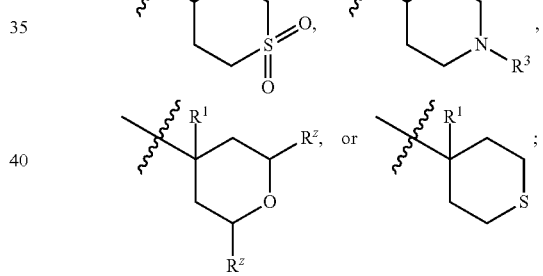

wherein $R^1$ is —OH, —$NH_2$, —$N(CH_3)_2$, —$SO_2CH_3$,
—COOH, —$CO_2CH_3$, —$CH_2$-morpholinyl,
—$CONH_2$, —$CON(CH_3)_2$, —$CH_2OH$, —$OCH_2CH_2N(CH_3)_2$, —$NHCH_2CH_2OCH_3$, —$OCH_2CO_2H$, morpholinyl, piperazinyl, N-methyl piperazinyl, piperazinyl-$CH_2CO_2H$, or tetrazolyl;
$R^z$ is H, or —$CH_3$;
$R^3$ is —$COCH_3$, —$CH_2CF_3$, or —$CO_2H$;

and solvates, hydrates, tautomers and pharmaceutically acceptable salts thereof.

In another embodiment of the invention:
W is

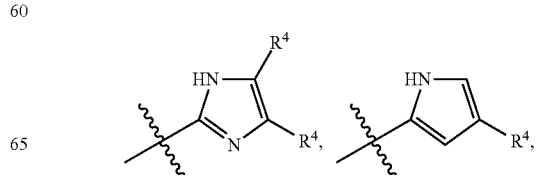

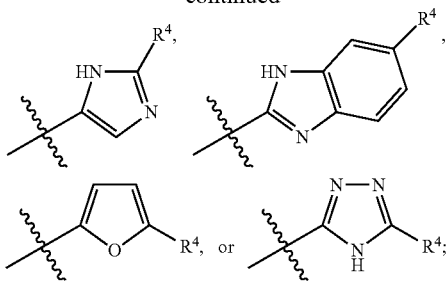

wherein each R⁴ is independently H, F, Cl, Br, I, OH, OCH₃, OCH₂CH₃, SC$_{(1-4)}$alkyl, SOC$_{(1-4)}$alkyl, SO₂C$_{(1-4)}$alkyl, —C$_{(1-3)}$alkyl, CO₂R$^d$, CONR$^e$R$^f$, C≡CR$^g$, or CN; wherein R$^d$ is H, or —C$_{(1-3)}$alkyl;
R$^e$ is H, or —C$_{(1-3)}$alkyl;
R$^f$ is H, or —C$_{(1-3)}$alkyl; and
R$^g$ is H, —CH₂OH, or —CH₂CH₂OH;

R² is cycloalkyl (including cyclohexenyl, and cycloheptenyl), spiro-substituted cycloalkenyl (including spiro[2.5]oct-5-enyl, spiro[3.5]non-6-enyl, spiro[4.5]dec-7-enyl, and spiro [5.5]undec-2-enyl) heterocyclyl (including piperidinyl), spirosubstituted piperidinyl (including 3-aza-spiro[5.5] undecanyl, and 8-aza-spiro[4.5]decanyl), thiophenyl, dihydrosulfonopyranyl, phenyl, furanyl, tetrahydropyridyl, or dihydropyranyl, any of which may be independently substituted with one or two of each of the following: chloro, fluoro, hydroxy, C$_{(1-3)}$alkyl, and C$_{(1-4)}$alkyl (said substituted cycloalkyls include 4,4-dimethyl cyclohexenyl, 4,4-diethyl cyclohexenyl, 4-methyl cyclohexenyl, 4-ethyl cyclohexenyl, 4-n-propyl cyclohexenyl, 4-iso-propyl cyclohexenyl, and 4-tert-butyl cyclohexenyl; said substituted piperidinyls include 4-methyl piperidinyl, 4-ethyl piperidinyl, 4-(1'hydroxyeth-2'yl)piperidinyl, and 4,4 dimethyl piperidinyl);

Z is H, F, or CH₃;
J is CH, or N;
X is

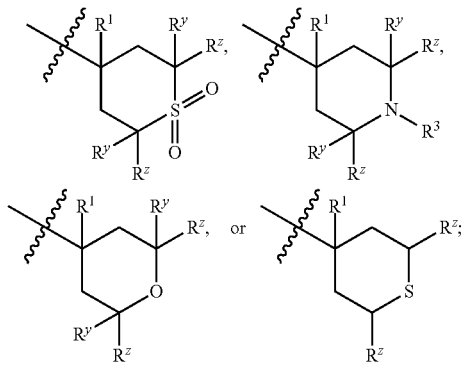

wherein R¹ is —C$_{(1-4)}$alkyl, —OR$^a$, —CN, —NA¹A², —SO₂CH₃, —COOR$^a$, —CO₂CH₃, —CH₂—NA¹A², —CONA¹A², —CH₂OR$^a$, —OC$_{(1-4)}$alkylOR$^a$, —NHCH₂CH₂CO₂R$^a$, —NHCH₂CH₂OR$^a$, —NR$^a$CH₂CH₂NA¹A², —OC$_{(1-4)}$alkylNA¹A², —OCH₂CO₂R$^a$, —CH₂CO₂R$^a$, —CH₂CH₂SO₂C$_{(1-4)}$alkyl, —SO₂CH₂CH₂NA¹A², —SOCH₂CH₂NA¹A², —SCH₂CH₂NA¹A², —NHSO₂CH₂CH₂NA¹A², phenyl, imidazolyl, thiazolyl, 4H-[1,2,4]oxadiazol-5-onyl, 4H-pyrrolo[2,3-b]pyrazinyl, pyridinyl, [1,3,4]oxadiazolyl, 4H-[1,2,4]triazolyl, tetrazolyl, pyrazolyl, [1,3,5]triazinyl, and [1,3,4] thiadiazolyl;

R$^z$ and R$^y$ are independently H or —C$_{(1-4)}$alkyl, wherein both R$^z$ may have either syn or anti stereochemistry; alternatively both R$^z$ in a syn relationship may be taken together to form —(CH₂)$_n$—, where n is 2 or 3;

R³ is H, C$_{(1-4)}$alkyl, CH₂CH₂NH₂, CH₂CH₂OR$^a$, —COCH₃, CONH₂, or CO₂R$^a$;

A¹ is H, —C$_{(1-4)}$alkyl, or CH₂CH₂OR$^a$;

A² is H, —C$_{(1-4)}$alkyl, COR$^a$, CH₂CON(CH₃)₂, —CH₂CH₂OR$^a$ (including —CH₂CH₂OCH₃), —CH₂CH₂SC$_{(1-4)}$alkyl (including —CH₂CH₂SCH₃), —CH₂CH₂SOC$_{(1-4)}$alkyl (including —CH₂CH₂SOCH₃), or —CH₂CH₂SO₂C$_{(1-4)}$alkyl (including —CH₂CH₂SO₂CH₃);

alternatively, A¹ and A² may be taken together with their attached nitrogen to form a heterocyclic ring selected from the following:

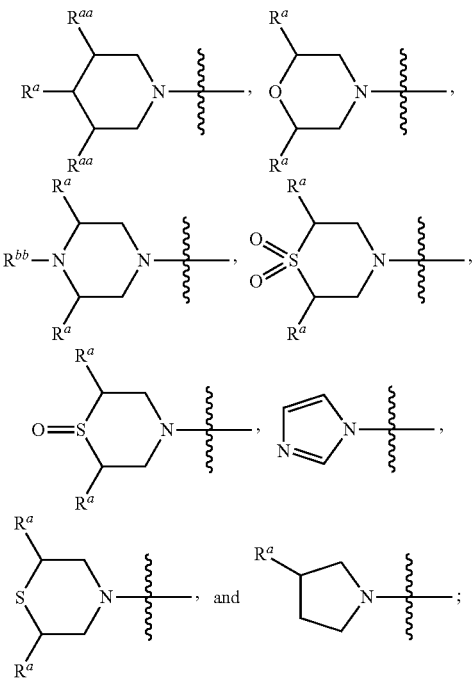

wherein R$^a$ is H or C$_{(1-4)}$alkyl;
R$^{aa}$ is H or C$_{(1-4)}$alkyl;
R$^{bb}$ is H, —C$_{(1-4)}$alkyl, —CH₂CH₂OCH₂CH₂OCH₃, —CH₂CO₂H, —C(O)C$_{(1-4)}$alkyl, or —CH₂C(O)C$_{(1-4)}$alkyl.

In a preferred embodiment of the invention:
W is

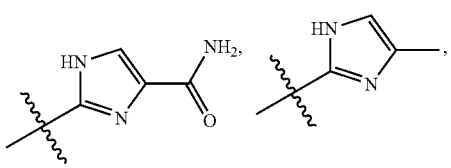

-continued

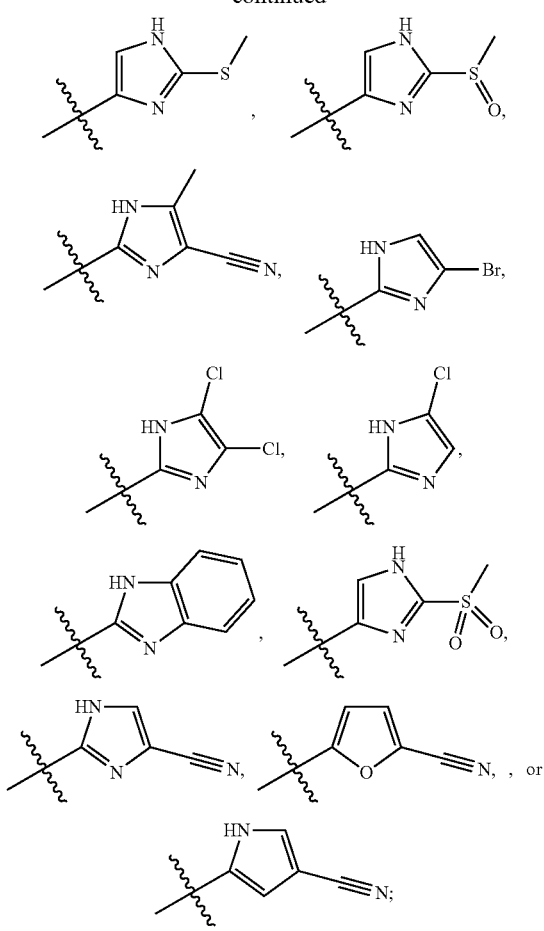

R² is

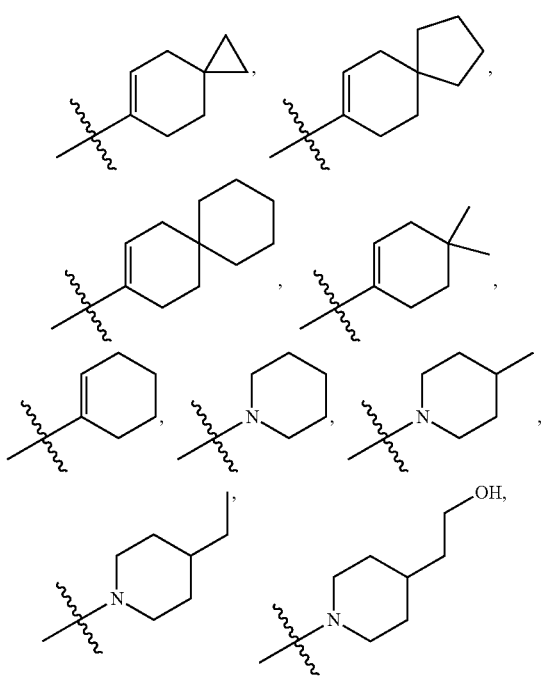

-continued

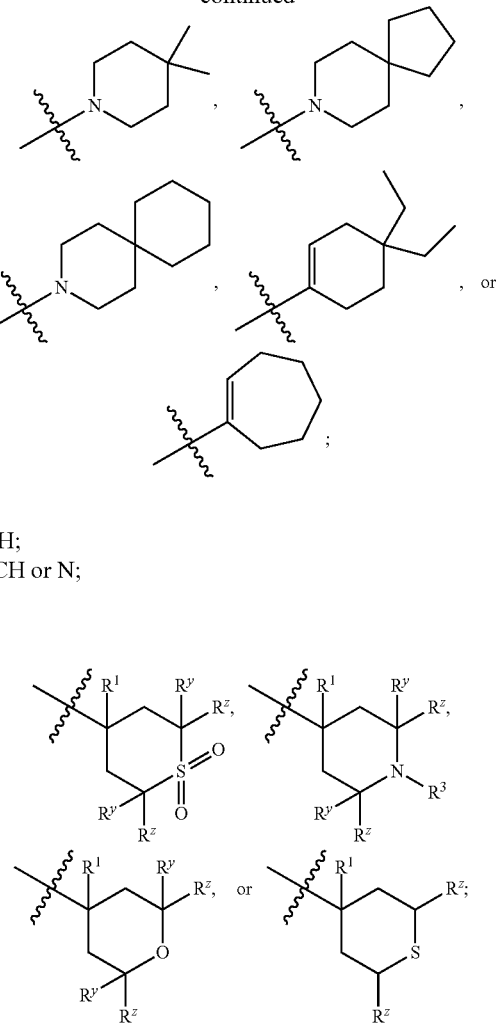

Z is H;
J is CH or N;
X is

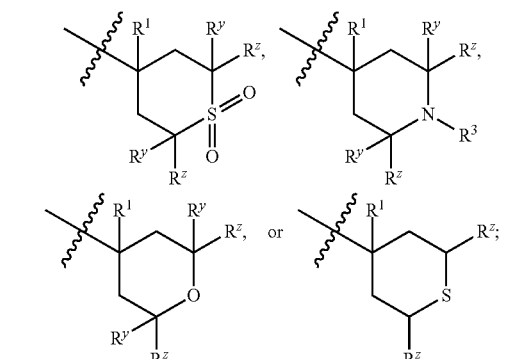

wherein R¹ is —OH, —CN, —NA¹A², —SO₂CH₃, —COOR$^a$, —CO₂CH₃, —CH₂—NA¹A², —CONA¹A², —CH₂OR$^a$, —NHCH₂CH₂CO₂R$^a$, —NHCH₂CH₂OR$^a$, —NHCH₂CH₂NA¹A², —OC$_{(1-4)}$alkylNA¹A², —OCH₂CO₂R$^a$, or tetrazolyl;
A¹ is H, or —CH₃;
A² is H, —CH₂CH₂OCH₃, —COCH₃, or —CH₃;
alternatively, A¹ and A² may be taken together with their attached nitrogen to form a heterocyclic ring selected from the following:

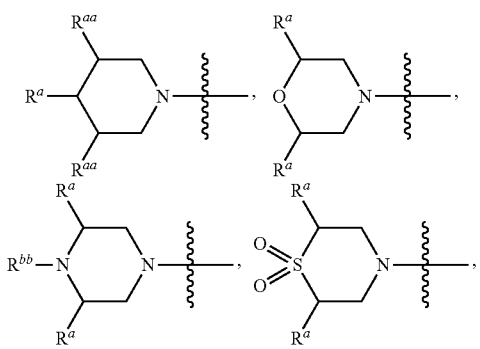

-continued

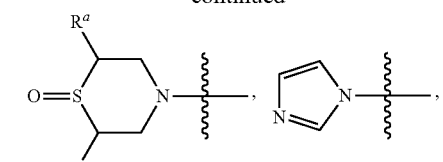

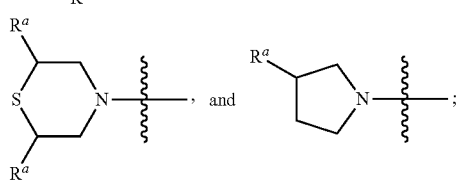

$R^a$ is H, or —C$_{(1-4)}$alkyl;
$R^{aa}$ is H, or —C$_{(1-4)}$alkyl;
$R^{bb}$ is H, —C$_{(1-4)}$alkyl, —CH$_2$CO$_2$H or —COCH$_3$;
$R^y$ is H, or —CH$_3$;
$R^z$ is H, —CH$_3$, or may be taken together as —CH$_2$CH$_2$—;
$R^3$ is H, —COCH$_3$, —CH$_3$, —CO$_2$CH$_3$, —CONH$_2$, or —CO$_2$H.

as well as solvates, hydrates, tautomers and pharmaceutically acceptable salts thereof.

In another embodiment of the invention:

W is

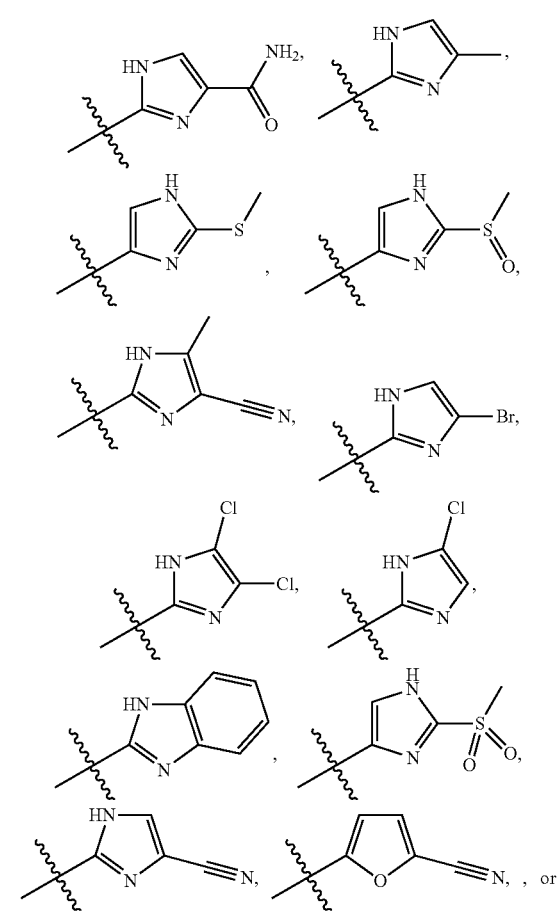

-continued

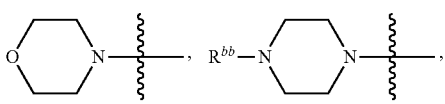

$R^2$ is

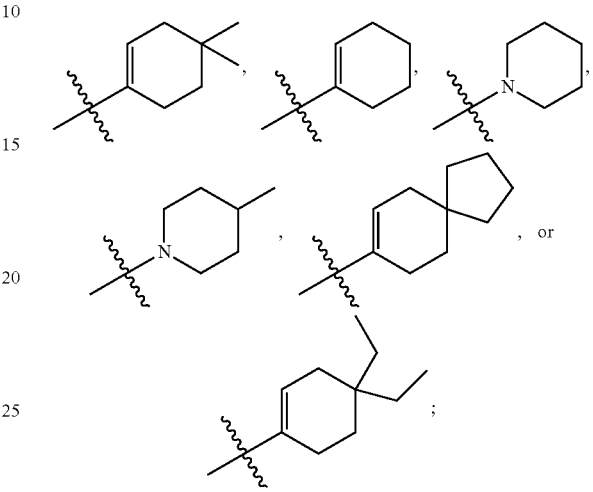

Z is H;
J is CH, or N;
X is

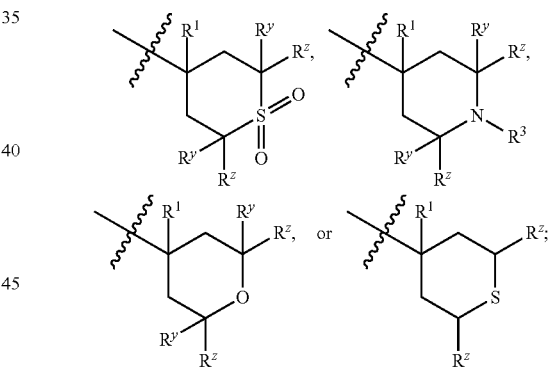

wherein $R^1$ is —OH, —CN, —NA$^1$A$^2$, —SO$_2$CH$_3$, —COOH, —CO$_2$CH$_3$, —CH$_2$—NA$^1$A$^2$, —CONH$_2$, —CON(CH$_3$)$_2$, —CH$_2$OH, —OCH$_2$CH$_2$N(CH$_3$)$_2$, —NHCH$_2$CH$_2$CO$_2$CH$_3$, —NHCH$_2$CH$_2$OCH$_3$, —NHCH$_2$CH$_2$NA$^1$A$^2$, —OC$_{(1-4)}$alkylNA$^1$A$^2$, —OCH$_2$CO$_2$H, or tetrazolyl;
$A^1$ is H, or —CH$_3$;
$A^2$ is H, —CH$_2$CH$_2$OCH$_3$, —COCH$_3$, or —CH$_3$;
alternatively, $A^1$ and $A^2$ may be taken together with their attached nitrogen to form a heterocyclic ring selected from the following:

-continued

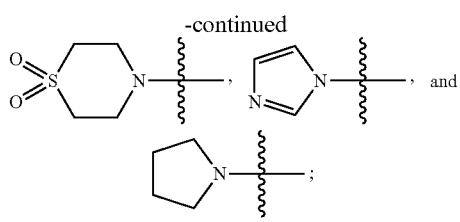

$R^{bb}$ is H, —$C_{(1-4)}$alkyl, —$CH_2CO_2H$ or —$COCH_3$;
$R^y$ is H, or —$CH_3$;
$R^z$ is H, —$CH_3$, or may be taken together as —$CH_2CH_2$—;
$R^3$ is H, —$COCH_3$, —$CH_3$, —$CO_2CH_3$, —$CONH_2$, or —$CO_2H$.

as well as solvates, hydrates, tautomers and pharmaceutically acceptable salts thereof.

In another embodiment of the invention:
W is

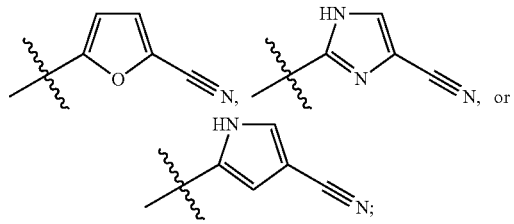

$R^2$ is

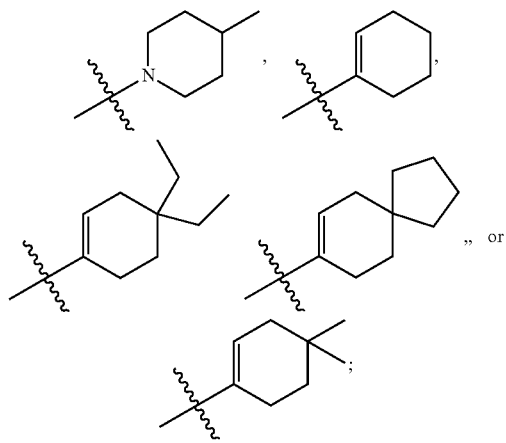

Z is H;
J is CH, or N;
X is

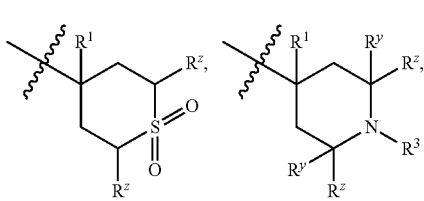

-continued

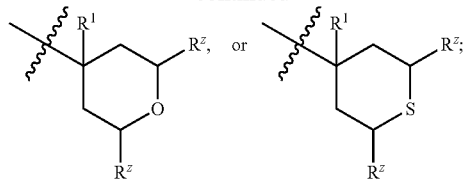

wherein $R^1$ is —OH, —CN, —$NA^1A^2$, —$SO_2CH_3$, —COOH, —$CO_2CH_3$, —$CH_2$—$NA^1A^2$, —$CONH_2$, —$CON(CH_3)_2$, —$CH_2OH$, —$OCH_2CH_2N(CH_3)_2$, —$NHCH_2CH_2CO_2CH_3$, —$NHCH_2CH_2OCH_3$, —$NHCH_2CH_2NA^1A^2$, —$OC_{(1-4)}$alkyl$NA^1A^2$, —$OCH_2CO_2H$, or tetrazolyl;

$A^1$ is H, or —$CH_3$;
$A^2$ is H, —$CH_2CH_2OCH_3$, —$COCH_3$, or —$CH_3$;

alternatively, $A^1$ and $A^2$ may be taken together with their attached nitrogen to form a heterocyclic ring selected from the following:

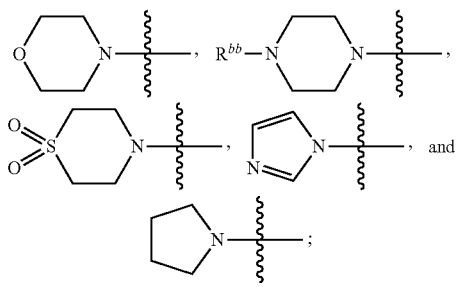

$R^{bb}$ is H, —$C_{(1-4)}$alkyl, —$CH_2CO_2H$ or —$COCH_3$;
$R^y$ is H, or —$CH_3$;
Rz is H, —$CH_3$, or may be taken together as —$CH_2CH_2$—;
$R^3$ is H, —$COCH_3$, —$CH_3$, —$CO_2CH_3$, —$CONH_2$, or —$CO_2H$;

as well as solvates, hydrates, tautomers and pharmaceutically acceptable salts thereof.

In another embodiment of the invention:
W is

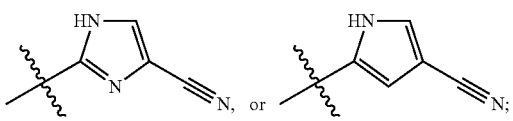 [SMILES: *c1nc(C#N)c[nH]1 ; *c1cc(C#N)c[nH]1 ; "or"]

$R^2$ is

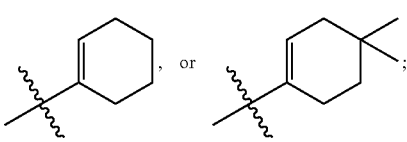

Z is H;
J is CH, or N;

X is

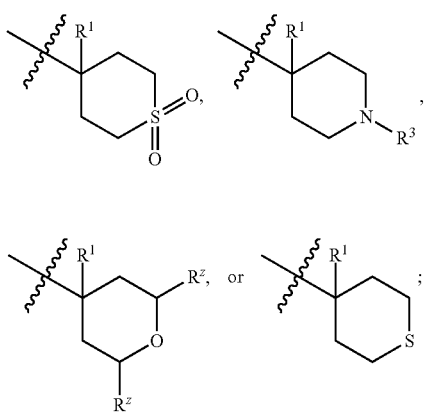

wherein R¹ is —OH, —NH₂, —N(CH₃)₂, —SO₂CH₃, —COOH, —CO₂CH₃, —CH₂-morpholinyl, —CONH₂, —CON(CH₃)₂, —CH₂OH, —OCH₂CH₂N(CH₃)₂, —NHCH₂CH₂OCH₃, —OCH₂CO₂H, morpholinyl, piperazinyl, N-methyl piperazinyl, piperazinyl-CH₂CO₂H, or tetrazolyl;

R$^z$ is H, or —CH₃;

R³ is —COCH₃, or —CO₂H;

and solvates, hydrates, tautomers and pharmaceutically acceptable salts thereof.

Another embodiment of the invention is a compound selected from the group consisting of:

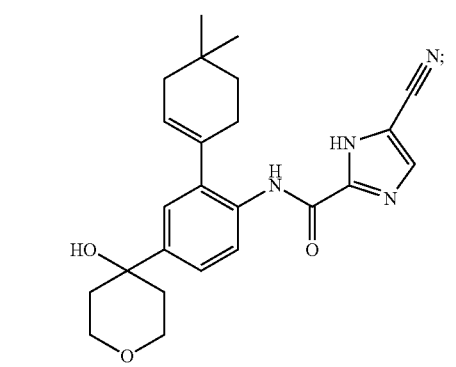

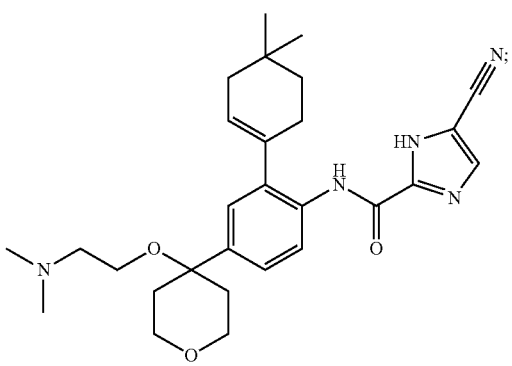

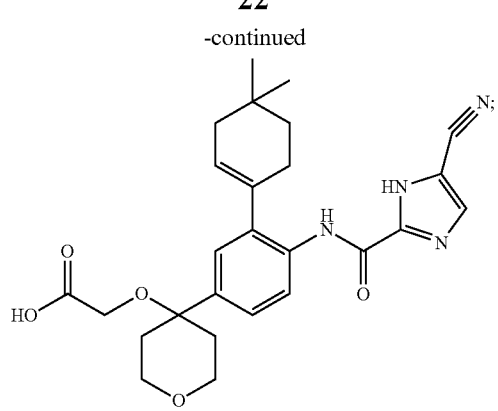

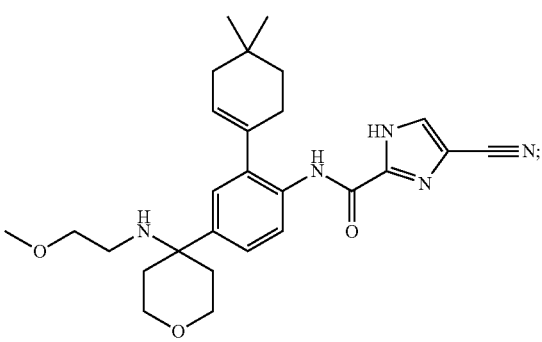

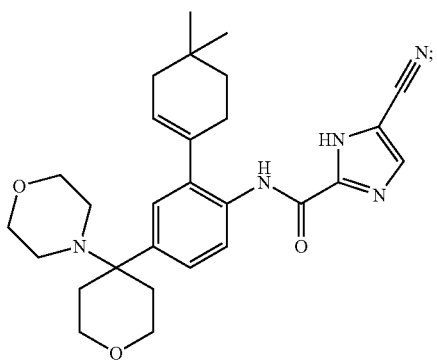

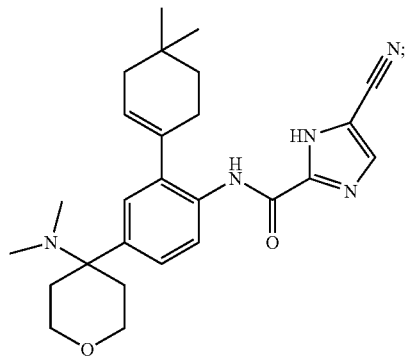
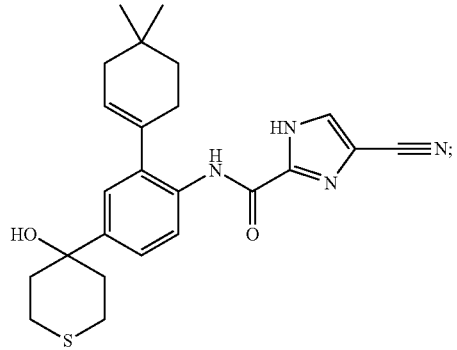
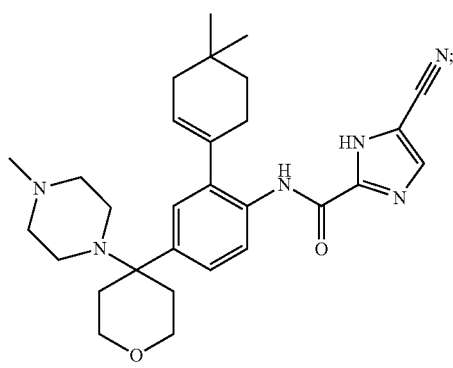
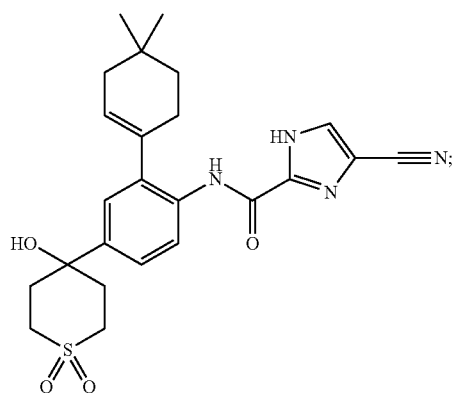
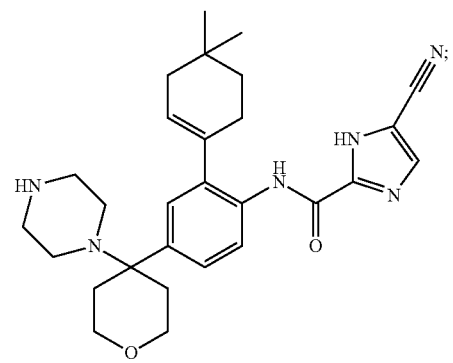
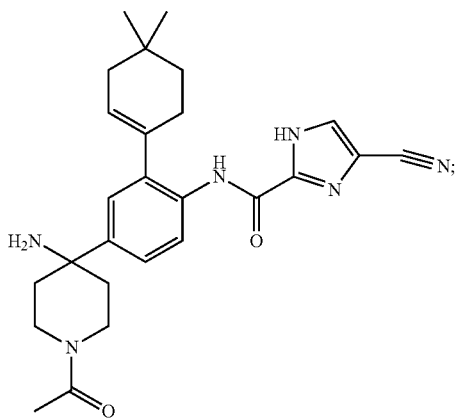
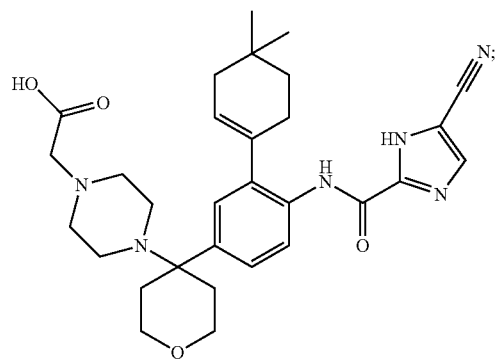
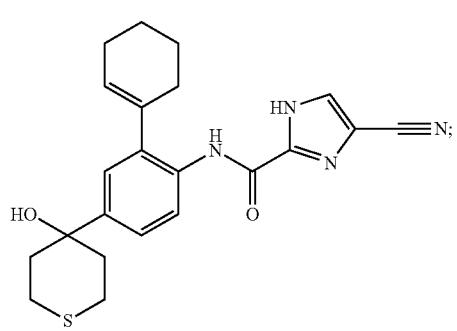

-continued
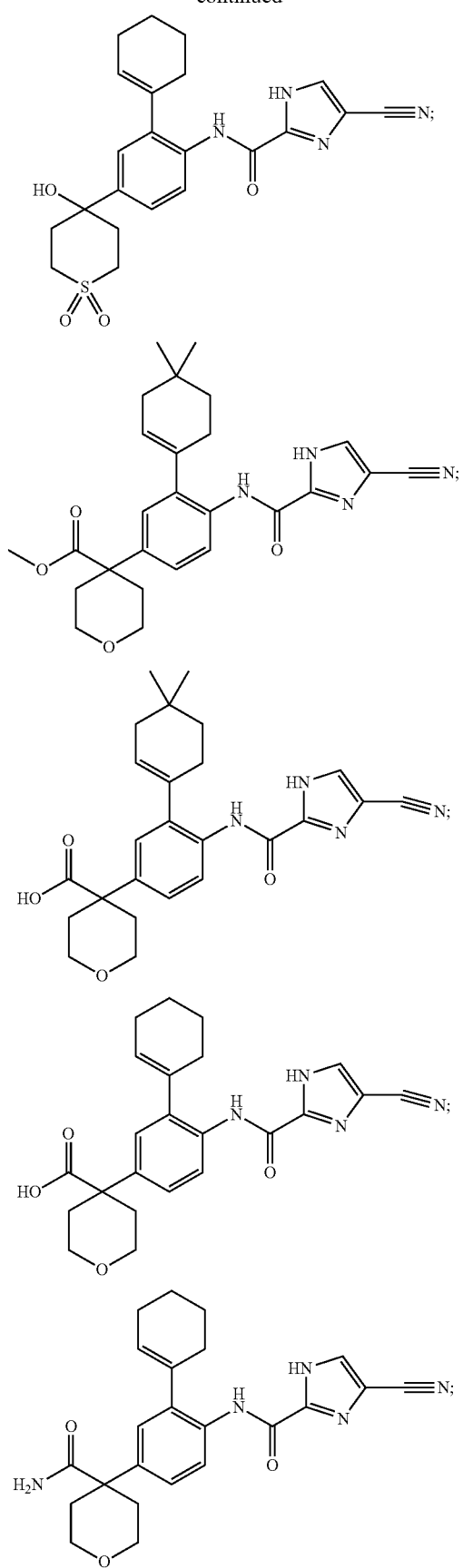
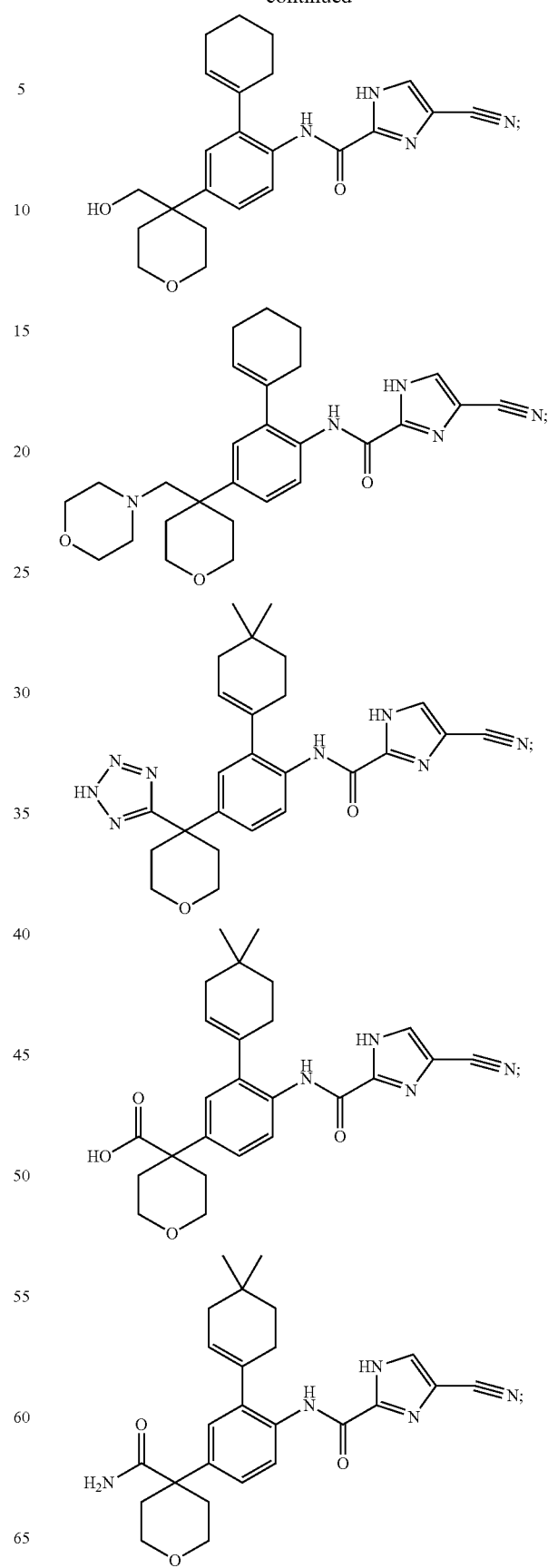

-continued
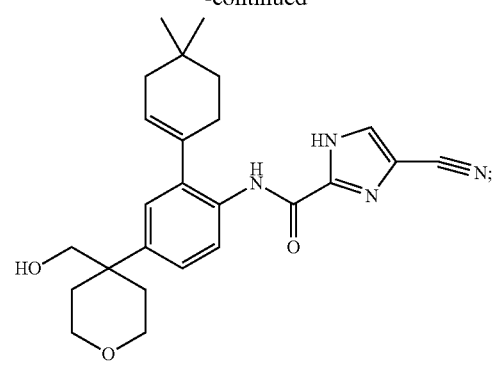
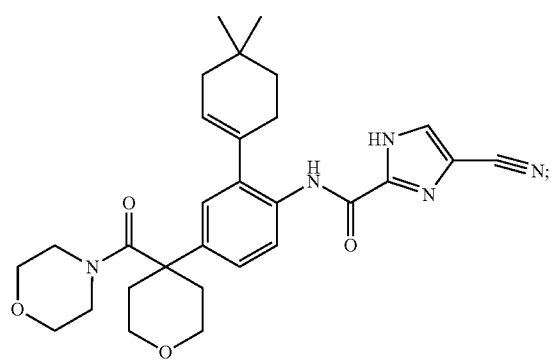
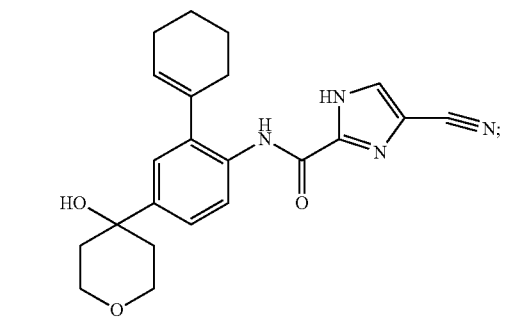
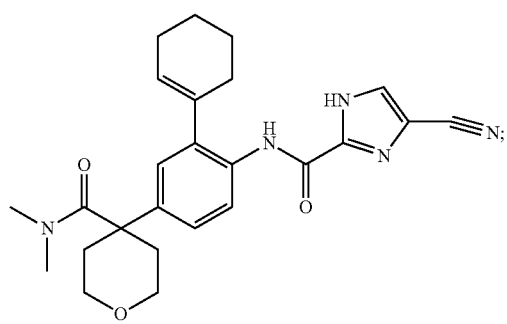
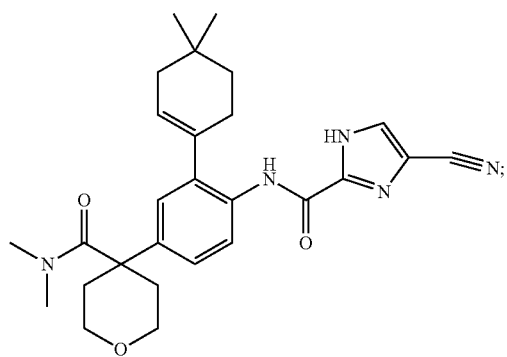
-continued
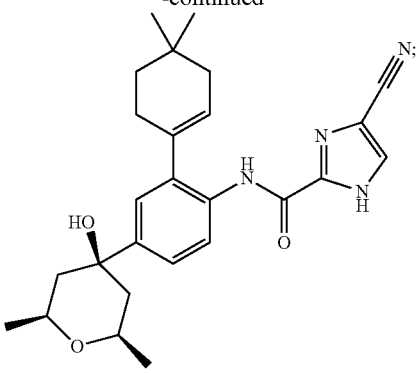
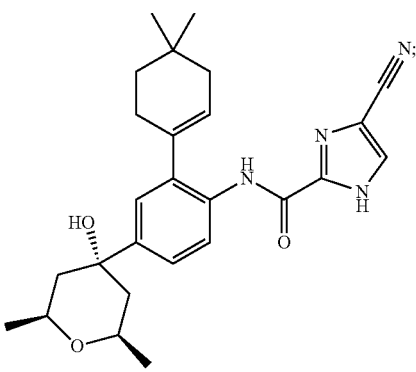
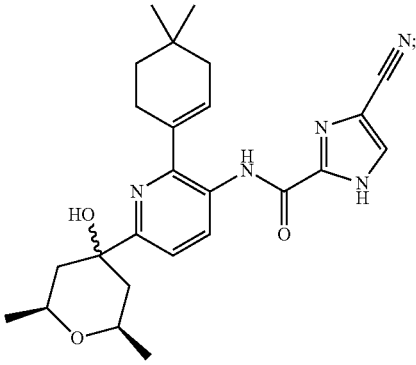
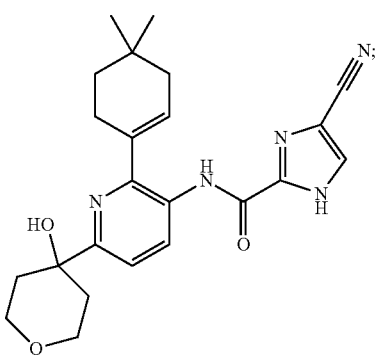

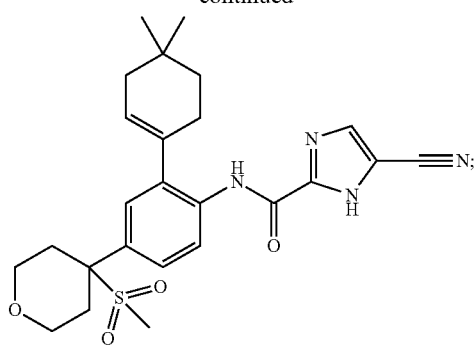
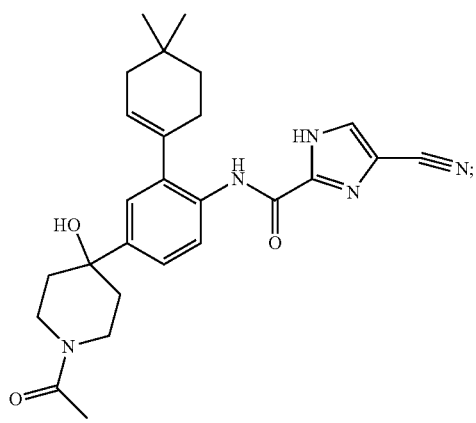 [SMILES: CC(=O)N1CCC(O)(c2ccc(NC(=O)c3nc(C#N)c[nH]3)c(C3=CCC(C)(C)CC3)c2)CC1]
and solvates, hydrates, tautomers and pharmaceutically acceptable salts thereof.
Another embodiment of the invention is a compound selected from the group consisting of:
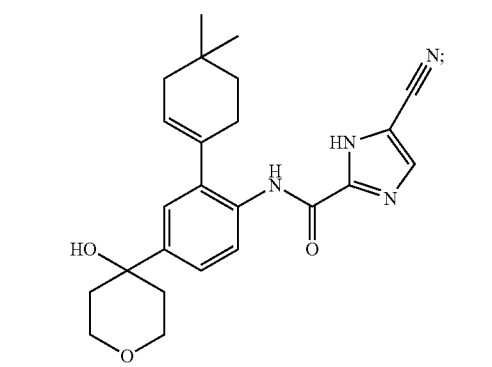
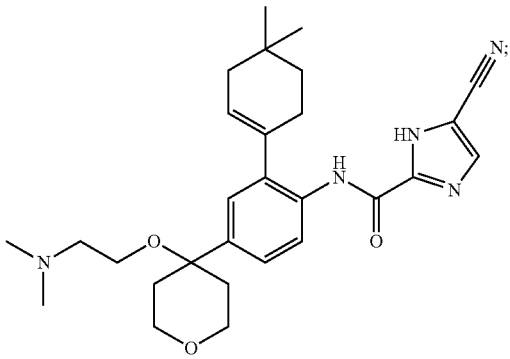
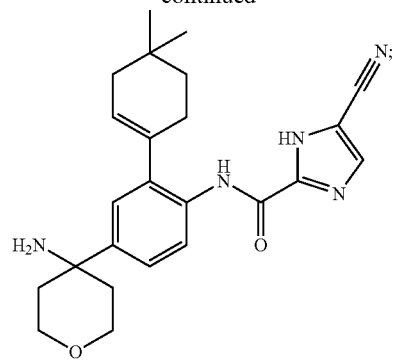
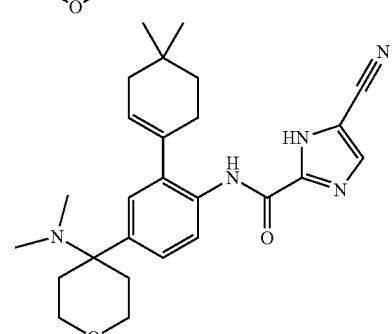
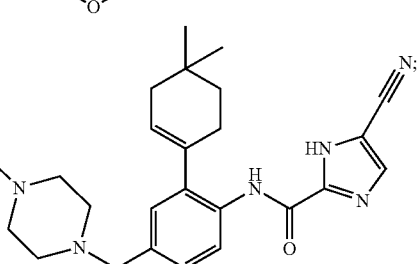
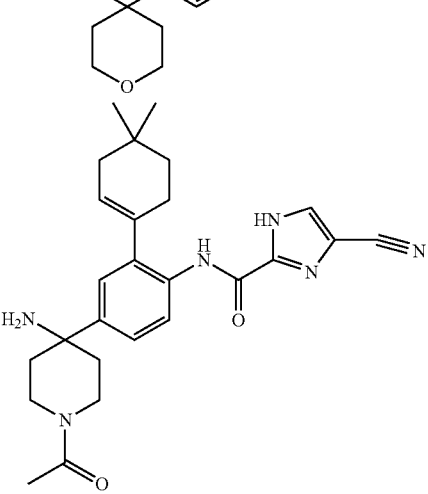
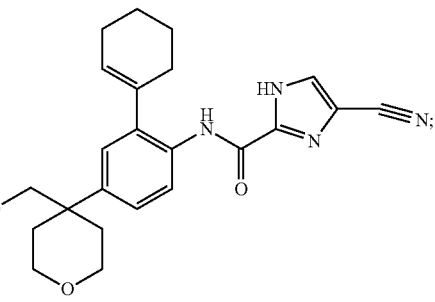

31
-continued
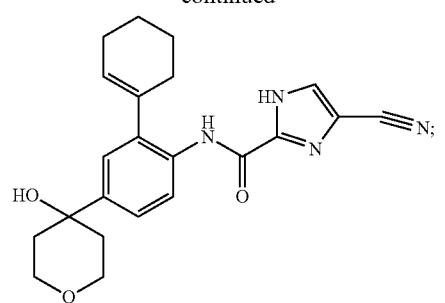
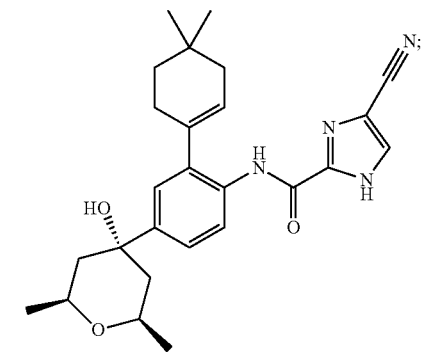
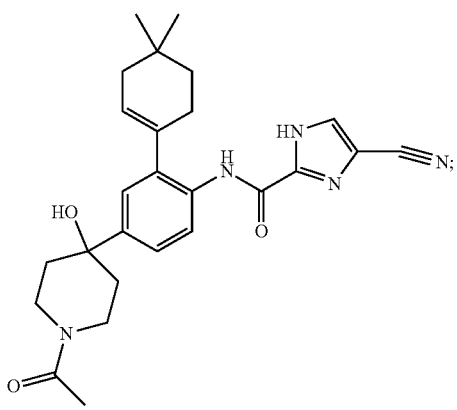 [SMILES: CC(=O)N1CCC(O)(c2ccc(NC(=O)c3nc(C#N)c[nH]3)c(C3=CCC(C)(C)CC3)c2)CC1]
and solvates, hydrates, tautomers and pharmaceutically acceptable salts thereof.
Another embodiment of the invention is a compound selected from the group consisting of:
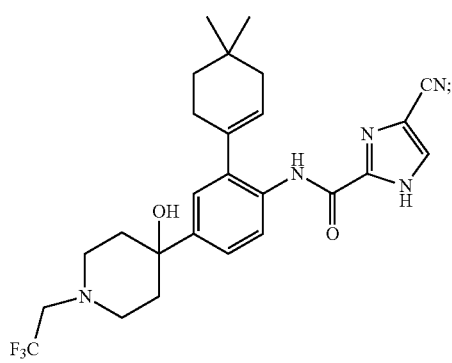
32
-continued
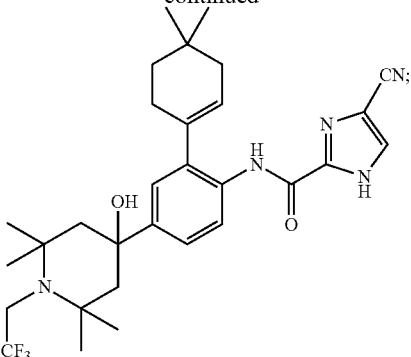
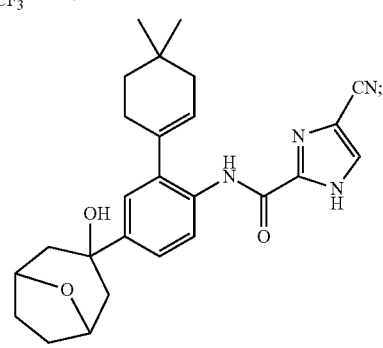
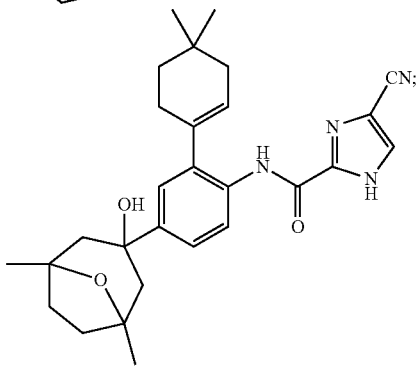
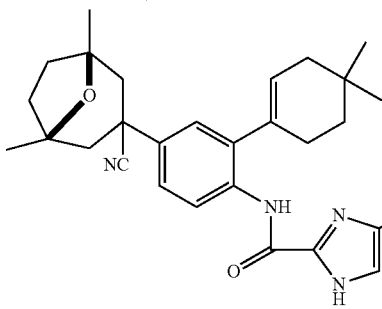
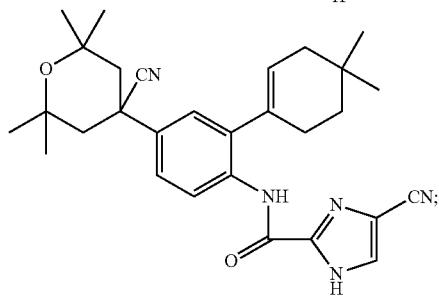
and solvates, hydrates, tautomers, and pharmaceutically acceptable salts thereof.

The invention also relates to methods of inhibiting protein tyrosine kinase activity in a mammal by administration of a therapeutically effective amount of at least one compound of Formula I. A preferred tyrosine kinase is c-fms.

The invention is considered to include the enantiomeric, diastereomeric and tautomeric forms of all compounds of Formula I as well as their racemic mixtures. In addition, some of the compounds represented by Formulae I may be prodrugs, i.e., derivatives of an acting drug that possess superior delivery capabilities and therapeutic value as compared to the acting drug. Prodrugs are transformed into active drugs by in vivo enzymatic or chemical processes.

I. DEFINITIONS

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "cycloalkyl" refers to a saturated or partially unsaturated ring composed of from 3 to 8 carbon atoms. Up to four alkyl substituents may optionally be present on the ring. Examples include cyclopropyl, 1,1-dimethyl cyclobutyl, 1,2,3-trimethylcyclopentyl, cyclohexyl, cyclopentenyl, cyclohexenyl, and 4,4-dimethyl cyclohexenyl.

The term "alkylamino" refers to an amino with one alkyl substituent, wherein the amino group is the point of attachment to the rest of the molecule.

The term "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "spiro-substituted cycloalkenyl" refers to a pair of cycloalkyl rings that share a single carbon atom and wherein at least one of the rings is partially unsaturated, for example:

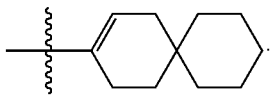

II. THERAPEUTIC USES

The compounds of Formula I represent novel potent inhibitors of protein tyrosine kinases, such as c-fms, and may be useful in the prevention and treatment of disorders resulting from actions of these kinases.

The invention also provides methods of inhibiting a protein tyrosine kinase comprising contacting the protein tyrosine kinase with an effective inhibitory amount of at least one of the compounds of Formula I. A preferred tyrosine kinase is c-fms. The compounds of the present invention are also inhibitors of FLT3 tyrosine kinase activity. In one embodiment of inhibiting a protein tyrosine kinase, at least one of the compounds of Formula I is combined with a known tyrosine kinase inhibitor.

In various embodiments of the invention, the protein tyrosine kinases inhibited by the compounds of Formula I are located in cells, in a mammal or in vitro. In the case of mammals, which includes humans, a therapeutically effective amount of a pharmaceutically acceptable form of at least one of the compounds of Formula I is administered.

The invention further provides methods of treating cancer in mammals, including humans, by administration of a therapeutically effective amount of a pharmaceutically acceptable composition of least one compound of Formula I. Exemplary cancers include, but are not limited to, acute myeloid leukemia, acute lymphocytic leukemia, ovarian cancer, uterine cancer, prostate cancer, lung cancer, breast cancer, colon cancer, stomach cancer, and hairy cell leukemia. The invention also provides methods of treating certain precancerous lesions including myelofibrosis. In one embodiment of the invention, an effective amount of at least one compound of Formula I is administered in combination with an effective amount of a chemotherapeutic agent.

The invention further provides methods of treating and of preventing metastasis arising from cancers that include, but are not limited to, ovarian cancer, uterine cancer, prostate cancer, lung cancer, breast cancer, colon cancer, stomach cancer, and hairy cell leukemia.

The invention further provides methods for the treatment osteoporosis, Paget's disease, and other diseases in which bone resorption mediates morbidity including rheumatoid arthritis and other forms of inflammatory arthritis, osteoarthritis, prosthesis failure, osteolytic sarcoma, myeloma, and tumor metastasis to bone as occurs frequently in cancers including, but not limited to, breast cancer, prostate cancer, and colon cancer.

The invention also provides methods of treating pain, in particular skeletal pain caused by tumor metastasis or osteoarthritis, as well as visceral, inflammatory, and neurogenic pain.

The invention also provides methods of treating cardiovascular, inflammatory, and autoimmune diseases in mammals, including humans, by administration of a therapeutically effective amount of a pharmaceutically acceptable form of at least one of the compounds of Formula I. Examples of diseases with an inflammatory component include glomerulonephritis, inflammatory bowel disease, prosthesis failure, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia or Alzheimer's dementia. These may be effectively treated with compounds of this invention. Other diseases that may be effectively treated include, but are not limited to atherosclerosis and cardiac hypertrophy.

Autoimmune diseases such as systemic lupus erythematosus, rheumatoid arthritis, and other forms of inflammatory arthritis, psoriasis, Sjogren's syndrome, multiple sclerosis, or uveitis, can also be treated with compounds of this invention.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation, prevention, treatment, or the delay of the onset or progression of the symptoms of the disease or disorder being treated.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope solvates of the compounds of the present invention. Thus, in the methods of treatment of the present invention, the term "administering" shall encompass the means for treating, ameliorating or preventing a syndrome, disorder or disease described herein with the compounds of the present invention or a solvate thereof, which would obviously be included within the scope of the invention albeit not specifically disclosed.

Methods of Preparation

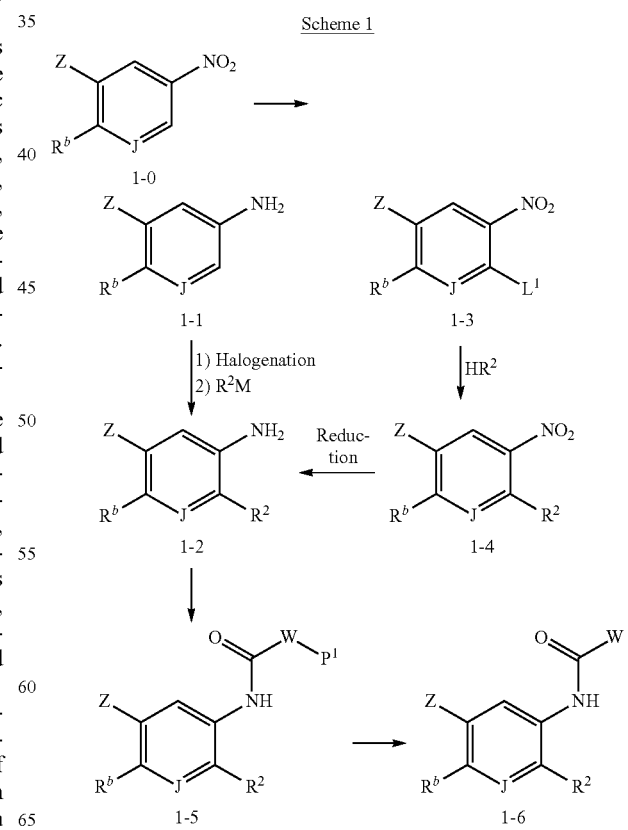

Scheme 1

Scheme 1 illustrates general methodology for the preparation of compounds of Formula I where $R^b$ is X (when X is available in starting material or prepared as shown in later schemes) or compounds of Formula 1-6 where $R^b$ is a leaving group (preferably bromo, chloro, or fluoro) that are useful intermediates used in later schemes. To illustrate the methodology of this scheme, reagents and conditions for the compounds where J is CH are defined. Those skilled in the art will recognize that where J is N, minor modifications of the reaction conditions and preferred reagents may be required.

Amines of Formula 1-1 may be commercially available or can be obtained from nitro compounds of Formula 1-0 by reduction using standard synthetic methodology (see Reductions in Organic Chemistry, M. Hudlicky, Wiley, New York, 1984). The preferred conditions are catalytic hydrogenation using a palladium catalyst in a suitable solvent such as methanol or ethanol. In cases where $R^b$ is a halogen and not available as amines of Formula 1-1, nitro reductions may be performed using iron or zinc in a suitable solvent such as acetic acid, or using iron and ammonium chloride in ethanol and water.

Compounds of Formula 1-2 where $R^2$ is cycloalkyl can be obtained by ortho-halogenation, preferably bromination, of amino compounds of Formula 1-1 followed by metal-catalyzed coupling reactions with boronic acids or boronate esters (Suzuki reactions, where $R^2M$ is $R^2B(OH)_2$ or a boronic ester, see N. Miyaura and A. Suzuki, *Chem. Rev.,* 95:2457 (1995); A. Suzuki in Metal-Catalyzed Coupling Reactions, F. Deiderich, P. Stang, Eds., Wiley-VCH, Weinheim (1988)) or tin reagents (Stille reactions, where $R^2M$ is $R^2Sn(alkyl)_3$, see J. K. Stille, *Angew. Chem, Int. Ed. Engl.,* 25: 508-524 (1986)) on the intermediate halo compound. When $R^b$ is Br, an iodo can be introduced such that is reacts preferentially over the bromine in the metal-catalyzed coupling reactions (when J is CH, this compound is commercially available). Preferred conditions for the bromination of 1-1 are N-bromosuccinimide (NBS) in a suitable solvent such as N,N-dimethylformamide (DMF), dichloromethane (DCM) or acetonitrile. Metal-catalyzed couplings, preferably Suzuki reactions, can be performed according to standard methodology, preferably in the presence of a palladium catalyst such as tetrakis(triphenylphosphine)palladium(0) $(Pd(PPh_3)_4)$, an aqueous base such aq. $Na_2CO_3$, and a suitable solvent such as toluene, ethanol, 1,4-dioxane, dimethoxyethane (DME), or DMF.

Compounds of Formula 1-2 where $R^2$ is cycloalkylamino (for example, piperidino) can be obtained by nucleophilic aromatic substitution of leaving groups $L^1$ (preferably fluoro or chloro) from compounds of Formula 1-3 that are activated by the nitro group with cycloalkylamines ($R^2H$; for example, piperidine) in the presence of a suitable base such as $K_2CO_3$, N,N-diisopropylethylamine (DIEA) or $NEt_3$ to give compounds 1-4, followed by reduction of the nitro group as described above.

The amino group in compounds of Formula 1-2 can then be coupled with a heterocyclic acid $P^1$—WCOOH (or a corresponding salt thereof $P^1$—WCOOM$^2$, where $M^2$ is Li, Na or K) where $P^1$ is an optional protecting group (for example 2-(trimethylsilyl)ethoxymethyl (SEM) such as when W is imidazole, triazole, pyrrole, or benzimidazole) or where $P^1$ is not present such as when W is furan. (For a list of protecting groups for W, see Theodora W. Greene and Peter G. M. Wuts, Protective Groups in Organic Synthesis, John Wiley and Sons, Inc., NY (1991)). The coupling can be carried out according to standard procedures for amide bond formation (for a review, see: M. Bodansky and A. Bodansky, The Practice of Peptide Synthesis, Springer-Verlag, NY (1984)) or by reaction with acid chlorides $P^1$—WCOCl or activated esters $P^1$—WCO$_2$R$^q$ (where R$^q$ is a leaving group such as pentafluorophenyl or N-succinimide) to form compounds of Formula 1-5. The preferred reaction conditions for coupling with $P^1$—WCOOH or $P^1$—WCOOM$^2$ are: when W is a furan (optional protecting group $P^1$ not present), oxalyl chloride in dichloromethane (DCM) with DMF as a catalyst to form the acid chloride WCOCl and then coupling in the presence of a trialkylamine such as N,N-diisopropylethylamine (DIEA); when W is a pyrrole (optional protecting group $P^1$ not present), 1-(3-dimethylaminopropyl)-3-ethylcarbodiimide hydrochloride (EDCI) and 1-hydroxybenzotriazole (HOBt); and when W is an imidazole, pyrrole or benzimidazole (optional $P^1$ present) the preferred conditions are bromotripyrrolidinophosphonium hexafluorophosphate (PyBroP) and DIEA in a solvent such as DCM or DMF.

When W in compounds of Formula 1-5 contain an optional protecting group $P^1$ as mentioned previously, it can be removed at this point to give compounds of Formula 1-6. For example, when W is imidazole protected on nitrogen with a SEM group, the SEM group can be removed with either acidic reagents such as trifluoroacetic acid (TFA) or fluoride sources such as tetrabutylammonium fluoride (TBAF) (see Greene and Wuts above).

Finally it is understood that in compounds of Formula I (i.e., Formula 1-6 where $R^b$ is X) may be further derivatized. Examples of further derivatization, include, but are not limited to: when compounds of Formula I contain a cyano group, this group may be hydrolyzed to amides or acids under acidic or basic conditions; when compounds of Formula I contain an ester, the ester may be hydrolysed to the acid, and the acid may be converted to amides by the methods described above for amide bond formation. Amides may be converted to amines by a Curtius or Schmidt reaction (for review see, *Angew. Chemie Int. Ed.,* 44(33), 5188-5240, (2005)) or amines may be obtained by reduction of cyano groups (*Synthesis,* 12, 995-6, (1988) and *Chem. Pharm. Bull.,* 38(8), 2097-101, (1990)). Acids may be reduced to alcohols, and alcohols may be oxidized to aldehydes and ketones. The preferred conditions for the reduction of a carboxylic acid in the presence of a cyano group include sodium borohydride and ethyl chloroformate in tetrahydrofuran (THF); and alcohol oxidation can be performed using the Dess-Martin periodinane reagent (*Adv. Syn. Catalysis,* 346, 111-124 (2004)). Aldehydes and ketones may be reacted with primary or secondary amines in the presence of a reducing agent such as sodium triacetoxyborohydride (see *J. Org. Chem.,* 61, 3849-3862, (1996)) to give amines by reductive amination. Olefins may be reduced by catalytic hydrogenation. When compounds of Formula I contain a sulfide, either acyclic or cyclic, the sulfide can be further oxidized to the corresponding sulfoxides or sulfones. Sulfoxides can be obtained by oxidation using an appropriate oxidant such as one equivalent of meta-chloroperbenzoic acid (MCPBA) or by treatment with $NaIO_4$ (see, for example, *J. Med. Chem.,* 46: 4676-86 (2003)) and sulfones can be obtained using two equivalents of MCPBA or by treatment with 4-methylmorpholine N-oxide and catalytic osmium tetroxide (see, for example, PCT application WO 01/47919). Also, both sulfoxides and sulfones can be prepared by using one equivalent and two equivalents of $H_2O_2$ respectively, in the presence of titanium (IV) isopropoxide (see, for example, *J. Chem. Soc., Perkin Trans.* 2, 1039-1051 (2002)).

Scheme 2

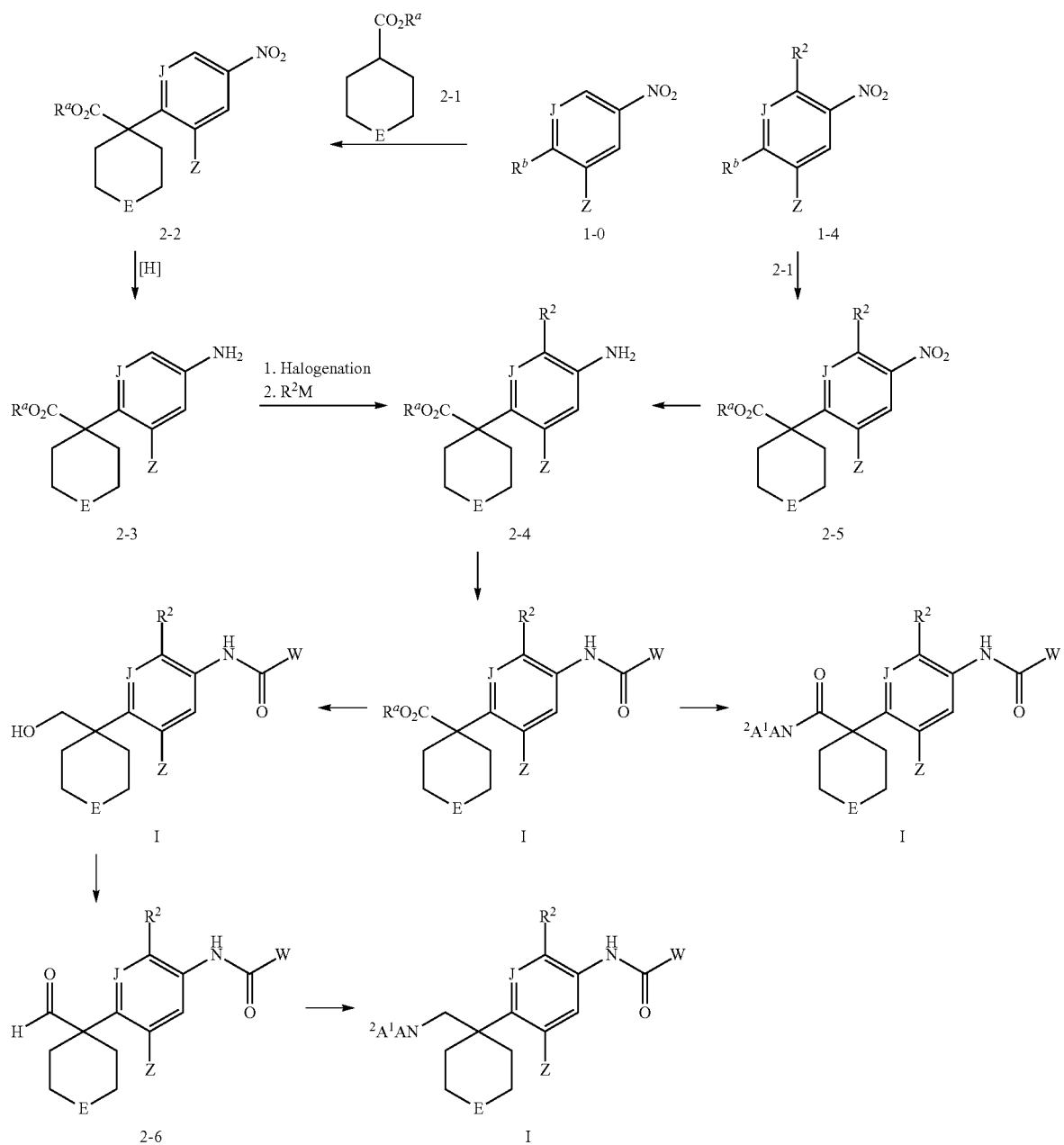

Scheme 2 illustrates general methodology for the preparation of compounds of Formula I where X is

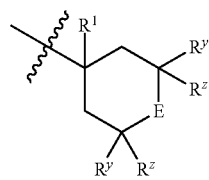

where, $R^y$ and $R^z$ are H, $C_{(1-4)}$alkyl or $OR^a$; E is O, $NR^3$, S, or $SO_2$; and $R^1$ is $CO_2R^a$, $CH_2OH$, $C(O)NA^1A^2$ and $CH_2NA^1A^2$.

For the illustration of synthetic strategy in this scheme, reagents and conditions are defined for the substrate where $R^y$ is $R^z$ is H is used in this scheme. Those skilled in the art will recognize that the chemistry is applicable to all X, $R^y$ and $R^z$ mentioned with little or minor modifications to reagents and conditions. In addition, although reagents and conditions are defined for the substrate where J is CH, as previously mentioned in Scheme 1, it is also understood that similar synthetic methods can be utilized with minor modifications when J is N.

When $R^2$ in Formula I is cycloalkyl (including cycloalkenyl), the sequence begins with compound 2-2 which can be obtained by initial treatment of the ester 2-1 ($R^a$ is $C_{(1-4)}$alkyl) with a suitable base such as lithium hexamethyldidilylamide (LHMDS) or preferably lithium diisopropylamide (LDA), followed by nucleophilic aromatic substitution of the leaving group $R^b$ (preferably fluoro or chloro) in the 4-halonitrophenyl compound 1-0 (as prepared in Scheme 1) with the resulting anion intermediate.

2-3 can be obtained from nitro compounds 2-2 by reduction using standard synthetic methodology (see Reductions in Organic Chemistry, M. Hudlicky, Wiley, New York, 1984). The preferred conditions are catalytic hydrogenation using a palladium catalyst in a suitable solvent such as methanol or ethanol.

Compound 2-4 can be obtained by ortho-halogenation, preferably bromination, of amino compound 2-4 followed by metal-catalyzed coupling reactions with boronic acid or boronate ester (Suzuki reactions, where $R^2M$ is $R^2B(OH)_2$ or a boronic ester) or tin reagent (Stille reactions, where $R^2M$ is $R^2Sn(alkyl)_3$) on the intermediate halo compound as described in Scheme 1.

When $R^2$ in Formula I is cycloalkylamino (for example, piperidino), an alternative method to prepare compound 2-4 begins with starting material 1-4 as described in Scheme 1 where $R^b$ is preferably chloro or fluoro. Compound 2-5 can be obtained from 1-4 and 2-1 by the same method as described for the conversion of compound 1-0 to compound 2-2. Compound 2-4 can then be obtained from compound 2-5 by reduction of the nitro group using standard synthetic methodology as described in Scheme 1 for the conversion of compound 1-0 to compound 1-1.

The compounds of Formula I where $R^1$ is an ester ($R^a$ is $C_{(1-4)}$alkyl) can be obtained from 2-4 by initial coupling with carboxylic acids $P^1$—WCOOH, followed by removal of the optional protecting group $P^1$ according to the procedures as described in Scheme 1 for the conversion of 1-2 to 1-6.

These compounds of Formula I where $R^1$ is an ester ($R^a$ is $C_{(1-4)}$alkyl) can be further hydrolyzed by an appropriate metal hydroxide reagent such as sodium hydroxide to give compounds of Formula I where $R^1$ is an acid ($R^a$ is H).

The compounds of Formula I where $R^1$ is an amide ($R^1$ is $C(O)NA^1A^2$) can be obtained from the compounds of Formula I where $R^1$ is an acid ($R^a$ is H) by initial treatment with an alkyl chloroformate, such as ethyl chloroformate, followed by trapping of the intermediate activated acylcarbonate with a suitable primary or secondary amine ($HNA^1A^2$). Similarly, compounds of Formula I where $R^1$ is a hydroxymethyl group can be obtained by reaction of the same intermediate activated acylcarbonate with a suitable reducing reagent such as $NaBH_4$ (see, for example, Tetrahedron, 62(4), 647-651; (2006)).

Compounds of Formula I where $R^1$ is a hydroxymethyl ($R^1$ is $CH_2OH$) can be further converted to the aldehyde 2-6 by oxidation reactions such as a Swern oxidation (J. Am. Chem. Soc. 102, 1390 (1980)) or preferably a Dess-Martin periodinane oxidation (see, for example, Tetrahedron Lett., 29, 995 (1988); J. Org. Chem., 55, 1636 (1990)).

Aldehyde 2-6 can be reacted with appropriate primary and secondary amines ($HNA^1A^2$) in the presence of suitable reducing reagents such as $NaBH_4$ or $NaBH_3CN$, or preferably $NaBH(OAc)_3$ according to standard procedures for reductive amination as described in Scheme 1, to form compounds of Formula I where $R^1$ is an aminomethyl group ($R^1$ is $CH_2NA^1A^2$).

It is understood that functional groups of compounds in this scheme can be further derivatized as outlined in Scheme 1.

Scheme 3

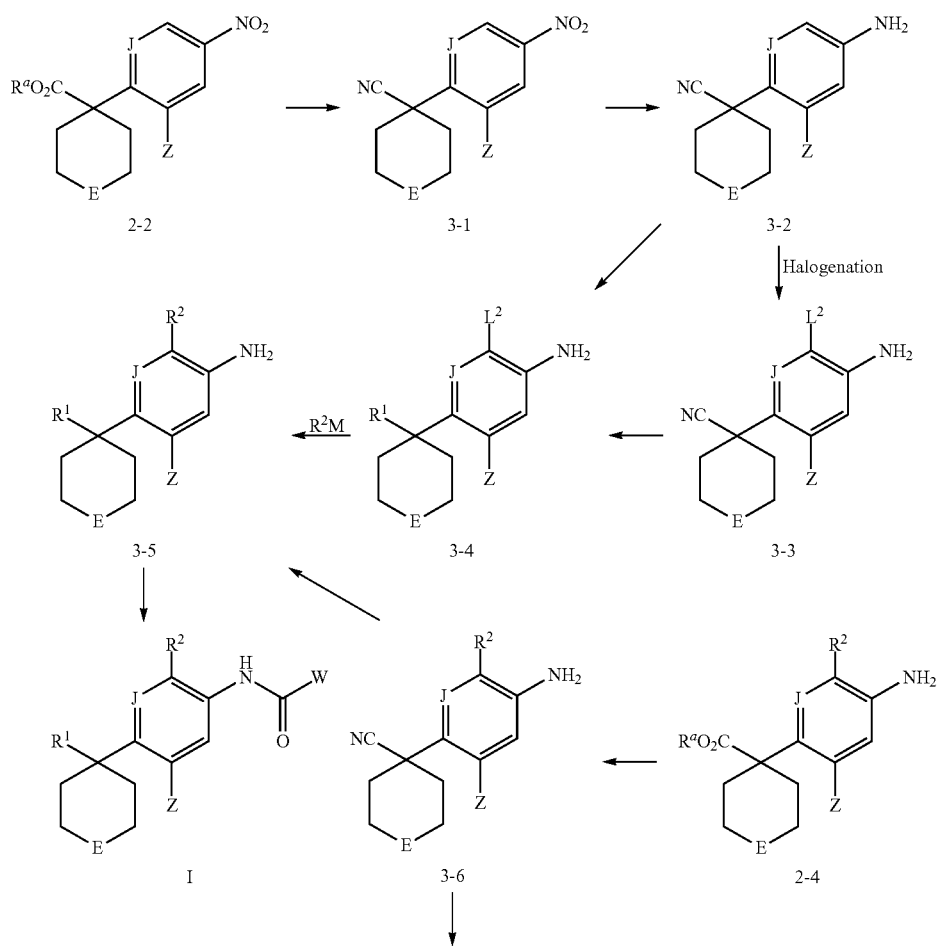

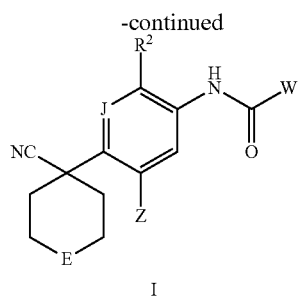

I

Scheme 3 illustrates general methodology for the preparation of compounds of Formula I where X is

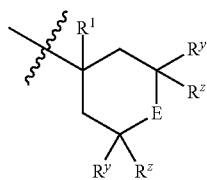

where $R^y$ and $R^z$ are H, $C_{(1-4)}$alkyl or $OR^a$; E is O, $NR^3$, S, or $SO_2$; and $R^1$ is —CN or heteroaryl.

For the illustration of synthetic strategy in this scheme, reagents and conditions are defined for the substrate where $R^y$ is $R^z$ is H is used in this scheme. Those skilled in the art will recognize that the chemistry is applicable to all X, $R^y$ and $R^z$ mentioned with little or minor modifications to reagents and conditions. In addition, although reagents and conditions are defined for the substrate where J is CH, as previously mentioned in Scheme 1, it is also understood that similar synthetic methods can be utilized with minor modifications when J is N.

The ester 2-2 ($R^a$ is $C_{(1-4)}$alkyl) can be hydrolyzed by an appropriate metal hydroxide reagent such as sodium hydroxide to give acid 2-2 ($R^a$ is H). The acid 2-2 can be converted to nitrile 3-1 by standard procedures which, in general, begin with activation of the acid, transformation into an amide or hydroxamate followed by dehydration (see, for example, J. Med. Chem., 33(10), 2828-41; (1990)), or preferably in one step by treatment with sulfonamide and thionyl chloride in a suitable solvent such as sulfolane (see, Tetrahedron Lett., 23(14), 1505-08; (1982)). Compound 3-2 can obtained from 3-1 by standard reduction procedures, preferably catalytic hydrogenation as described in Scheme 1.

The compound 3-3 ($L^2$ is halogen) can be obtained by ortho-halogenation, preferably bromination, of amine 3-2. Preferred conditions for the bromination of 3-2 are N-bromosuccinimide (NBS) in a suitable solvent such as N,N-dimethylformamide (DMF), dichloromethane (DCM) or acetonitrile.

At this point the cyano group in 3-3 can be converted to an unsaturated heterocycle in 3-4 by [2+3]cycloaddition with a 1,3 dipole or [2+4]cycloaddition with a diene or heterodiene as illustrated in Scheme 3a. The various heterocycles that can be produced are shown in Table 1 using the conditions in the references provided in the table.

When the unsaturated heterocycle present is unreactive toward halogenation, an alternative route to 3-4 involves treatment of nitrile 3-2 as just described to first form the unsaturated heterocycle followed by halogenation to introduce $L^2$ in 3-4. Compound 3-5 can be obtained by metal-catalyzed coupling reactions of 3-4 with boronic acids or boronate esters (Suzuki reactions, where $R^2M$ is $R^2B(OH)_2$ or a boronic ester) or tin reagents (Stille reactions, where $R^2M$ is $R^2Sn(alkyl)_3$). The metal-catalyzed couplings, preferably Suzuki reactions, can be performed according to standard methodology as described in Scheme 1.

When $R^2$ in Formula I is cycloalkylamino (for example, piperidino), an alternative method to prepare compound 3-5 begins with starting material 2-4 as prepared in Scheme 2. The ester 2-4 ($R^a$ is $C_{(1-4)}$alkyl) can be hydrolyzed by an appropriate metal hydroxide reagent such as sodium hydroxide to give acid 2-4 ($R^a$ is H). The acid 2-4 can be converted to nitrile 3-6 according to the procedures as described for the conversion of 2-2 to 3-1. Compound 3-6 can be converted to compound 3-5 according to the methods as described for the conversion of 3-3 to 3-4.

The compounds of Formula I where $R^1$ is a nitrile ($R^1$ is CN) can be obtained from 3-6 by initial coupling with carboxylic acids $P^1$—WCOOH, followed by removal of the optional protecting group $P^1$ according to the procedures as described in Scheme 1 for the conversion of 1-2 to 1-6.

Similarly, the compounds of Formula I where $R^1$ is an unsaturated heterocycle can be obtained from 3-5 in two steps, namely coupling with a carboxylic acid $P^1$—WCOOH followed by removal of the optional protection group, as described in Scheme 1 for the conversion of 1-2 to 1-6.

It is understood that functional groups of compounds in this scheme can be further derivatized as outlined in Scheme 1.

Scheme 3a

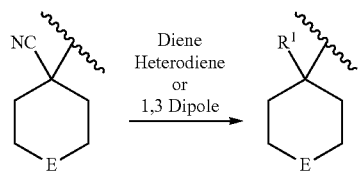

TABLE 1

| Number | Name | R¹ Structure | Reference: |
|---|---|---|---|
| 1 | Imidazole | | U.S. patent application 2005101785 |
| 2 | Thiazole | | *J. Med. Chem.*, 48(6), 2167-2175; (2005) |
| 3 | 4H-[1,2,4]Oxadiazol-5-one | | *Bioorganic & Medicinal Chemistry*, 13(6), 1989-2007 (2005) |
| 4 | 4H-Pyrrolo[2,3-b]pyrazine | | *Journal of Medicinal Chemistry*, 46(2), 222-236; (2003) |
| 5 | Pyridine | | *Journal of Organic Chemistry*, 67(13), 4414-4422; (2002) |
| 6 | [1,3,4]Oxadiazole | | *Journal of Labelled Compounds and Radiopharmaceuticals*, 16(5), 753-9; (1979) |
| 7 | 4H-[1,2,4]Triazole | | *Bioorganic & Medicinal Chemistry Letters*, 13(24), 4361-4364; (2003) |
| 8 | Tetrazole | | *Eur. Pat. Appl.*, 648759 |
| 9 | Pyrazole | | *Journal of Organic Chemistry*, 54(3), 635-40; (1989) |
| 10 | [1,3,5]Triazine | | *Khimiko-Farmatsevticheskii Zhurnal*, 22(12), 1469-75; (1988) |

TABLE 1-continued

| Number | Name | R¹ Structure | Reference: |
|---|---|---|---|
| 11 | [1,3,4]Thiadiazole | | Ger. Offen., 102004009933 |

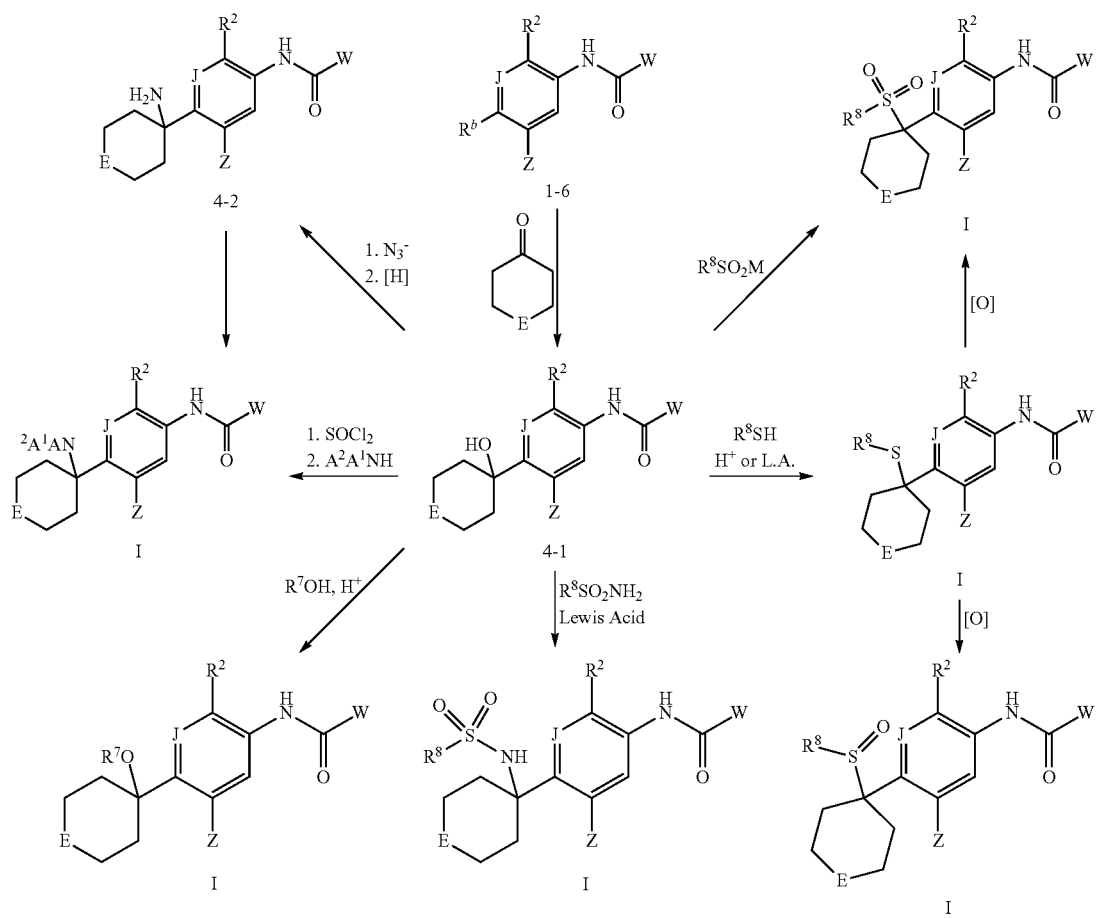

Scheme 4 describes the synthesis of compounds of Formula I where X is

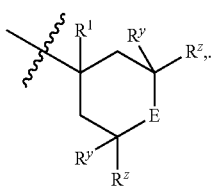

For the purpose of illustrating the methodology, reagents and conditions are defined in this scheme for the substrates where $R^y$ and $R^z$ are H; E is O, $NR^3$, S, or $SO_2$; and J is CH. Those skilled in the art will recognize that the chemistry is applicable to all X, $R^y$, $R^z$, and J referenced above can be utilized with minor modifications to the reagents and conditions.

The starting material, compound 1-6 where $R^b$ is halogen, preferably Br, is obtained as described in Scheme 1. The halo compound 1-6 can be converted to alcohol 4-1 by initial deprotonation with a suitable base, such as isopropylmagnesium chloride (i-PrMgCl), followed by lithium-halogen exchange with an appropriate lithium reagent such as n-butyllithium or preferably tert-butyllithium, and then trapping of the organo-lithium intermediate with an appropriate ketone. Compounds 4-1 is both a compound of Formula I, and can serve as a useful intermediate for the synthesis of other compounds with different groups for $R^1$.

The tertiary hydroxyl group in compound 4-1 can also be converted to an amino group in compound I ($R^1$ is $NA^1A^2$) by activating 4-1 with a reagent such as thionyl chloride (SOCl$_2$) and trapping of the resulting intermediate(s) with a primary or secondary amine (A$^2$A$^1$NH).

Compounds of Formula I where R$^1$ is alkoxy (OR$^7$) can be obtained from the hydroxyl compound 4-1 by treatment with acidic reagents such as sulfuric acid or preferably trifluoroacetic acid (TFA) and then trapping of the resulting tertiary cation with an alcohol R$^7$OH (where R$^7$ is CH$_2$CH$_2$NA$^1$A$^2$ or CH$_2$CH$_2$OR$^a$ where A$^1$, A$^2$ or R$^a$ are not H).

The hydroxyl compound 4-1 can also be reacted with a sulfonamide R$^8$SO$_2$NR$^a$H in the presence of a Lewis acid (L.A.) such as boron trifluoride diethyl etherate (BF$_3$.OEt$_2$) in a suitable solvent, such as THF to afford compound I (R$^1$ is NHSO$_2$R$^8$ where R$^8$ is CH$_2$CH$_2$NA$^1$A$^2$ or R$^a$ where A$^1$, A$^2$ or R$^a$ are not H).

Compounds of Formula I where R$^1$ is a sulfide (R$^1$ is SR$^8$) can be obtained from compound 4-1 by treatment with acidic reagents such as TFA or Lewis acids such as BF$_3$.OEt$_2$ and then trapping of the resulting tertiary cation with a thiol R$^8$SH (where R$^8$ is CH$_2$CH$_2$NA$^1$A$^2$ or R$^a$).

Compounds of Formula I where R$^1$ is a sulfide (R$^1$ is SR$^8$) can be further oxidized to the corresponding sulfoxide (Formula I where R$^1$ is SOR$^8$) or sulfone (Formula I where R1 is SO$_2$R$^8$) according to the sulfide oxidation procedures as described in Scheme 1.

Compounds of Formula I where R$^1$ is a sulfone can also be obtained directly from compound 4-1 by reaction with a metal sulfinate salt R$^8$SO$_2$M (where M is Na, or K) (see, for example, B. Koutek, et al, *Synth. Commun.*, 6 (4), 305-8 (1976)).

Compounds of Formula I where X is

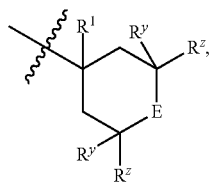

and R$^1$ is H can be obtained from the corresponding compounds where R$^1$ is OH by a deoxygenation reaction according to literature procedures (see, for example: Dolan, S., et al, *J. Chem., Soc., Chem. Commun.*, 1588-9 (1985), WO patent 98/06700 and Wustrow, D., et al, Tetrahedron Lett., 35, 61-4 (1994)).

It is understood that functional groups in this scheme can be further derivatized as outlined in Scheme 1. For example, the amino group in compound 4-2 can be reacted with various electrophiles. The amino group can be reacted with carboxylic acids according to standard procedures for amide bond formation or by reaction with acid chlorides or activated esters to form amide compounds as described in Scheme 1. It can be also reacted with an appropriate carbonylation agent, such as phosgene, carbonyldiimidazole or preferably triphosgene, in the presence of a base, such as pyridine or DIEA. The intermediate thus formed can be trapped with a primary or secondary amine, to afford the corresponding urea compound. Similarly, the amino group in compound 4-2 can be reacted with an appropriate oxalylation agent, such as oxalyl chloride, in the presence of a base, such as pyridine or DIEA and the intermediate thus formed can be trapped with a primary or secondary amine to afford oxalamide compounds. Furthermore, the amino group can be reacted with appropriate aldehydes or ketones in the presence of suitable reducing reagents such as NaBH$_4$ or NaBH$_3$CN, or preferably NaBH(OAc)$_3$ according to standard procedures for reductive amination as described in Scheme 1, to form compounds of Formula I where R$^1$ is NA$^1$A$^2$.

Scheme 5

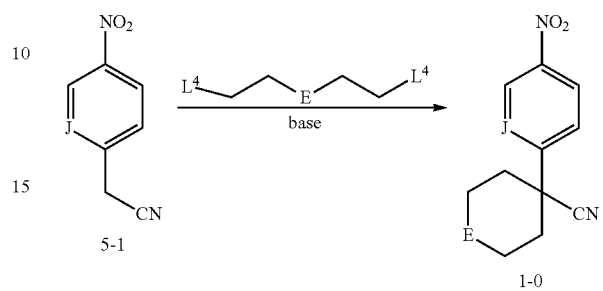

Scheme 5 describes the synthesis of useful intermediates of Formula 1-0 where X is

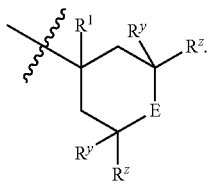

For the purpose of illustrating the methodology, R$^y$ and R$^z$ are H; and E is O, S, SO$_2$, or NR$_3$. Those skilled in the art will recognize that the chemistry is applicable to all X, R$^y$ and R$^z$ mentioned with only minor modifications to reagents and conditions. In addition, although reagents and conditions are defined for the substrates where J is CH, as previously mentioned in Scheme 1, it is also understood that similar synthetic methods can be utilized with minor modifications when J is N.

Scheme 6

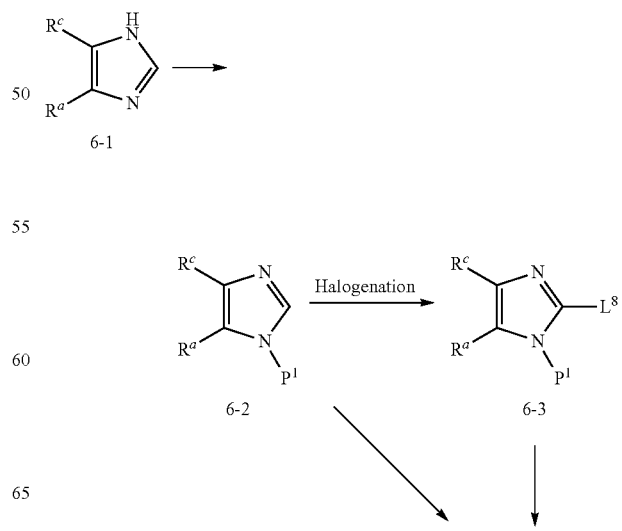

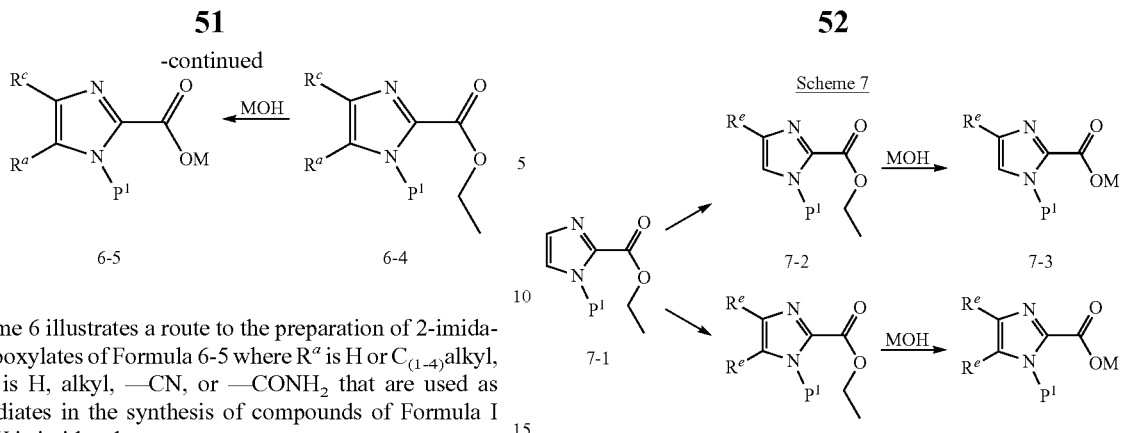

6-5                         6-4

Scheme 6 illustrates a route to the preparation of 2-imidazolecarboxylates of Formula 6-5 where $R^a$ is H or $C_{(1-4)}$alkyl, and $R^d$ is H, alkyl, —CN, or —CONH$_2$ that are used as intermediates in the synthesis of compounds of Formula I where W is imidazole.

Imidazoles of Formula 6-1 where $R^a$ is H or $C_{(1-4)}$alkyl, and $R^c$ is H, $C_{(1-4)}$alkyl or —CN are either commercially available or, in the case where $R^c$ is —CN, are readily available from commercially available aldehydes (6-1 where $R^c$ is CHO) by reaction with hydroxylamines followed by dehydration with a suitable reagent such as phosphorus oxychloride or acetic anhydride (*Synthesis*, 677, 2003). Imidazoles of Formula 6-1 are protected with a suitable group ($P^1$) such as a methoxymethylamine (MOM), or preferably a SEM group to give compounds of Formula 6-2 (see Theodora W. Greene and Peter G. M. Wuts, Protective Groups in Organic Synthesis, John Wiley and Sons, Inc., NY (1991)).

Imidazoles of Formula 6-2, where $R^c$ is —CN, are halogenated with a suitable reagent such as N-bromosuccinimide or N-iodosuccinimide under either electrophilic conditions in a solvent such as DCM or CH$_3$CN or under radical conditions in the presence of an initiator such as azobis(isobutyronitrile) (AIBN) in a solvent such as CCl$_4$ to give compounds of Formula 6-3 where $L^8$ is a leaving group (preferably bromo or iodo). Halogen-magnesium exchange on compounds of Formula 6-3 provides the organomagnesium species, which is then reacted with a suitable electrophile to provide compounds of Formula 6-4. The preferred conditions for halogen-magnesium exchange are using an alkyl-magnesium reagent, preferably isopropylmagnesium chloride in a suitable solvent such as THF at temperatures between −78° C.- to 0° C. The preferred electrophiles are ethyl chloroformate or ethyl cyanoformate. For examples of halogen-magnesium exchange on cyanoimidazoles see *J. Org. Chem.* 65, 4618, (2000).

For imidazoles of Formula 6-2, where $R^c$ is not —CN, these may be converted directly to imidazoles of Formula 6-4 by deprotonation with a suitable base such as an alkyllithium followed by reaction with an electrophile as described above for the organomagnesium species. The preferred conditions are treating the imidazole with n-butyllithium in THF at −78° C. and quenching the resulting organolithium species with ethyl chloroformate (for examples, see *Tetrahedron Lett.*, 29, 3411-3414, (1988)).

The esters of Formula 6-4 may then be hydrolyzed to carboxylic acids (M is H) or carboxylate salts (M is Li, Na, or K,) of Formula 6-5 using one equivalent of an aqueous metal hydroxide (MOH) solution, preferably potassium hydroxide in a suitable solvent such as ethanol or methanol. Synthesis of compounds of Formula 6-5 where $R^d$ is —CONH$_2$ is accomplished by first treating compounds of Formula 6-4 where $R^c$ is —CN with an appropriate alkoxide such as potassium ethoxide to convert the cyano group to an imidate group (Pinner reaction) followed by hydrolysis of both the ester and imidate groups with two equivalents of an aqueous metal hydroxide solution.

Scheme 7 illustrates a route to 2-imidazolecarboxylates of Formula 7-3 or 7-5 where $R^e$ is chloro or bromo, and M is H, Li, K, or Na that are used as intermediates in the synthesis of compounds of Formula I where W is imidazole.

Compounds of Formula 7-1 are first prepared by protection of commercially available ethyl imidazolecarboxylate according to the methods outlined in Scheme 6, preferably with a SEM group.

Compounds of Formula 7-2 are prepared by reaction of compounds of Formula 7-1 with one equivalent of an appropriate halogenating reagent, such as NBS or NCS in a suitable solvent such as CH$_3$CN, DCM or DMF at 25° C. Compounds of Formula 7-4 are prepared by reaction of compounds of Formula 7-1 with two equivalents of an appropriate halogenating reagent, such as NBS or NCS in a suitable solvent such as CH$_3$CN or DMF at temperatures between 30° C. to 80° C. Imidazoles of Formula 7-3 and 7-5 are then obtained from the respective esters by hydrolysis as described in Scheme 6.

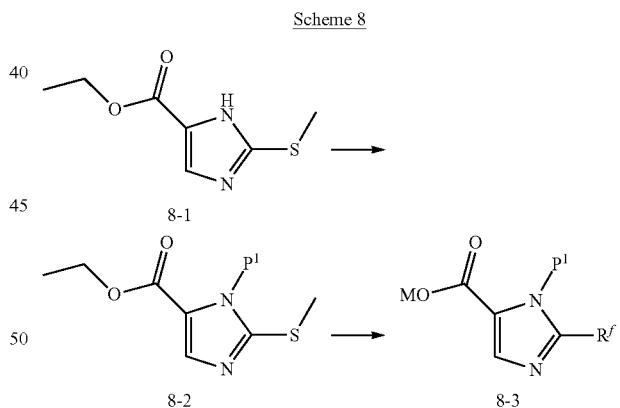

Scheme 8 illustrates a method for the preparation of imidazoles of Formula 8-3 where $R^f$ is —SCH$_3$, —SOCH$_3$, or —SO$_2$CH$_3$, M is H, Li, K, or Na that are used as intermediates in the synthesis of compounds of Formula I where W is imidazole.

Imidazole 8-1 (WO 1996011932) is protected according to the methods described in Scheme 6, preferably with a SEM protecting group to give compounds of Formula 8-2. Ester hydrolysis according to the procedure in Scheme 6 gives compounds of Formula 8-3 where $R^f$ is —SCH$_3$. Oxidation of 2-methylthioimidazoles of Formula 8-2 with one equivalent of an appropriate oxidant, followed by ester hydrolysis according to the procedure in Scheme 6 gives compounds of Formula 8-3 where $R^f$ is —SOCH$_3$. Oxidation with two equivalents of an appropriate oxidant, followed by ester hydrolysis according to the procedure in Scheme 6 gives compounds of Formula 8-3 where $R^f$ is —SO$_2$CH$_3$. The preferred reagent for oxidation is MCPBA in DCM. References for the conversion of sulfides to sulfoxides and sulfones are given in Scheme 1.

Example 1

5-Cyano-1H-imidazole-2-carboxylic acid [2-(4,4-dimethyl-cyclohex-1-enyl)-4-(4-hydroxy-tetrahydro-pyran-4-yl)-phenyl]-amide

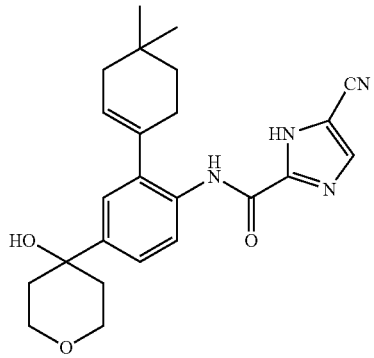 [SMILES: CC1(C)CC=C(c2cc(C3(O)CCOCC3)ccc2NC(=O)c2ncc(C#N)[nH]2)CC1]

a) 1-(2-Trimethylsilanyl-ethoxymethyl)-1H-imidazole-4-carbonitrile

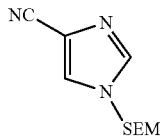 [SMILES: C[Si](C)(C)CCOCn1cnc(C#N)c1]

A flask charged with imidazole-4-carbonitrile (0.50 g, 5.2 mmol) (*Synthesis*, 677, 2003), 2-(trimethylsilyl)ethoxymethyl chloride (SEMCl) (0.95 mL, 5.3 mmol), K$_2$CO$_3$ (1.40 g, 10.4 mmol), and acetone (5 mL) was stirred for 10 h at RT. The mixture was diluted with EtOAc (20 mL), washed with water (20 mL), brine (20 mL) and the organic layer was dried over MgSO$_4$. The crude product was eluted from a 20-g SPE cartridge (silica) with 30% EtOAc/hexane to give 0.80 g (70%) of the title compound as a colorless oil. Mass spectrum (CI (CH$_4$), m/z): Calcd. for C$_{10}$H$_{17}$N$_3$OSi, 224.1 (M+H). found 224.1.

b) 2-Bromo-1-(2-trimethylsilanyl-ethoxymethyl)-1H-imidazole-4-carbonitrile

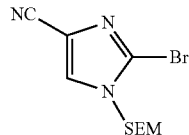

To a solution of 1-(2-trimethylsilanyl-ethoxymethyl)-1H-imidazole-4-carbonitrile (0.70 g, 3.1 mmol) (as prepared in the previous step) in CCl$_4$ (10 mL) was added N-bromosuccinimide (NBS) (0.61 g, 3.4 mmol) and azobis(isobutyronitrile) (AIBN) (cat), and the mixture was heated at 60° C. for 4 h. The reaction was diluted with EtOAc (30 mL), washed with NaHCO$_3$ (2×30 mL), brine (30 mL), the organic layer was dried over Na$_2$SO$_4$ and then concentrated. The title compound was eluted from a 20-g SPE cartridge (silica) with 30% EtOAc/hexane to give 0.73 g (77%) of a yellow solid. Mass spectrum (CI(CH$_4$), m/z): Calcd. for C$_{10}$H$_{16}$BrN$_3$OSi, 302.0/304.0 (M+H). found 302.1/304.1.

c) 4-Cyano-1-(2-trimethylsilanyl-ethoxymethyl)-1H-imidazole-2-carboxylic acid ethyl ester

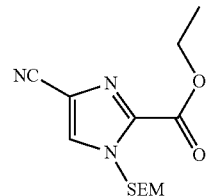 [SMILES: CCOC(=O)c1nc(C#N)cn1COCC[Si](C)(C)C]

To a solution of 2-bromo-1-(2-trimethylsilanyl-ethoxymethyl)-1H-imidazole-4-carbonitrile (0.55 g, 1.8 mmol) (as prepared in the previous step) in tetrahydrofuran (THF) (6 mL) at −40° C. was added dropwise a solution of 2 M i-PrMgCl in THF (1 mL). The reaction was allowed to stir for 10 min at −40° C. and then cooled to −78° C., and ethyl cyanoformate (0.30 g, 3.0 mmol) was added. The reaction was allowed to attain RT and stirred for 1 h. The reaction was quenched with satd aq NH$_4$Cl, diluted with EtOAc (20 mL), washed with brine (2×20 mL). The organic layer was dried over Na$_2$SO$_4$ and then concentrated. The title compound was eluted from a 20-g SPE cartridge (silica) with 30% EtOAc/hexane to give 0.40 g (74%) of a colorless oil. Mass spectrum (ESI, m/z): Calcd. for C$_{13}$H$_{21}$N$_3$O$_3$Si, 296.1 (M+H). found 296.1.

d) 4-Cyano-1-(2-trimethylsilanyl-ethoxymethyl)-1H-imidazole-2-carboxylate potassium salt

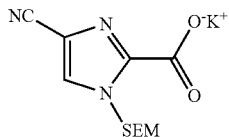

To a solution of 4-cyano-1-(2-trimethylsilanyl-ethoxymethyl)-1H-imidazole-2-carboxylic acid ethyl ester (0.40 g, 1.3 mmol) (as prepared in the previous step) in ethanol (3 mL) was added a solution of 6M KOH (0.2 mL, 1.2 mmol) and the reaction was stirred for 10 min and then concentrated to give 0.40 g (100%) of the title compound as a yellow solid. $^1$H-NMR (CD$_3$OD; 400 MHz) δ 7.98 (s, 1H), 5.92 (s, 2H), 3.62 (m, 2H), 0.94 (m, 2H), 0.00 (s, 9H). Mass spectrum (ESI-neg, m/z): Calcd. for $C_{11}H_{16}KN_3O_3Si$, 266.1 (M-K). found 266.0.

e) 4-Bromo-2-(4,4-dimethyl-cyclohex-1-enyl)-phenylamine

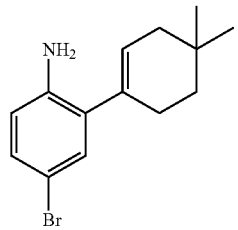 [SMILES: CC1(C)CC=C(c2cc(Br)ccc2N)CC1]

A flask is charged with 4-bromo-2-iodo-phenylamine (1.10 g, 3.70 mmol), 4,4-dimethylcyclohexen-1-ylboronic acid (0.630 g, 4.07 mmol), $Pd(PPh_3)_4$ (0.24 g, 5 mol %), 2 M $Na_2CO_3$ (16 mL), EtOH (16 mL) and toluene (32 mL) and heated at 80° C. for 6 h. The reaction was diluted with EtOAc (100 mL) and washed with saturated aqueous $NaHCO_3$ (2×100 mL) and brine (100 mL), and the organic layer dried over $Na_2SO_4$ and evaporated. The crude product was purified by flash silica gel chromatography eluting with 10% EtOAc/hexanes to give 0.680 g (66%) of the title compound as a light yellow oil. Mass spectrum (ESI, m/z): Calcd. for $C_{14}H_{18}BrN$, 280.1 (M+H). found 280.1.

f) 4-Cyano-1-(2-trimethylsilanyl-ethoxymethyl)-1H-imidazole-2-carboxylic acid [4-bromo-2-(4,4-dimethyl-cyclohex-1-enyl)-phenyl]-amide

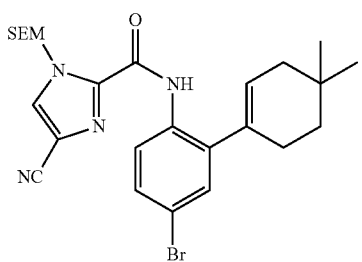 [SMILES: CC1(C)CC=C(c2cc(Br)ccc2NC(=O)c2nc(C#N)cn2COCC[Si](C)(C)C)CC1]

To a suspension of 4-bromo-2-(4,4-dimethyl-cyclohex-1-enyl)-phenylamine (0.640 g, 2.29 mmol) (prepared in the previous step) and 4-cyano-1-(2-trimethylsilanyl-ethoxymethyl)-1H-imidazole-2-carboxylate potassium salt (0.700 g, 2.30 mmol) (prepared in this example, step (d)) in DCM (12 mL) was added DIPEA (0.800 mL, 4.60 mmol) and PyBroP (1.29 g, 2.76 mmol) and the mixture allowed to stir at RT for 10 h. The mixture was diluted with DCM (50 mL) and washed with $NaHCO_3$ (2×50 mL) and the organic layer dried over $Na_2SO_4$ and concentrated. The title compound was eluted from a 20-g SPE with 1:1 DCM/hexanes to give 1.04 g (86%) of the title compound as a white solid. Mass spectrum (ESI, m/z): Calcd. for $C_{25}H_{33}BrN_4O_2Si$, 529.1 (M+H). found 529.1.

g) 4-Cyano-1H-imidazole-2-carboxylic acid [4-bromo-2-(4,4-dimethyl-cyclohex-1-enyl)-phenyl]-amide

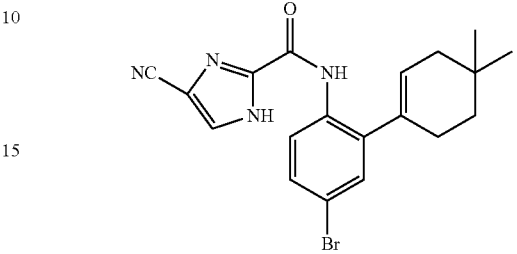

To a solution of 4-cyano-1-(2-trimethylsilanyl-ethoxymethyl)-1H-imidazole-2-carboxylic acid [4-bromo-2-(4,4-dimethyl-cyclohex-1-enyl)-phenyl]-amide (0.95 g, 1.80 mmol) (prepared in the previous step) in 10 mL of DCM was added 0.4 mL of EtOH and 10 mL of TFA and the mixture stirred for 1 h at RT. The mixture was concentrated and triturated with $Et_2O$ to give 0.68 g (95%) of a white solid: $^1$H-NMR (400 MHz, $CDCl_3$): δ 11.23 (br s, 1H), 9.52 (br s, 1H), 8.27 (d, J=8.7 Hz, 1H), 7.72 (s, 1H), 7.41 (dd, J=2.3, 8.7 Hz, 1H), 7.33 (d, J=2.3 Hz, 1H), 5.82 (m, 1H), 2.28 (m, 2H), 2.10 (m, 2H), 1.58 (m, 2H), 1.08 (s, 6H). Mass spectrum (ESI, m/z): Calcd. for $C_{19}H_{19}BrN_4O$, 399.1 (M+H). found 399.0.

h) 5-Cyano-1H-imidazole-2-carboxylic acid [2-(4,4-dimethyl-cyclohex-1-enyl)-4-(4-hydroxy-tetrahydro-pyran-4-yl)-phenyl]-amide To a suspension of 4-cyano-1H-imidazole-2-carboxylic acid [4-bromo-2-(4,4-dimethyl-cyclohex-1-enyl)-phenyl]-amide (0.550 g, 1.38 mmol) (prepared in the previous step) in 20 mL THF at −40° C. was added i-PrMgCl (1.40 mL, 2.80 mmol, 2 M in THF) and the solution was then warmed to 0° C. and stirred for 10 min. The solution was then cooled to −78° C. and t-BuLi (2.15 mL, 3.65 mmol, 1.7 M in pentane) was added dropwise over 5 min and then tetrahydro-pyran-4-one (0.650 mL, 7.05 mmol) was added immediately thereafter. After 5 min at −78° C. the reaction was quenched with satd $NH_4Cl$ (20 mL) and extracted with EtOAc (3×20 mL) and dried over $Na_2SO_4$. The title compound was purified by flash chromatography (Si gel) eluting with 50% EtOAc/DCM to give 0.460 g (79%) of a white solid. $^1$H-NMR (400 MHz, DMSO-$d_6$): δ 14.28 (s, 1H), 9.77 (s, 1H), 8.21 (s, 1H), 7.98 (d, J=8.5 Hz, 1H), 7.38 (dd, J=8.5, 2.2 Hz, 1H), 7.34 (d, J=2.2 Hz, 1H), 5.67 (m, 1H), 5.03 (s, 1H), 3.83-3.66 (m, 4H), 2.31-2.22 (m, 2H), 2.04-1.92 (m, 4H), 1.58-1.46 (m, 4H), 1.01 (s, 6H). Mass spectrum (ESI, m/z): calcd. for $C_{24}H_{28}N_4O_3$, 421.2 (M+H). found 421.1.

Example 2

5-Cyano-1H-imidazole-2-carboxylic acid [4-[4-(2-dimethylamino-ethoxy)-tetrahydro-pyran-4-yl]-2-(4,4-dimethyl-cyclohex-1-enyl)-phenyl]-amide trifluoroacetic acid salt

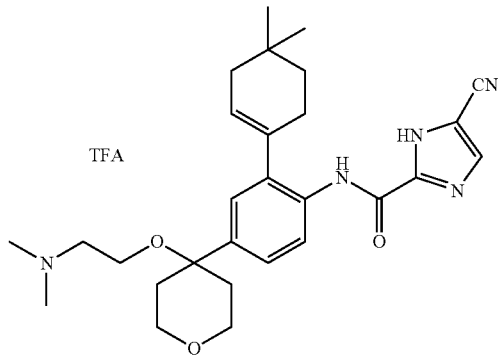 [SMILES: CN(C)CCOC1(c2ccc(NC(=O)c3ncc(C#N)[nH]3)c(C3=CCC(C)(C)CC3)c2)CCOCC1]

To a suspension of 5-cyano-1H-imidazole-2-carboxylic acid [2-(4,4-dimethyl-cyclohex-1-enyl)-4-(4-hydroxy-tetrahydro-pyran-4-yl)-phenyl]-amide (48.0 mg, 0.114 mmol) (prepared in Example 1, step (h)) in 1 mL of DCM was added 2-dimethylamino-ethanol (0.114 mL, 1.14 mmol), TFA (0.130 mL, 1.17 mmol), and the mixture heated to 50° C. for 8 h. The mixture was concentrated and the title compound purified by RP-HPLC on a C18 column eluting with a linear gradient of 30-50% CH$_3$CN in 0.1% TFA/H$_2$O over 12 min to give 14 mg (20%) of a white solid. $^1$H-NMR (400 MHz, CD$_3$OD): δ 8.21 (d, J=8.6 Hz, 1H), 7.91 (s, 1H), 7.35 (dd, J=8.6, 2.2 Hz, 1H), 7.21 (d, J=2.2 Hz, 1H), 5.67 (m, 1H), 3.83-3.66 (m, 4H), 3.30-3.15 (m, 4H), 2.76 (s, 6H), 2.26-2.20 (m, 2H), 2.12-1.94 (m, 6H), 1.51 (t, J=6.3 Hz, 2H), 1.00 (s, 6H). Mass spectrum (ESI, m/z): Calcd. for C$_{28}$H$_{37}$N$_5$O$_3$, 492.3 (M+H). found 492.0.

Example 3

{4-[4-[(5-Cyano-1H-imidazole-2-carbonyl)-amino]-3-(4,4-dimethyl-cyclohex-1-enyl)-phenyl]-tetrahydro-pyran-4-yloxy}-acetic acid

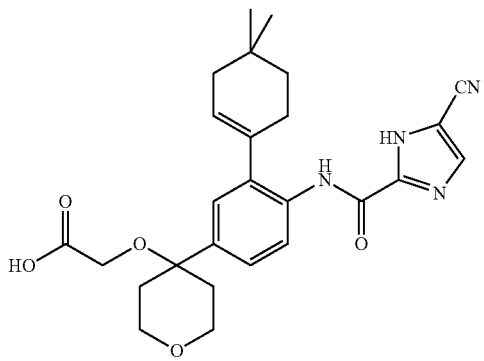 [SMILES: CC1(C)CC=C(c2cc(C3(OCC(=O)O)CCOCC3)ccc2NC(=O)c2ncc(C#N)[nH]2)CC1]

To a suspension of 5-cyano-1H-imidazole-2-carboxylic acid [2-(4,4-dimethyl-cyclohex-1-enyl)-4-(4-hydroxy-tetrahydro-pyran-4-yl)-phenyl]-amide (48.0 mg, 0.114 mmol) (prepared in Example 1, step (h)) in 1 mL of DCM was added methyl glycolate (0.215 mL, 2.78 mmol), TFA (0.036 mL, 0.464 mmol), and the mixture was stirred for 8 h at RT. The mixture was concentrated and the methyl ester of the title compound was eluted from a 10-g SPE column with 50% EtOAc/hexanes. The resulting ester was dissolved in 1 mL of MeOH, 2N KOH (0.30 mL, 0.60 mmol) was added and the mixture stirred for 8 h at RT. The title compound was purified by RP-HPLC on a C18 column eluting with a linear gradient of 30-60% CH$_3$CN in 0.1% TFA/H$_2$O over 12 min to give 13 mg (30%) of a white solid. $^1$H-NMR (400 MHz, CD$_3$OD): δ 8.34 (d, J=8.6 Hz, 1H), 7.85 (s, 1H), 7.60 (s, 1H), 7.37 (dd, J=8.6, 2.2 Hz, 1H), 7.28 (d, J=2.2 Hz, 1H), 5.79 (m, 1H), 4.03-3.94 (m, 2H), 3.88-3.80 (m, 2H), 3.72 (s, 2H), 2.35-2.27 (m, 2H), 2.13-2.06 (m, 4H), 1.60 (t, J=6.3 Hz, 2H), 1.11 (s, 6H). Mass spectrum (ESI, m/z): Calcd. for C$_{26}$H$_{30}$N$_4$O$_5$, 477.2 (M−H). found 477.2.

Example 4

4-Cyano-1H-imidazole-2-carboxylic acid {2-(4,4-dimethyl-cyclohex-1-enyl)-4-[4-(2-methoxy-ethylamino)-tetrahydro-pyran-4-yl]-phenyl}-amide

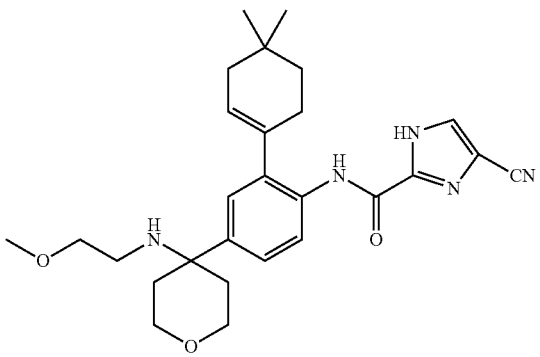 [SMILES: COCCNC1(c2ccc(NC(=O)c3nc(C#N)c[nH]3)c(C3=CCC(C)(C)CC3)c2)CCOCC1]

To a suspension of 4-cyano-1H-imidazole-2-carboxylic acid [2-(4,4-dimethyl-cyclohex-1-enyl)-4-(4-hydroxy-tetrahydro-pyran-4-yl)-phenyl]-amide (as prepared in Example 1, step (h), 50.0 mg, 0.120 mmol) in 1.5 mL of DCM at 0° C. was added SOCl$_2$ (26.0 µL, 0.360 mmol) under Ar. After stirring at RT for 2 h, the mixture was cooled to 0° C. To the reaction was then added 2-methoxyethylamine (104 µL, 1.20 mmol) and the resulting mixture was stirred at 0° C. for 2 h. The mixture was diluted with EtOAc (30 mL) and washed with H$_2$O (2×10 mL) and brine (10 mL). After drying over Na$_2$SO$_4$ and concentrating in vacuo, the residue was purified by silica gel chromatography (1-4% MeOH/DCM) to afford the title compound (36.8 mg, 65%) as a white solid. $^1$H-NMR (1:5 CD$_3$OD/CDCl$_3$; 400 MHz): δ 8.31 (d, 1H, J=8.6 Hz), 7.70 (s, 1H), 7.30 (dd, 1H, J=8.6, 2.3 Hz), 7.20 (d, 1H, J=2.3 Hz), 5.77 (m, 1H), 3.94 (m, 2H), 3.69 (m, 2H), 3.41 (t, 2H, J=6.1 Hz), 3.28 (s, 3H), 2.38 (t, 2H, J=6.1 Hz), 2.28 (m, 2H), 2.07-2.20 (m, 4H), 1.88 (m, 2H), 1.59 (t, 2H, J=6.3 Hz), 1.10 (s, 6H). Mass spectrum (ESI, m/z): Calcd. for C$_{27}$H$_{35}$N$_5$O$_3$, 476.3 (M−H). found 476.3.

Examples 5-9 were Prepared According to the Procedure in Example 4

| Example | Name | Structure | Mass Spectrum |
|---|---|---|---|
| 5 | 5-Cyano-1H-imidazole-2-carboxylic acid [4-(4-amino-tetrahydro-pyran-4-yl)-2-(4,4-dimethyl-cyclohex-1-enyl)-phenyl]-amide | 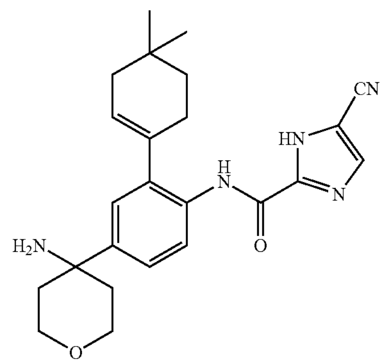 [SMILES: CC1(C)CC=C(c2cc(C3(N)CCOCC3)ccc2NC(=O)c2ncc(C#N)[nH]2)CC1] | (ESI, m/z): Calcd. for $C_{24}H_{29}N_5O_2$, 418.2 (M − H), found 417.9. |
| 6 | 5-Cyano-1H-imidazole-2-carboxylic acid [2-(4,4-dimethyl-cyclohex-1-enyl)-4-(4-morpholin-4-yl-tetrahydro-pyran-4-yl)-phenyl]-amide | 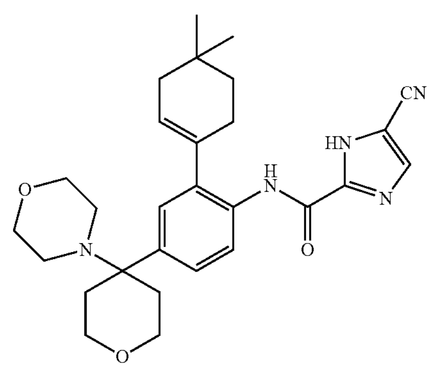 [SMILES: CC1(C)CC=C(c2cc(C3(N4CCOCC4)CCOCC3)ccc2NC(=O)c2ncc(C#N)[nH]2)CC1] | (APCI, m/z): Calcd. for $C_{28}H_{35}N_5O_3$, 488.3 (M − H), found 488.4. |
| 7 | 5-Cyano-1H-imidazole-2-carboxylic acid [4-(4-dimethylamino-tetrahydro-pyran-4-yl)-2-(4,4-dimethyl-cyclohex-1-enyl)-phenyl]-amide | 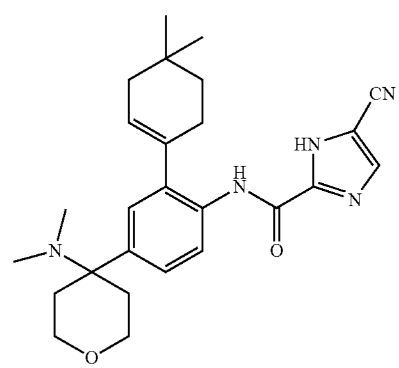 [SMILES: CN(C)C1(c2ccc(NC(=O)c3ncc(C#N)[nH]3)c(C3=CCC(C)(C)CC3)c2)CCOCC1] | (APCI, m/z): Calcd. for $C_{26}H_{33}N_5O_2$, 446.3 (M − H), found 446.5. |
| 8 | 5-Cyano-1H-imidazole-2-carboxylic acid {2-(4,4-dimethyl-cyclohex-1-enyl)-4-[4-(4-methyl-piperazin-1-yl)-tetrahydro-pyran-4-yl]-phenyl}-amide | 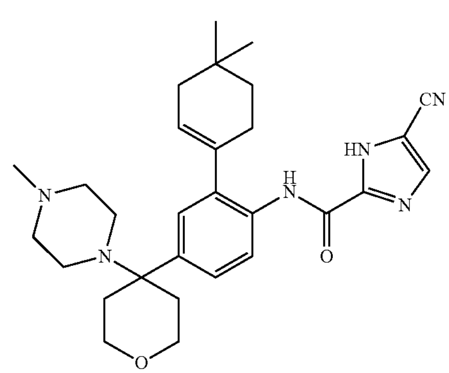 [SMILES: CN1CCN(C2(c3ccc(NC(=O)c4ncc(C#N)[nH]4)c(C4=CCC(C)(C)CC4)c3)CCOCC2)CC1] | (APCI, m/z): Calcd. for $C_{29}H_{38}N_6O_2$, 501.3 (M − H), found 501.4. |

| Example | Name | Structure | Mass Spectrum |
|---------|------|-----------|---------------|
| 9 | 5-Cyano-1H-imidazole-2-carboxylic acid [2-(4,4-dimethyl-cyclohex-1-enyl)-4-(4-piperazin-1-yl-tetrahydro-pyran-4-yl)-phenyl]-amide | 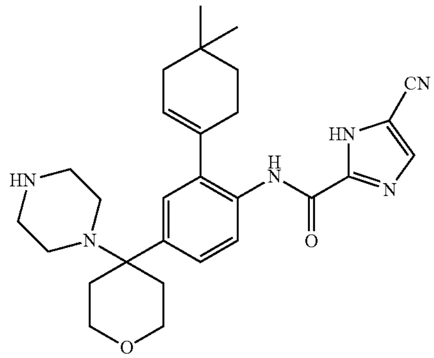 [SMILES: CC1(C)CC=C(c2cc(C3(N4CCNCC4)CCOCC3)ccc2NC(=O)c2ncc(C#N)[nH]2)CC1] | (APCI, m/z): Calcd. for $C_{28}H_{36}N_6O_2$, 487.3 (M − H), found 487.4. |

Example 10

(4-{4-[4-[(5-Cyano-1H-imidazole-2-carbonyl)-amino]-3-(4,4-dimethyl-cyclohex-1-enyl)-phenyl]-tetrahydro-pyran-4-yl}-piperazin-1-yl)-acetic acid trifluoroacetic acid salt To a solution of 5-cyano-1H-imidazole-2-carboxylic acid [2-(4,4-dimethyl-cyclohex-1-enyl)-4-(4-piperazin-1-yl-tetrahydro-pyran-4-yl)-phenyl]-amide trifluoroacetic acid salt (22 mg, 0.036 mmol) (prepared in Example 1, step (h)) in DCM (0.3 mL) was added NEt$_3$ (0.015 mL, 0.11 mmol) and ethyl bromoacetate (0.0044 mL, 0.040 mmol) and the mixture stirred for 10 h at RT. The mixture was concentrated and the residue dissolved in 1 mL of EtOH and 7N KOH (0.031 mL, 0.22 mmol) was added and the mixture stirred for 3 h at RT. The mixture was diluted with 5 mL of H$_2$O, the pH adjusted to 2, and the title compound purified by RP-HPLC on a C18 column eluting with a linear gradient of 20-50% CH$_3$CN in 0.1% TFA/H$_2$O over 10 min to give 22 mg (91%) of a white solid. $^1$H-NMR (400 MHz, CD$_3$OD): δ 8.41 (d, J=8.6 Hz, 1H), 8.01 (s, 1H), 7.44 (dd, J=8.6, 2.2 Hz, 1H), 7.31 (d, J=2.2 Hz, 1H), 5.81 (m, 1H), 4.00-3.92 (m, 2H), 3.70 (s, 2H), 3.42-3.34 (m, 2H), 3.26-2.86 (m, 8H), 2.70-2.58 (m, 2H), 2.38-2.29 (m, 2H), 2.23-2.05 (m, 4H), 1.60 (t, J=6.3 Hz, 2H), 1.10 (s, 6H). Mass spectrum (APCI, m/z): Calcd. for $C_{30}H_{38}N_6O_4$, 545.3 (M−H). found 545.3.

Example 11

4-Cyano-1H-imidazole-2-carboxylic acid [2-(4,4-dimethyl-cyclohex-1-enyl)-4-(4-hydroxy-tetrahydro-thiopyran-4-yl)-phenyl]-amide To a solution of 4-cyano-1H-imidazole-2-carboxylic acid [4-bromo-2-(4,4-dimethyl-cyclohex-1-enyl)-phenyl]-amide (as prepared in Example 1, step (g), 120 mg, 0.300 mmol) in 4 mL of THF at −78° C. under Ar was added isopropylmagnesium chloride (165 μL, 0.331 mmol, 2.0 M in THF). The resulting mixture was warmed to RT and stirred for 5 min, cooled to −78° C. again. To the mixture was added tert-butyllithium (530 μL, 0.902 mmol, 1.7 M in pentane) and the resulting mixture was stirred at −78° C. for 10 min. A solution of tetrahydro-thiopyran-4-one (175 mg, 1.50 mmol) in 1 mL of THF was then added, and the reaction was warmed to RT and stirred for 0.5 h under Ar. The mixture was treated with 2 mL of saturated NH$_4$Cl followed by 20 mL of EtOAc, washed with brine (10 mL) and dried (Na$_2$SO$_4$). Removal of the solvent under reduced pressure followed by flash chromatography of the residue on silica gel (1-2% MeOH/DCM) gave 85.0 mg (65%) of the title compound as a white solid. $^1$H-NMR (CDCl$_3$; 400 MHz): δ 12.62 (s, 1H), 9.72 (s, 1H), 8.32 (d, 1H, J=8.6 Hz), 7.74 (d, 1H, J=2.3 Hz), 7.42 (dd, 1H, J=8.6, 2.3 Hz), 7.33 (d, 1H, J=2.3 Hz), 5.78 (m, 1H), 3.12-3.33 (br s, 2H), 2.46-2.54 (m, 2H), 2.26-2.33 (m, 2H), 2.16-

2.22 (m, 2H), 2.00-2.13 (m, 4H), 1.79 (s, 1H), 1.59 (t, 2H, J=6.3 Hz), 1.10 (s, 6H). Mass spectrum (ESI, m/z): Calcd. for C$_{24}$H$_{28}$N$_4$O$_2$S, 437.2 (M+H). found 437.2.

Example 12

4-Cyano-1H-imidazole-2-carboxylic acid [2-(4,4-dimethyl-cyclohex-1-enyl)-4-(4-hydroxy-1,1-dioxo-hexahydro-1λ$^6$-thiopyran-4-yl)-phenyl]-amide

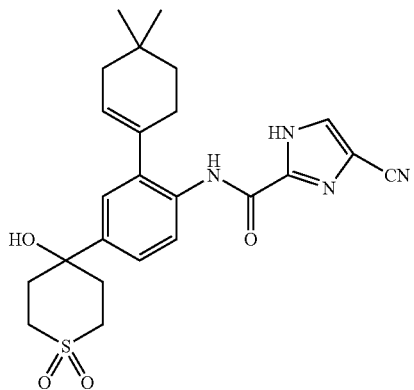 [SMILES: CC1(C)CC=C(c2cc(C3(O)CCS(=O)(=O)CC3)ccc2NC(=O)c2nc(C#N)c[nH]2)CC1]

To a solution of 4-cyano-1H-imidazole-2-carboxylic acid [2-cyclohex-1-enyl-4-(2-hydroxy-1-hydroxymethyl-ethyl)-phenyl]-amide (as prepared in the Example 11, 45.0 mg, 0.103 mmol) in 2 mL of 3:1 DCM/1,4-dioxane at −78° C. was added a solution of MCPBA (57.0 mg, 0.165 mmol) in 2 mL of 3:1 DCM/1,4-dioxane. The resulting mixture was stirred at −78° C. for 3 h under Ar. After warming to 0° C., the reaction was treated with 2 mL of 15% Na$_2$S$_2$O$_3$ aqueous solution followed by 2 mL of satd NaHCO$_3$ aqueous solution and extracted with EtOAc (2×30 mL). The combined organic layers were dried (Na$_2$SO$_4$) and concentrated in vacuo. The residue was purified by flash chromatography on silica gel with 1-2% MeOH/DCM to afford 28 mg (58%) of the title compound as a white solid: $^1$H-NMR (CD$_3$OD; 400 MHz): δ 8.26 (d, 1H, J=8.6 Hz), 7.83 (s, 1H), 7.40 (dd, 1H, J=8.6, 2.3 Hz), 7.31 (d, 1H, J=2.3 Hz), 5.74 (m, 1H), 3.57 (td, 2H, J=13.4, 3.0 Hz), 2.95 (m, 2H), 2.60 (td, 2H, J=14.4, 3.0 Hz), 2.29 (m, 2H), 2.13 (m, 2H), 2.07 (m, 2H), 1.58 (t, 2H, J=6.3 Hz), 1.08 (s, 6H). Mass spectrum (ESI, m/z): Calcd. for C$_{24}$H$_{28}$N$_4$O$_4$S, 469.2 (M+H). found 469.1.

Example 13

4-Cyano-1H-imidazole-2-carboxylic acid [4-(1-acetyl-4-amino-piperidin-4-yl)-2-(4,4-dimethyl-cyclohex-1-enyl)-phenyl]-amide acetic acid salt

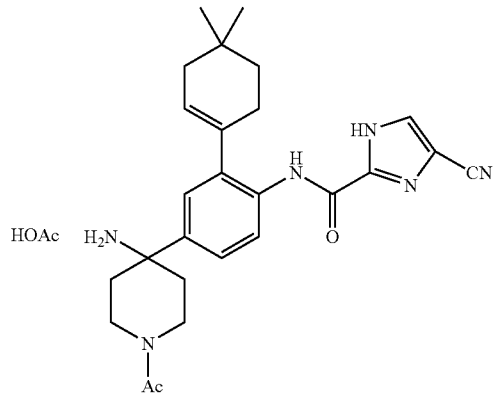 [SMILES: CC(=O)N1CCC(N)(c2ccc(NC(=O)c3nc(C#N)c[nH]3)c(C3=CCC(C)(C)CC3)c2)CC1 ; "HOAc"]

a) 4-Cyano-1H-imidazole-2-carboxylic acid [4-(1-acetyl-4-azido-piperidin-4-yl)-2-(4,4-dimethyl-cyclohex-1-enyl)-phenyl]-amide

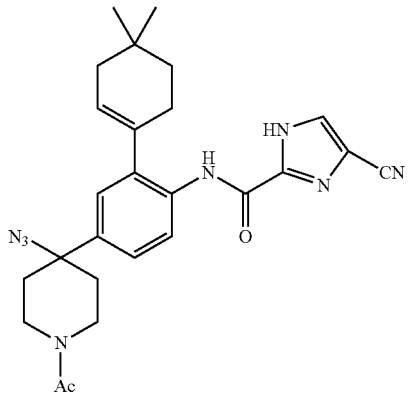 [SMILES: CC(=O)N1CCC(N=[N+]=[N-])(c2ccc(NC(=O)c3nc(C#N)c[nH]3)c(C3=CCC(C)(C)CC3)c2)CC1]

To a mixture of 4-cyano-1H-imidazole-2-carboxylic acid [4-(1-acetyl-4-hydroxy-piperidin-4-yl)-2-(4,4-dimethyl-cyclohex-1-enyl)-phenyl]-amide (as prepared in Example 35, 40.0 mg, 0.0867 mmol) and NaN$_3$ (56.3 mg, 0.0867 mmol) in 2 mL of DCM at 0° C. under Ar was added TFA (100 μL, 1.30 mmol). The resulting mixture was stirred at 0° C. for 0.5 h, at RT for 2 d under Ar. Treated with 20 mL of EtOAc, the mixture was washed with saturated NaHCO$_3$ aqueous solution (10 mL), brine (5 mL) and dried (Na$_2$SO$_4$). Removal of the solvent under reduced pressure followed by flash chromatography of the residue on silica gel (1-3% MeOH/DCM) gave 40.0 mg (95%) of the title compound as a white solid. Mass spectrum (ESI, m/z): Calcd. for C$_{26}$H$_{30}$N$_8$O$_2$, 487.3 (M+H). found 487.0.

b) 4-Cyano-1H-imidazole-2-carboxylic acid [4-(1-acetyl-4-amino-piperidin-4-yl)-2-(4,4-dimethyl-cyclohex-1-enyl)-phenyl]-amide acetic acid salt To a mixture of 4-cyano-1H-imidazole-2-carboxylic acid [4-(1-acetyl-4-azido-piperidin-4-yl)-2-(4,4-dimethyl-cyclohex-1-enyl)-phenyl]-amide (as prepared in the previous step, 40.0 mg, 0.0822 mmol) and zinc (54.0 mg, 0.822 mmol) in 1.6 mL of THF was added acetic acid (0.40 mL). The resulting mixture was stirred at RT for 16 h under Ar. The solid was removed by filtration on Celite and the filtrate was concentrated in vacuo. The residue was purified by flash chromatography on silica gel (10% MeOH/DCM) to give 13 mg (30%) of the title compound as a white solid. $^1$H-NMR (CD$_3$OD; 400 MHz): δ 8.33 (d, 1H, J=8.6 Hz), 7.91 (s, 1H), 7.52 (dd, 1H, J=8.6, 2.3 Hz), 7.40 (s, 1H), 5.77 (m, 1H), 3.76-3.98 (m, 2H), 3.42 (m, 2H), 2.46 (m, 2H), 2.32 (m, 2H), 2.13 (s, 3H), 2.07 (m, 2H), 1.86-2.03 (m, 2H), 1.93 (s, 6H), 1.59 (t, 2H, J=6.1 Hz). Mass spectrum (ESI-neg, m/z): Calcd. for C$_{26}$H$_{32}$N$_6$O$_2$, 459.3 (M−H). found 459.5.

Example 14

4-Cyano-1H-imidazole-2-carboxylic acid [2-cyclohex-1-enyl-4-(4-hydroxy-tetrahydro-thiopyran-4-yl)-phenyl]-amide

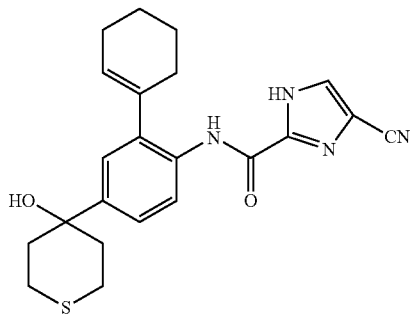 [SMILES: N#Cc1c[nH]c(C(=O)Nc2ccc(C3(O)CCSCC3)cc2C2=CCCCC2)n1]

a) 4-Bromo-2-cyclohex-1-enyl-phenylamine

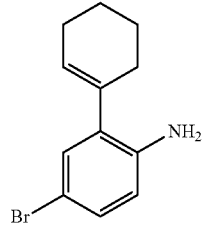 [SMILES: Nc1ccc(Br)cc1C1=CCCCC1]

To a mixture of 4-bromo-2-iodo-phenylamine (2.00 g, 6.71 mmol), 2-cyclohex-1-enyl-4,4,5,5-tetramethyl-[1,3,2]dioxaborolane (1.40 g, 6.71 mmol) and Pd(PPh$_3$)$_4$ (388 mg, 0.336 mmol) in 40 mL of 1,4-dioxane was added 2.0 M aq Na$_2$CO$_3$ solution (26.8 mL, 53.7 mmol). After stirring at 80° C. for 5 h under Ar, the reaction was cooled to RT. The mixture was treated with EtOAc (100 mL), washed with H$_2$O (3×30 mL) and brine (20 mL). The organic layer was dried (Na$_2$SO$_4$) and concentrated in vacuo. The residue was purified by flash chromatography on silica gel (10-20% EtOAc/hexane) to give 1.47 g (87%) of the title compound as a light brown oil. Mass spectrum (ESI, m/z): Calcd. for C$_{12}$H$_{14}$BrN, 252.0 (M+H). found 252.0.

b) 4-Cyano-1-(2-trimethylsilanyl-ethoxymethyl)-1H-imidazole-2-carboxylic acid (4-bromo-2-cyclohex-1-enyl-phenyl)-amide

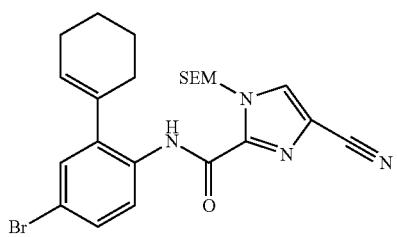 [SMILES: C[Si](C)(C)CCOCn1cc(C#N)nc1C(=O)Nc1ccc(Br)cc1C1=CCCCC1]

To a mixture of 4-bromo-2-cyclohex-1-enyl-phenylamine (as prepared in the previous step, 1.23 g, 4.88 mmol), potassium 4-cyano-1-(2-trimethylsilanyl-ethoxymethyl)-1H-imidazole-2-carboxylate (as prepared in Example 1, step (d), 1.49 g, 4.88 mmol) and bromotripyrrolidinophosphonium hexafluorophosphate (PyBroP) (2.27 g, 4.88 mmol) in 25 mL of DMF was added N,N-diisopropylethylamine (DIEA) (2.55 mL, 14.6 mmol). After stirring at RT for 16 h, the mixture was treated with 100 mL of EtOAc and washed with H$_2$O (2×30 mL), brine (30 mL) and dried (Na$_2$SO$_4$). The organic solvent was evaporated and the residue was purified by flash chromatography on silica gel (5-10% EtOAc/hexane) to give 2.21 g (90%) of the title compound as a white solid. $^1$H-NMR (CDCl$_3$; 400 MHz): δ 9.70 (s, 1H), 8.26 (d, 1H, J=8.6 Hz), 7.78 (s, 1H), 7.36 (dd, 1H, J=8.6, 2.3 Hz), 7.31 (d, 1H, J=2.3 Hz), 5.94 (s, 2H), 5.86 (m, 1H), 3.66 (t, 2H, J=8.3 Hz), 2.19-2.33 (m, 4H), 1.75-1.88 (m, 4H), 0.97 (t, 2H, J=8.3 Hz), 0.00 (s, 9H).

c) 4-Cyano-1H-imidazole-2-carboxylic acid (4-bromo-2-cyclohex-1-enyl-phenyl)-amide

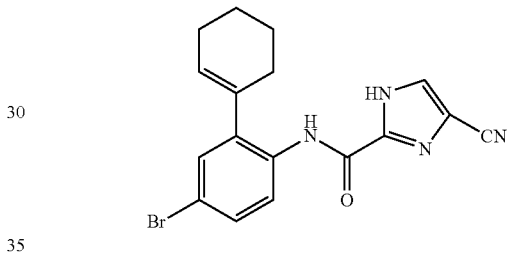

To a solution of 4-cyano-1-(2-trimethylsilanyl-ethoxymethyl)-1H-imidazole-2-carboxylic acid (4-bromo-2-cyclohex-1-enyl-phenyl)-amide (as prepared in the previous step, 1.20 g, 2.39 mmol) in 10 mL of DCM (CH$_2$Cl$_2$) was added 0.30 mL of EtOH followed by 5.0 mL of TFA. After stirring at RT for 3 h, the mixture was treated with 20 mL of n-propanol and concentrated in vacuo. The residue was triturated with DCM to afford 853 mg (96%) of the title compound as a white solid. $^1$H-NMR (DMSO-d$_6$; 400 MHz): δ 9.80 (s, 1H), 8.30 (s, 1H), 7.94 (d, 1H, J=8.6 Hz), 7.50 (dd, 1H, J=8.6, 2.3 Hz), 7.39 (d, 1H, J=2.3 Hz), 5.80 (m, 1H), 2.12-2.25 (m, 4H), 1.61-1.77 (m, 4H). Mass spectrum (ESI, m/z): Calcd. for C$_{17}$H$_{15}$BrN$_4$O, 371.0 (M+H). found 371.0.

d) 4-Cyano-1H-imidazole-2-carboxylic acid [2-cyclohex-1-enyl-4-(4-hydroxy-tetrahydro-thiopyran-4-yl)-phenyl]-amide The title compound was prepared by the procedure of Example 11 using 4-cyano-1H-imidazole-2-carboxylic acid (4-bromo-2-cyclohex-1-enyl-phenyl)-amide (as prepared in the previous step, 120 mg, 0.323 mmol) and tetrahydro-thiopyran-4-one (188 mg, 1.62 mmol). Silica gel chromatography (1-3% MeOH/DCM) afforded the title compound (82.3 mg, 62%) as a white solid. $^1$H-NMR (CDCl$_3$; 400 MHz): δ 12.56 (s, 1H), 9.66 (s, 1H), 8.29 (d, 1H, J=8.6 Hz), 7.74 (d, 1H, J=2.5 Hz), 7.42 (dd, 1H, J=8.6, 2.3 Hz), 7.33 (d, 1H, J=2.3 Hz), 5.86 (m, 1H), 3.22 (m, 2H), 2.46-2.54 (m, 2H), 2.22-2.33

(m, 4H), 2.16-2.22 (m, 2H), 2.01-2.09 (m, 2H), 1.73-1.89 (m, 5H). Mass spectrum (ESI, m/z): Calcd. for $C_{22}H_{24}N_4O_2S$, 409.2 (M+H). found 409.1.

Example 15

4-Cyano-1H-imidazole-2-carboxylic acid [2-cyclohex-1-enyl-4-(4-hydroxy-1,1-dioxo-hexahydro-1$\lambda^6$-thiopyran-4-yl)-phenyl]-amide

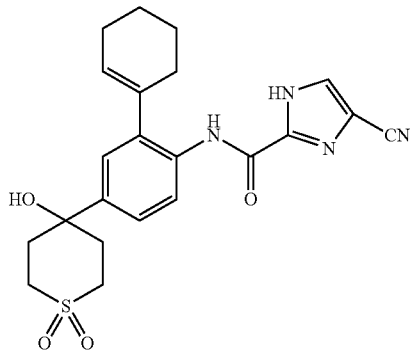 [SMILES: N#Cc1c[nH]c(C(=O)Nc2ccc(C3(O)CCS(=O)(=O)CC3)cc2C2=CCCCC2)n1]

The title compound was prepared by the procedure of Example 12 using 4-cyano-1H-imidazole-2-carboxylic acid [2-cyclohex-1-enyl-4-(4-hydroxy-tetrahydro-thiopyran-4-yl)-phenyl]-amide (as prepared in Example 14, step (d), 60.0 mg, 0.147 mmol). Silica gel chromatography (10-40% EtOAc/DCM) afforded the title compound (25.7 mg, 40%) as a white solid. $^1$H-NMR (CD$_3$OD; 400 MHz): δ 8.26 (d, 1H, J=8.6 Hz), 7.83 (s, 1H), 7.40 (dd, 1H, J=8.6, 2.3 Hz), 7.31 (d, 1H, J=2.3 Hz), 5.74 (m, 1H), 3.57 (td, 2H, J=13.4, 3.0 Hz), 2.95 (m, 2H), 2.60 (td, 2H, J=14.4, 3.0 Hz), 2.29 (m, 2H), 2.13 (m, 2H), 2.07 (m, 2H), 1.58 (t, 2H, J=6.3 Hz), 1.08 (s, 6H). Mass spectrum (ESI, m/z): Calcd. for $C_{24}H_{28}N_4O_4S$, 469.2 (M+H). found 469.1.

Example 16

4-[4-[(4-Cyano-1H-imidazole-2-carbonyl)-amino]-3-(4,4-dimethyl-cyclohex-1-enyl)-phenyl]-tetrahydro-pyran-4-carboxylic acid methyl ester

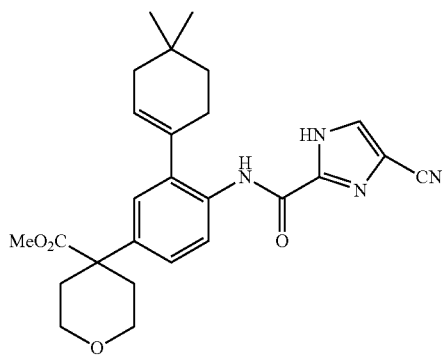 [SMILES: COC(=O)C1(c2ccc(NC(=O)c3nc(C#N)c[nH]3)c(C3=CCC(C)(C)CC3)c2)CCOCC1]

a) 4-(4-Nitro-phenyl)-tetrahydro-pyran-4-carboxylic acid methyl ester

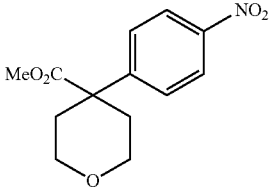 [SMILES: COC(=O)C1(c2ccc([N+](=O)[O-])cc2)CCOCC1]

To a solution of lithium diisopropylamide (12.2 mL, 22.0 mmol, 1.8 M) in 40 mL of THF at −78° C. was added tetrahydro-pyran-4-carboxylic acid methyl ester (2.88 g, 20.0 mmol) dropwise. The resulting mixture was stirred at −78° C. for 15 min, warmed to RT. 1,3-Dimethyl-tetrahydro-pyrimidin-2-one (2.69 g, 22.0 mmol) was added. The reaction was cooled to −78° C. again, 1-fluoro-4-nitro-benzene (3.10 g, 22.0 mmol) was added slowly. The resulting mixture was warmed to RT and stirred for 1 d under Ar. The reaction was treated with 30 mL of saturated NH$_4$Cl and extracted with 80 mL of EtOAc. The organic extract was washed with H$_2$O (50 mL), brine (20 mL), dried (Na$_2$SO$_4$) and concentrated. The residue was purified by flash chromatography on silica gel (5-20% EtOAc/hexane) to give 1.61 g (30%) of the title compound as a yellow solid. $^1$H-NMR (CDCl$_3$; 400 MHz): δ 8.21 (d, 1H, J=9.0 Hz), 7.56 (d, 1H, J=9.0 Hz), 3.97 (m, 2H), 3.70 (s, 3H), 3.57 (m, 2H), 2.56 (m, 2H), 2.00 (m, 2H).

b) 4-(4-Amino-phenyl)-tetrahydro-pyran-4-carboxylic acid methyl ester

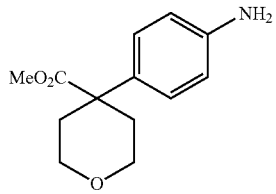

A mixture of 4-(4-nitro-phenyl)-tetrahydro-pyran-4-carboxylic acid methyl ester (as prepared in the previous step, 2.12 g, 8.00 mmol) and 10% Pd/C (1.06 g, 50 wt %) in 20 ml, of MeOH was stirred at RT under H$_2$ (balloon pressure) for 2 h. The Pd catalyst was removed by filtration on Celite and the filtrate was concentrated to give 1.69 g (90%) of the title compound as a white solid. Mass spectrum (ESI, m/z): Calcd. for $C_{13}H_{17}NO_3$, 236.1 (M+H). found 236.2.

c) 4-(4-Amino-3-bromo-phenyl)-tetrahydro-pyran-4-carboxylic acid methyl ester

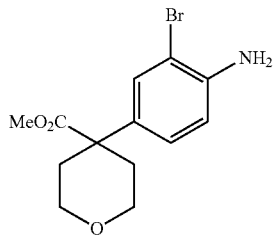 [SMILES: COC(=O)C1(c2ccc(N)c(Br)c2)CCOCC1]

To a solution of 4-(4-amino-phenyl)-tetrahydro-pyran-4-carboxylic acid methyl ester (as prepared in the previous step, 1.65 g, 7.01 mmol) in 100 mL of 1:1 DCM/CH$_3$CN at 0° C. was slowly added N-bromosuccinimide (NBS) (1.25 g, 7.01 mmol) in 25 mL of 1:1 DCM/CH$_3$CN under Ar. After stirring at 0° C. for 0.5 h, the mixture was treated with 50 mL of EtOAc and washed with H$_2$O (2×30 mL) and brine H$_2$O (20 mL). The organic layer was dried (Na$_2$SO$_4$) and concentrated in vacuo. The residue was purified by flash chromatography on silica gel (1-4% EtOAc/DCM) to give 1.85 g (84%) of the title compound as a white solid. Mass spectrum (ESI, m/z): Calcd. for C$_{13}$H$_{16}$BrNO$_3$, 314.0 (M+H). found 314.2.

d) 4-[4-Amino-3-(4,4-dimethyl-cyclohex-1-enyl)-phenyl]-tetrahydro-pyran-4-carboxylic acid methyl ester

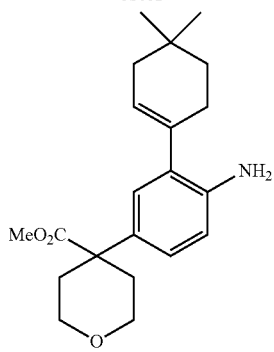 [SMILES: COC(=O)C1(c2ccc(N)c(C3=CCC(C)(C)CC3)c2)CCOCC1]

To a mixture of 4-(4-amino-3-bromo-phenyl)-tetrahydro-pyran-4-carboxylic acid methyl ester (as prepared in the previous step, 1.45 g, 4.61 mmol), 4,4-dimethylcyclohexen-1-ylboronic acid (782 mg, 5.08 mmol) and dichloro(1,1-bisdiphenylphosphino-ferrocene palladium (II) (Pd(dppf)Cl$_2$) dichloromethane adduct (337 mg, 0.461 mmol) in 40 mL of DMF was added K$_3$PO$_4$ (3.91 g, 18.4 mmol). The resulting mixture was stirred at 70° C. for 18 h under Ar. After cooling to RT, the mixture was treated with 150 mL of EtOAc, washed with H$_2$O (3×30 mL) and brine (30 mL). The organic layer was dried (Na$_2$SO$_4$) and concentrated in vacuo. The residue was purified by flash chromatography on silica gel (0-2% EtOAc/DCM) to afford 1.14 g (72%) of the title compound as a white solid. Mass spectrum (ESI, m/z): Calcd. for C$_{21}$H$_{29}$NO$_3$, 344.2 (M+H). found 344.4.

e) 4-[4-{[4-Cyano-1-(2-trimethylsilanyl-ethoxymethyl)-1H-imidazole-2-carbonyl]-amino}-3-(4,4-dimethyl-cyclohex-1-enyl)-phenyl]-tetrahydro-pyran-4-carboxylic acid methyl ester

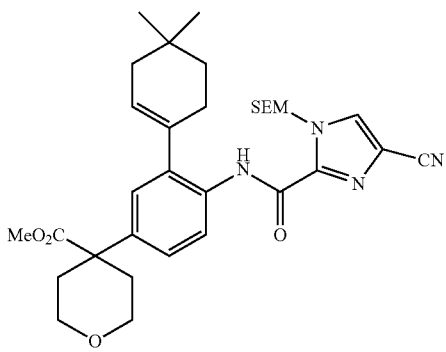 [SMILES: COC(=O)C1(c2ccc(NC(=O)c3nc(C#N)cn3COCC[Si](C)(C)C)c(C3=CCC(C)(C)CC3)c2)CCOCC1]

The title compound was prepared by the coupling procedure of Example 1, step (f) using 4-[4-amino-3-(4,4-dimethyl-cyclohex-1-enyl)-phenyl]-tetrahydro-pyran-4-carboxylic acid methyl ester (as prepared in the previous step, 650 mg, 1.89 mmol) and potassium 4-cyano-1-(2-trimethylsilanyl-ethoxymethyl)-1H-imidazole-2-carboxylate (as prepared in Example 1, step (d), 636 mg, 2.08 mmol). Silica gel chromatography (DCM) afforded the title compound (1.01 g, 90%) as a colorless oil. Mass spectrum (ESI, m/z): Calcd. for C$_{32}$H$_{44}$N$_4$O$_5$Si, 593.3 (M+H). found 593.0.

f) 4-[4-[(4-Cyano-1H-imidazole-2-carbonyl)-amino]-3-(4,4-dimethyl-cyclohex-1-enyl)-phenyl]-tetrahydro-pyran-4-carboxylic acid methyl ester The title compound was prepared by the procedure of Example 1, step (g) using 4-[4-{[4-cyano-1-(2-trimethylsilanyl-ethoxymethyl)-1H-imidazole-2-carbonyl]-amino}-3-(4,4-dimethyl-cyclohex-1-enyl)-phenyl]-tetrahydro-pyran-4-carboxylic acid methyl ester (as prepared in the previous step, 550 mg, 0.927 mmol). The title compound (411 mg, 96%) is a white solid. $^1$H-NMR (CDCl$_3$; 400 MHz): δ 12.14 (s, 1H), 9.66 (s, 1H), 8.34 (d, 1H, J=8.6 Hz), 7.74 (d, 1H, J=2.5 Hz), 7.34 (dd, 1H, J=8.6, 2.3 Hz), 7.18 (d, 1H, J=2.3 Hz), 5.78 (m, 1H), 3.96 (m, 2H), 3.71 (s, 3H), 3.57 (m, 2H), 2.54 (m, 2H), 2.28 (m, 2H), 2.11 (m, 2H), 2.0 (m, 2H), 1.59 (t, 2H, J=6.2 Hz), 1.11 (s, 6H). Mass spectrum (ESI, m/z): Calcd. for C$_{26}$H$_{30}$N$_4$O$_4$, 463.2 (M+H). found 463.2.

Example 17

4-[4-[(4-Cyano-1H-imidazole-2-carbonyl)-amino]-3-(4,4-dimethyl-cyclohex-1-enyl)-phenyl]-tetrahydro-pyran-4-carboxylic acid

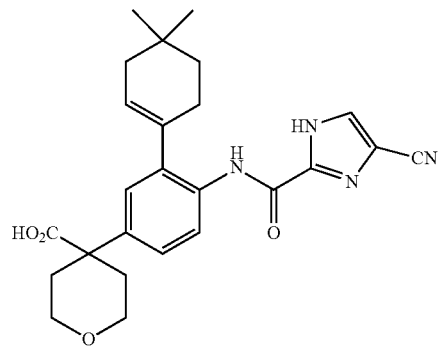

To a solution of 4-[4-[(4-cyano-1H-imidazole-2-carbonyl)-amino]-3-(4,4-dimethyl-cyclohex-1-enyl)-phenyl]-tetrahydro-pyran-4-carboxylic acid methyl ester (as prepared in Example 16, step (f), 129 mg, 0.279 mmol) in 2 mL of 1:1 THF/MeOH was added 6 N NaOH (400 μL, 2.40 mmol). After stirring at RT for 2 d, the mixture was treated with 10 mL of H$_2$O and washed with EtOAc (3×10 mL). The aqueous layer was acidified to pH=5 with 15% citric acid and extracted with 10:1 EtOAc-MeOH (3×10 mL). The combined organic layers were dried (Na$_2$SO$_4$) and concentrated in vacuo to afford 119 mg (95%) of the title compound as a white solid. $^1$H-NMR (CD$_3$OD; 400 MHz): δ 8.20 (d, 1H, J=8.8 Hz), 8.00 (s, 1H), 7.37 (dd, 1H, J=8.8, 2.3 Hz), 7.24 (d, 1H, J=2.3 Hz), 5.75 (m, 1H), 3.91 (m, 2H), 3.61 (t, 2H, J=11.5 Hz), 2.49 (m, 2H), 2.30 (m, 2H), 2.08 (m, 2H), 1.95 (m, 2H), 1.60 (t, 2H, J=6.1 Hz), 1.09 (s, 6H). Mass spectrum (ESI, m/z): Calcd. for C$_{25}$H$_{28}$N$_4$O$_4$, 449.2 (M+H). found 449.2.

Example 18

4-{4-[(4-Cyano-1H-imidazole-2-carbonyl)-amino]-3-cyclohex-1-enyl-phenyl}-tetrahydro-pyran-4-carboxylic acid

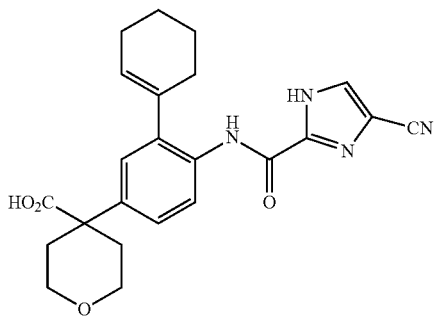 [SMILES: N#Cc1c[nH]c(C(=O)Nc2ccc(C3(C(=O)O)CCOCC3)cc2C2=CCCCC2)n1]

a) 4-(4-Amino-3-cyclohex-1-enyl-phenyl)-tetrahydro-pyran-4-carboxylic acid methyl ester

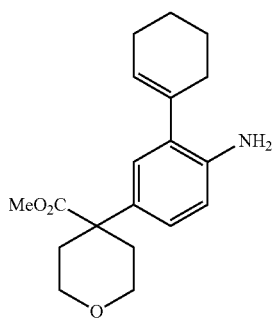 [SMILES: COC(=O)C1(c2ccc(N)c(C3=CCCCC3)c2)CCOCC1]

The title compound was prepared by the Suzuki coupling procedure of Example 16, step (d) using 4-(4-amino-3-bromo-phenyl)-tetrahydro-pyran-4-carboxylic acid methyl ester (as prepared in the Example 16, step (c), 380 mg, 1.21 mmol), and 2-cyclohex-1-enyl-4,4,5,5-tetramethyl-[1,3,2]dioxaborolane (277 mg, 1.33 mmol). Silica gel chromatography (0-2% EtOAc/DCM) afforded the title compound (268 mg, 70%) as a white solid. Mass spectrum (ESI, m/z): Calcd. for $C_{19}H_{25}NO_3$, 316.2 (M+H). found 316.2.

b) 4-(4-{[4-Cyano-1-(2-trimethylsilanyl-ethoxymethyl)-1H-imidazole-2-carbonyl]-amino}-3-cyclohex-1-enyl-phenyl)-tetrahydro-pyran-4-carboxylic acid methyl ester

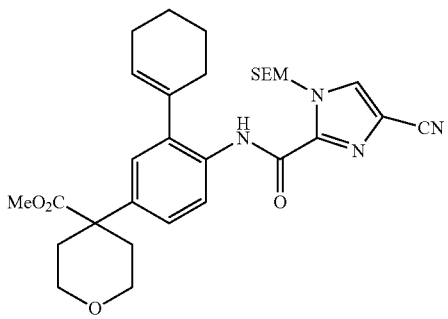 [SMILES: COC(=O)C1(c2ccc(NC(=O)c3nc(C#N)cn3COCC[Si](C)(C)C)c(C3=CCCCC3)c2)CCOCC1]

The title compound was prepared by the coupling procedure of Example 1, step (f) using 4-(4-amino-3-cyclohex-1-enyl-phenyl)-tetrahydro-pyran-4-carboxylic acid methyl ester (as prepared in the previous step, 250 mg, 0.793 mmol), and potassium 4-cyano-1-(2-trimethylsilanyl-ethoxymethyl)-1H-imidazole-2-carboxylate (as prepared in Example 1, step (d), 266 mg, 0.872 mmol). Silica gel chromatography (20% EtOAc-hexane) afforded the title compound (348 mg, 78%) as a colorless oil. Mass spectrum (ESI, m/z): Calcd. for $C_{30}H_{40}N_4O_5Si$, 565.3 (M+H). found 565.0.

c) 4-{4-[(4-Cyano-1H-imidazole-2-carbonyl)-amino]-3-cyclohex-1-enyl-phenyl}-tetrahydro-pyran-4-carboxylic acid methyl ester

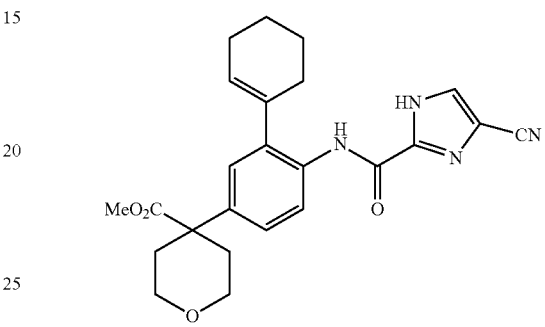

The title compound was prepared by the procedure of Example 1, step (g) using 4-(4-{[4-cyano-1-(2-trimethylsilanyl-ethoxymethyl)-1H-imidazole-2-carbonyl]-amino}-3-cyclohex-1-enyl-phenyl)-tetrahydro-pyran-4-carboxylic acid methyl ester (as prepared in the previous step, 339 mg, 0.600 mmol). The title compound (249 mg, 95%) is a faint yellow solid. Mass spectrum (ESI, m/z): Calcd. for $C_{24}H_{26}N_4O_4$, 435.2 (M+H). found 435.2.

d) 4-{4-[(4-Cyano-1H-imidazole-2-carbonyl)-amino]-3-cyclohex-1-enyl-phenyl}-tetrahydro-pyran-4-carboxylic acid

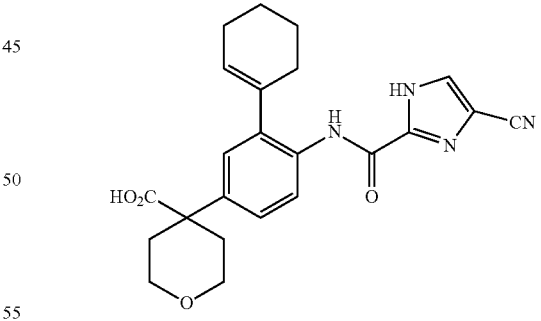

The title compound was prepared by the procedure of Example 17 using 4-{4-[(4-cyano-1H-imidazole-2-carbonyl)-amino]-3-cyclohex-1-enyl-phenyl}-tetrahydro-pyran-4-carboxylic acid methyl ester (as prepared in the previous step, 239 mg, 0.550 mmol). The title compound (227 mg, 98%) is a white solid. $^1$H-NMR (CD$_3$OD; 400 MHz): δ 8.25 (d, 1H, J=8.6 Hz), 7.84 (s, 1H), 7.35 (dd, 1H, J=8.6, 2.3 Hz), 7.23 (d, 1H, J=2.3 Hz), 5.84 (m, 1H), 3.94 (m, 2H), 3.66 (m, 2H), 2.54 (m, 2H), 2.20-2.34 (m, 4H), 1.97 (m, 2H), 1.74-1.89 (m, 4H). Mass spectrum (ESI, m/z): Calcd. for $C_{23}H_{24}N_4O_4$, 421.2 (M+H). found 421.1.

Example 19

4-Cyano-1H-imidazole-2-carboxylic acid [4-(4-carbamoyl-tetrahydro-pyran-4-yl)-2-cyclohex-1-enyl-phenyl]-amide

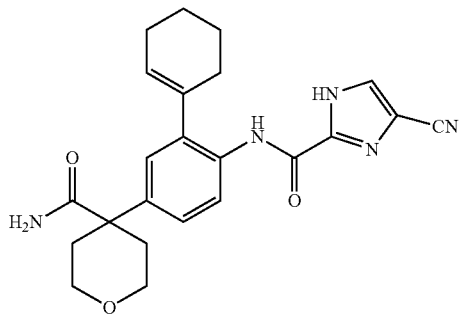 [SMILES: N#Cc1c[nH]c(C(=O)Nc2ccc(C3(C(N)=O)CCOCC3)cc2C2=CCCCC2)n1]

To a solution of 4-{4-[(4-cyano-1H-imidazole-2-carbonyl)-amino]-3-cyclohex-1-enyl-phenyl}-tetrahydro-pyran-4-carboxylic acid (as prepared in Example 18, step (d), 14.5 mg, 0.0345 mmol) in 1 mL of THF was added ClCO₂Me (3.6 mg, 0.038 mmol). The mixture was cooled to 0° C., DIEA (18 μL, 0.10 mmol) was added. After warming to RT and stirring for 1 h, the mixture was cooled back to 0° C. Concentrated ammonium hydroxide (25 μL, 0.37 mmol) was added and the resulting mixture was warmed to RT and stirred for 16 h. The reaction was treated with 30 mL of EtOAc and washed with brine (10 mL). The organic layer was dried over Na₂SO₄ and concentrated in vacuo. The residue was purified by silica gel chromatography (1-5 MeOH/DCM) to afford the title compound (4.7 mg, 32%) as a white solid. ¹H-NMR (CDCl₃; 400 MHz): δ 12.00 (s, 1H), 9.53 (s, 1H), 8.33 (d, 1H, J=8.6 Hz), 7.74 (d, 1H, J=2.3 Hz), 7.33 (dd, 1H, J=8.6, 2.3 Hz), 7.20 (d, 1H, J=2.3 Hz), 5.85 (m, 1H), 5.81 (br s, 1H), 5.32 (br s, 1H), 3.82 (m, 4H), 2.38 (m, 2H), 2.19-2.34 (m, 4H), 2.11 (m, 2H), 1.82 (m, 2H). Mass spectrum (ESI, m/z): Calcd. for $C_{23}H_{25}N_5O_3$, 420.2 (M+H). found 420.1.

Example 20

4-Cyano-1H-imidazole-2-carboxylic acid [2-cyclohex-1-enyl-4-(4-hydroxymethyl-tetrahydro-pyran-4-yl)-phenyl]-amide

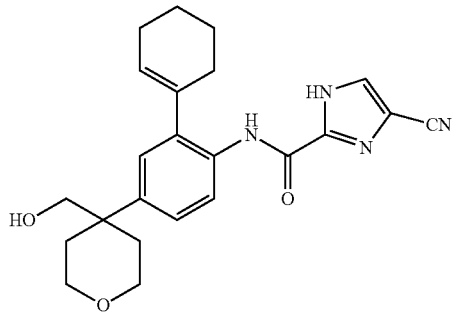 [SMILES: N#Cc1c[nH]c(C(=O)Nc2ccc(C3(CO)CCOCC3)cc2C2=CCCCC2)n1]

To a mixture of 4-{4-[(4-cyano-1H-imidazole-2-carbonyl)-amino]-3-cyclohex-1-enyl-phenyl}-tetrahydro-pyran-4-carboxylic acid (as prepared in Example 18, step (d), 20.0 mg, 0.0476 mmol) and triethylamine (Et₃N) (7.3 μL, 0.052 mmol) in 1 mL of THF at 0° C. was added ClCO₂Et (3.6 mg, 0.038 mmol). The mixture was stirred at RT for 0.5 h and NaBH₄ (5.4 mg, 0.14 mmol) was added. After stirring at RT for 16 h, the mixture was treated with 30 mL of EtOAc and 10 ml of 10% citric acid. The aqueous layer was separated and extracted with EtOAc (10 mL). The combined organic layers were washed with saturated NaHCO₃ aqueous solution (10 mL), H₂O (10 mL) and brine (10 mL). After drying over Na₂SO₄ and concentrating in vacuo, the residue was purified by silica gel chromatography (1-2% MeOH/DCM) to afford the title compound (14 mg, 70%) as a white solid. ¹H-NMR (1:5 CD₃OD/CDCl₃; 400 MHz): δ 8.24 (d, 1H, J=8.6 Hz), 7.72 (s, 1H), 7.26 (dd, 1H, J=8.6, 2.3 Hz), 7.14 (d, 1H, J=2.3 Hz), 5.84 (m, 1H), 3.82 (m, 2H), 3.57 (s, 2H), 3.54-3.60 (m, 2H), 2.27 (m, 4H), 2.14 (m, 2H), 1.95 (m, 2H), 1.82 (m, 4H). Mass spectrum (ESI, m/z): Calcd. for $C_{23}H_{26}N_4O_3$, 407.2 (M+H). found 407.1.

Example 21

4-Cyano-1H-imidazole-2-carboxylic acid [2-cyclohex-1-enyl-4-(4-morpholin-4-ylmethyl-tetrahydro-pyran-4-yl)-phenyl]-amide

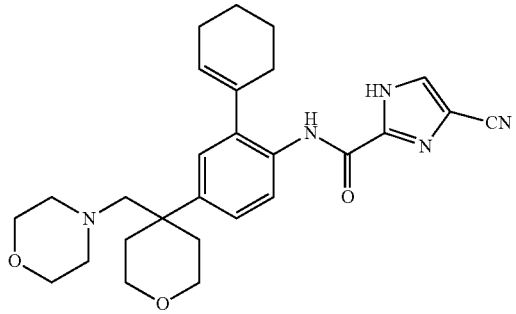 [SMILES: N#Cc1c[nH]c(C(=O)Nc2ccc(C3(CN4CCOCC4)CCOCC3)cc2C2=CCCCC2)n1]

a) 4-Cyano-1H-imidazole-2-carboxylic acid [2-cyclohex-1-enyl-4-(4-formyl-tetrahydro-pyran-4-yl)-phenyl]-amide

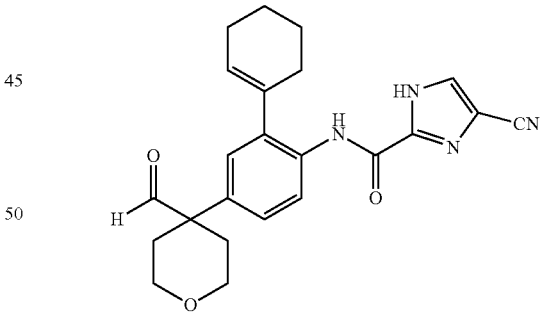

A mixture of 4-cyano-1H-imidazole-2-carboxylic acid [2-cyclohex-1-enyl-4-(4-hydroxymethyl-tetrahydro-pyran-4-yl)-phenyl]-amide (as prepared in Example 20, 75.4 mg, 0.185 mmol), Dess-Martin periodinane (157 mg, 0.369 mmol) and NaHCO₃ (155 mg, 1.85 mmol) in 3 mL of DCM was stirred at 0° C. for 0.5 h, at RT for 1 h. To the reaction was added 2 mL of 10% Na₂S₂O₃ and the resulting mixture was stirred vigorously for 5 min. The mixture was treated with 20 mL of H₂O and extracted with EtOAc (2×40 mL). The combined organic layers were washed with saturated NaHCO₃ aqueous solution (10 mL), H₂O (10 mL) and brine (10 mL). After drying over Na₂SO₄ and concentrating in vacuo, the residue was purified by silica gel chromatography (10-20%

EtOAc/DCM) to afford the title compound (45 mg, 60%) as a white solid. Mass spectrum (ESI, m/z): Calcd. for $C_{23}H_{24}N_4O_3$, 405.2 (M+H). found 405.1.

b) 4-Cyano-1H-imidazole-2-carboxylic acid [2-cyclohex-1-enyl-4-(4-morpholin-4-ylmethyl-tetrahydro-pyran-4-yl)-phenyl]-amide A mixture of 4-cyano-1H-imidazole-2-carboxylic acid [2-cyclohex-1-enyl-4-(4-formyl-tetrahydro-pyran-4-yl)-phenyl]-amide (as prepared in the previous step, 30.5 mg, 0.0754 mmol), morpholine (14 µL, 0.15 mmol) and sodium borohydride (6.0 mg, 0.16 mmol) in 2 mL of 1:1 DCM/THF was stirred at RT for 3 h. The mixture was then treated with saturated NaHCO₃ aqueous solution (10 mL) and extracted with EtOAc (3×10 mL). The combined organic layers were washed with H₂O (10 mL) and brine (10 mL). After drying over Na₂SO₄ and concentrating in vacuo, the residue was purified by silica gel chromatography (10-30% EtOAc/DCM) to afford the title compound (28 mg, 77%) as a white solid. ¹H-NMR (CDCl₃; 400 MHz): δ 12.61 (s, 1H), 9.66 (s, 1H), 8.31 (d, 1H, J=8.6 Hz), 7.76 (s, 1H), 7.28 (dd, 1H, J=8.6, 2.3 Hz), 7.17 (d, 1H, J=2.3 Hz), 5.86 (m, 1H), 3.79 (m, 2H), 3.59 (m, 2H), 3.53 (m, 4H), 2.45 (s, 2H), 2.29 (m, 4H), 2.13-2.21 (m, 6H), 1.77-1.98 (m, 6H). Mass spectrum (ESI, m/z): Calcd. for $C_{27}H_{33}N_5O_3$, 476.3 (M+H). found 476.2.

Example 22

4-Cyano-1H-imidazole-2-carboxylic acid {2-(4,4-dimethyl-cyclohex-1-enyl)-4-[4-(2H-tetrazol-5-yl)-tetrahydro-pyran-4-yl]-phenyl}-amide

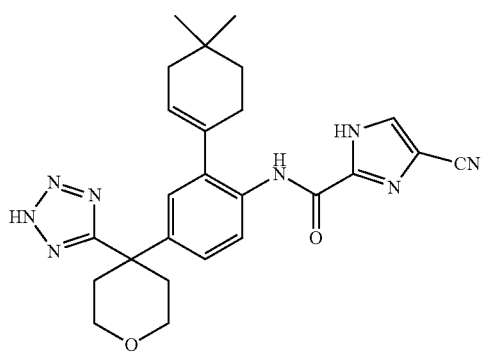 [SMILES: CC1(C)CC=C(c2cc(C3(c4nn[nH]n4)CCOCC3)ccc2NC(=O)c2nc(C#N)c[nH]2)CC1]

a) 4-(4-Nitro-phenyl)-tetrahydro-pyran-4-carboxylic acid

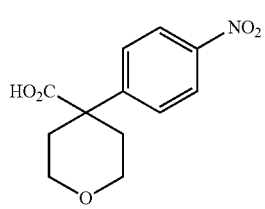 [SMILES: O=C(O)C1(c2ccc([N+](=O)[O-])cc2)CCOCC1]

The title compound was prepared by the procedure of Example 17 using 4-(4-nitro-phenyl)-tetrahydro-pyran-4-carboxylic acid methyl ester (as prepared in the Example 16, step (a), 531 mg, 2.00 mmol) to afford 465 mg (92%) of a white solid. ¹H-NMR (CD₃OD; 400 MHz): δ 8.24 (d, 1H, J=9.1 Hz), 7.70 (d, 1H, J=9.1 Hz), 3.93 (ddd, 2H, J=11.9, 3.8, 3.5 Hz), 3.64 (ddd, 2H, J=11.9, 11.1, 2.3 Hz), 2.55 (m, 2H), 1.98 (m, 2H).

b) 4-(4-Nitro-phenyl)-tetrahydro-pyran-4-carbonitrile

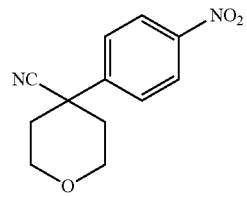 [SMILES: N#CC1(c2ccc([N+](=O)[O-])cc2)CCOCC1]

To a mixture of 4-(4-nitro-phenyl)-tetrahydro-pyran-4-carboxylic acid (as prepared in the previous step, 251 mg, 1.00 mmol) and sulfonamide (115 mg, 1.20 mmol) in 1 mL of sulfolane was added thionyl chloride (80 µL, 1.10 mmol). The resulting mixture was stirred at 120° C. for 16 h. After cooling to 0° C., the mixture was neutralized to pH 7 with 1 N NaOH solution and treated with 30 mL of EtOAc. The organic layer was separated and washed with H₂O (2×10 mL) and brine (10 mL). After drying over Na₂SO₄ and concentrating in vacuo, the residue was purified by silica gel chromatography (3:7 hexane/DCM) to afford the title compound (223 mg, 96%) as a faint yellow solid. ¹H-NMR (CDCl₃; 400 MHz): δ 8.30 (d, 1H, J=9.1 Hz), 7.56 (d, 1H, J=9.1 Hz), 4.13 (m, 2H), 3.93 (m, 2H), 2.17 (m, 2H), 2.07 (m, 2H).

c) 4-(4-Amino-phenyl)-tetrahydro-pyran-4-carbonitrile

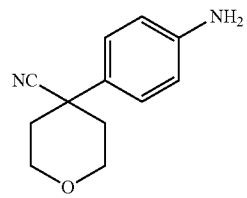

A mixture of 4-(4-nitro-phenyl)-tetrahydro-pyran-4-carbonitrile (as prepared in the previous step, 223 mg, 0.960 mmol) and 10% Pd/C (112 mg, 50 wt %) in 10 mL of MeOH was stirred at RT under H₂ (balloon pressure) for 1 h. The Pd catalyst was removed by filtration on Celite and the filtrate was concentrated to give 195 mg (100%) of the title compound as a faint yellow solid. Mass spectrum (ESI, m/z): Calcd. for $C_{12}H_{14}N_2O$, 203.1 (M+H). found 203.2.

d) 4-(4-Amino-3-bromo-phenyl)-tetrahydro-pyran-4-carbonitrile

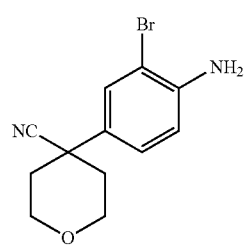 [SMILES: N#CC1(c2ccc(N)c(Br)c2)CCOCC1]

The title compound was prepared by the procedure of Example 16, step (c) using 4-(4-amino-phenyl)-tetrahydro-pyran-4-carbonitrile (as prepared in the previous step, 195 mg, 0.964 mmol). Silica gel chromatography (20% EtOAc/hexane) afforded the title compound (166 mg, 61%) as a white solid. Mass spectrum (ESI, m/z): Calcd. for $C_{12}H_{13}BrN_2O$, 281.0 (M+H). found 281.2.

e) 2-Bromo-4-[4-(2H-tetrazol-5-yl)-tetrahydro-pyran-4-yl]-phenylamine

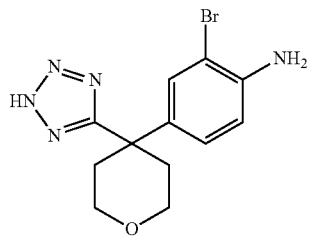 [SMILES: Nc1ccc(C2(c3nn[nH]n3)CCOCC2)cc1Br]

A mixture of 4-(4-amino-3-bromo-phenyl)-tetrahydro-pyran-4-carbonitrile (as prepared in the previous step, 141 mg, 0.500 mmol), trimethylsilylazide (133 µL, 1.00 mmol) and tetrabutylammonium fluoride (65 mg, 0.25 mmol) was stirred at 120° C. for 18 h under Ar. After cooling to RT, the mixture was treated with 30 mL of EtOAc and washed with $H_2O$ (2×10 mL), 15% citric acid aqueous solution (3×10 mL) and brine (10 mL). After drying over $Na_2SO_4$, the organic layer was concentrated in vacuo to afford the title compound (147 mg, 91%) as a faint yellow solid. Mass spectrum (ESI, m/z): Calcd. for $C_{12}H_{14}BrN_5O$, 324.0 (M+H). found 324.1.

f) 4-Cyano-1-(2-trimethylsilanyl-ethoxymethyl)-1H-imidazole-2-carboxylic acid {2-(4,4-dimethyl-cyclohex-1-enyl)-4-[4-(2H-tetrazol-5-yl)-tetrahydro-pyran-4-yl]-phenyl}-amide

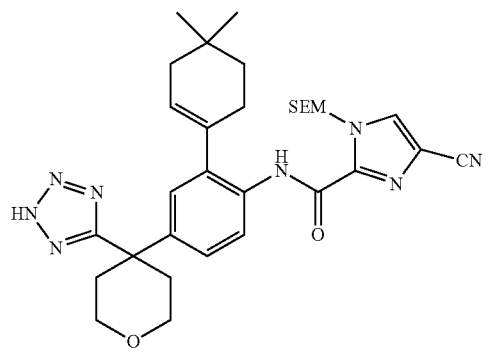 [SMILES: CC1(C)CC=C(c2cc(C3(c4nn[nH]n4)CCOCC3)ccc2NC(=O)c2nc(C#N)cn2COCC[Si](C)(C)C)CC1]

To a mixture of 2-bromo-4-[4-(2H-tetrazol-5-yl)-tetrahydro-pyran-4-yl]-phenylamine (70.0 mg, 0.216 mmol), 4,4-dimethylcyclohexen-1-ylboronic acid (36.6 mg, 0.238 mmol) and $Pd(PPh_3)_4$ (25.0 mg, 0.0216 mmol) in 2 mL of 1,4-dioxane was added 2.0 M aqueous $Na_2CO_3$ solution (0.85 mL, 1.7 mmol). The resulting mixture was stirred at 80° C. for 2 d under Ar. After cooling to RT, the reaction was treated with $H_2O$ (20 mL) and washed with EtOAc (2×10 mL). The aqueous mixture was neutralized to PH 6 with 15% citric acid aqueous solution and extracted with EtOAc (3×10 mL). The combined organic layers were dried over $Na_2SO_4$ and concentrated in vacuo to afford 76 mg of a crude product of 2-(4,4-dimethyl-cyclohex-1-enyl)-4-[4-(2H-tetrazol-5-yl)-tetrahydro-pyran-4-yl]-phenylamine as a brown oil. The product was used for next experiment immediately without further purification.

To the crude product of 2-(4,4-dimethyl-cyclohex-1-enyl)-4-[4-(2H-tetrazol-5-yl)-tetrahydro-pyran-4-yl]-phenylamine (76 mg, ca. 0.22 mmol) in 2.5 mL of DMF was added potassium 4-cyano-1-(2-trimethylsilanyl-ethoxymethyl)-1H-imidazole-2-carboxylate (as prepared in Example 1, step (d), 72 mg, 0.24 mmol), PyBroP (110 mg, 0.236 mmol) and DIEA (112 µL, 0.645 mmol). After stirring at RT for 2 d, the mixture was treated with 20 mL of $H_2O$ and extracted with EtOAc (2×20 mL). The combined organic layers were washed with $H_2O$ (2×10 mL) and brine (10 mL). After drying over $Na_2SO_4$ and concentrating in vacuo, the residue was purified by silica gel chromatography (1-3 MeOH/DCM) to afford the title compound (55 mg, 42% for 2 steps) as a faint brown solid. Mass spectrum (ESI, m/z): Calcd. for $C_{31}H_{42}N_8O_3Si$, 603.3 (M+H). found 602.9.

g) 4-Cyano-1H-imidazole-2-carboxylic acid {2-(4,4-dimethyl-cyclohex-1-enyl)-4-[4-(2H-tetrazol-5-yl)-tetrahydro-pyran-4-yl]-phenyl}-amide The title compound was prepared by the procedure of Example 11, step (g) using 4-cyano-1-(2-trimethylsilanyl-ethoxymethyl)-1H-imidazole-2-carboxylic acid {2-(4,4-dimethyl-cyclohex-1-enyl)-4-[4-(2H-tetrazol-5-yl)-tetrahydro-pyran-4-yl]-phenyl}-amide (as prepared in the previous step, 51.2 mg, 0.0850 mmol). Silica gel chromatography (1-4% MeOH/DCM) afforded the title compound (17 mg, 43%) as a white solid. $^1$H-NMR (CD$_3$OD; 400 MHz): δ 8.26 (d, 1H, J=8.6 Hz), 7.90 (s, 1H), 7.22 (dd, 1H, J=8.6, 2.3 Hz), 7.12 (d, 1H, J=2.3 Hz), 5.73 (m, 1H), 3.95 (m, 2H), 3.54 (m, 2H), 2.70 (m, 2H), 2.42 (m, 2H), 2.26 (m, 2H), 2.08 (m, 2H), 1.58 (t, 2H, J=6.3 Hz), 1.09 (s, 6H). Mass spectrum (ESI, m/z): Calcd. for $C_{25}H_{28}N_8O_2$, 473.2 (M+H). found 473.2.

Example 23

4-[4-[(4-Cyano-1H-pyrrole-2-carbonyl)-amino]-3-(4,4-dimethyl-cyclohex-1-enyl)-phenyl]-tetrahydro-pyran-4-carboxylic acid

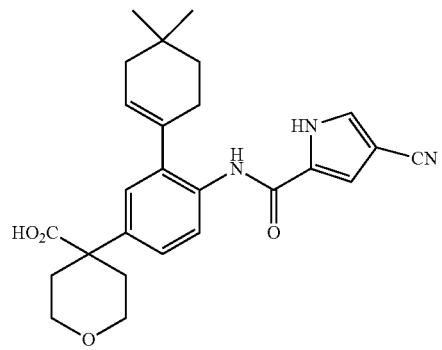 [SMILES: CC1(C)CC=C(c2cc(C3(C(=O)O)CCOCC3)ccc2NC(=O)c2cc(C#N)c[nH]2)CC1]

a) 4-[4-[(4-Cyano-1H-pyrrole-2-carbonyl)-amino]-3-(4,4-dimethyl-cyclohex-1-enyl)-phenyl]-tetrahydro-pyran-4-carboxylic acid methyl ester

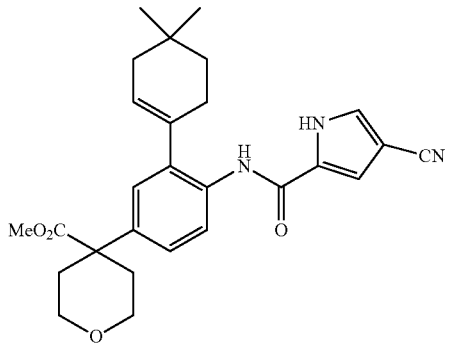 [SMILES: COC(=O)C1(c2ccc(NC(=O)c3cc(C#N)c[nH]3)c(C3=CCC(C)(C)CC3)c2)CCOCC1]

A solution of 4-[4-amino-3-(4,4-dimethyl-cyclohex-1-enyl)-phenyl]-tetrahydro-pyran-4-carboxylic acid methyl ester (as prepared in Example 16, step (d), 68.7 mg, 0.200 mmol), 4-cyano-1H-pyrrole-2-carboxylic acid (*Canadian J. Chem.* 59, 2673 (1981), 40.8 mg, 0.300 mmol), 1-(3-dimethylaminopropyl)-3-ethylcarbodiimide hydrochloride (EDCI) (57.5 mg, 0.300 mmol), hydroxybenzotriazole (HOBt) (40.5 mg, 0.300 mmol) and DIEA (105 µL, 0.600 mmol) in 2.5 mL of DMF was stirred at RT for 2 d under Ar. The resulting mixture was treated with H$_2$O (20 mL) and extracted with EtOAc (2×25 mL). The combined organic layers were washed with H$_2$O (10 mL) and brine (10 mL). After drying over Na$_2$SO$_4$ and concentrating in vacuo, the residue was purified by silica gel chromatography (10-20% EtOAc/DCM) to afford the title compound (46 mg, 50%) as a white solid. Mass spectrum (ESI, m/z): Calcd. for C$_{27}$H$_{31}$N$_3$O$_4$, 462.2 (M+H). found 462.2.

b) 4-[4-[(4-Cyano-1H-pyrrole-2-carbonyl)-amino]-3-(4,4-dimethyl-cyclohex-1-enyl)-phenyl]-tetrahydro-pyran-4-carboxylic acid The title compound was prepared by the procedure of Example 17 using 4-[4-[(4-cyano-1H-pyrrole-2-carbonyl)-amino]-3-(4,4-dimethyl-cyclohex-1-enyl)-phenyl]-tetrahydro-pyran-4-carboxylic acid methyl ester (as prepared in the previous step, 28.0 mg, 0.0607 mmol). The title compound (11.1 mg, 41%) is a white solid. $^1$H-NMR (1:1 CDCl$_3$/CD$_3$OD; 400 MHz): δ 7.65 (d, 1H, J=8.6 Hz), 7.51 (d, 1H, J=1.5 Hz), 7.36 (dd, 1H, J=8.6, 2.3 Hz), 7.26 (d, 1H, J=2.3 Hz), 7.04 (s, 1H), 5.69 (m, 1H), 3.94 (m, 2H), 3.65 (m, 2H), 2.53 (m, 2H), 2.29 (m, 2H), 1.91-2.01 (m, 4H), 1.50 (t, 2H, J=6.3 Hz), 0.98 (s, 6H). Mass spectrum (ESI, m/z): Calcd. for C$_{26}$H$_{29}$N$_3$O$_4$, 448.2 (M+H). found 448.2.

Example 24

4-Cyano-1H-imidazole-2-carboxylic acid [4-(4-carbamoyl-tetrahydro-pyran-4-yl)-2-(4,4-dimethyl-cyclohex-1-enyl)-phenyl]-amide

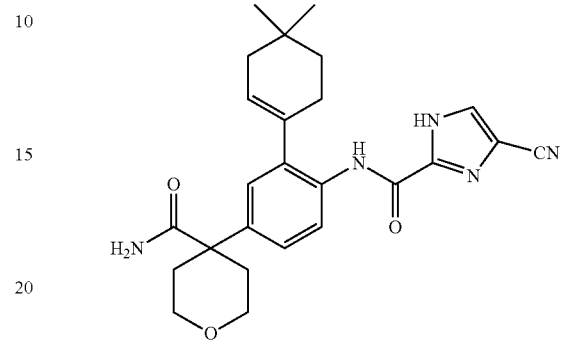

The title compound was prepared by the procedure of Example 19 using 4-[4-[(4-cyano-1H-imidazole-2-carbonyl)-amino]-3-(4,4-dimethyl-cyclohex-1-enyl)-phenyl]-tetrahydro-pyran-4-carboxylic acid (as prepared in Example 17, 13.0 mg, 0.0290 mmol). Silica gel chromatography (5% MeOH/DCM) afforded the title compound (4.0 mg, 31%) as a white solid. $^1$H-NMR (CD$_3$OD; 400 MHz): δ 8.27 (d, 1H, J=8.6 Hz), 7.91 (s, 1H), 7.35 (dd, 1H, J=8.6, 2.3 Hz), 7.24 (d, 1H, J=2.3 Hz), 5.76 (m, 1H), 3.81-3.89 (m, 2H), 3.68-3.76 (m, 2H), 2.42-2.50 (m, 2H), 2.26-2.36 (m, 2H), 1.98-2.12 (m, 4H), 1.60 (t, 2H, J=6.3 Hz), 1.10 (s, 6H). Mass spectrum (ESI, m/z): Calcd. for C$_{25}$H$_{29}$N$_5$O$_3$, 448.2 (M+H). found 448.2.

Example 25

4-Cyano-1H-imidazole-2-carboxylic acid [2-(4,4-dimethyl-cyclohex-1-enyl)-4-(4-hydroxymethyl-tetrahydro-pyran-4-yl)-phenyl]-amide

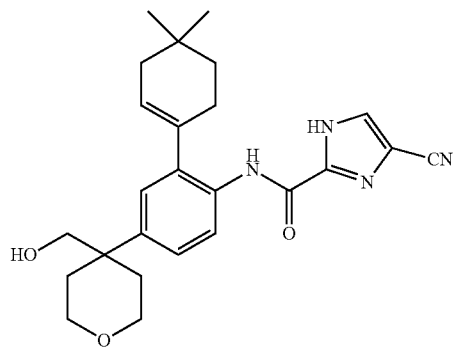 [SMILES: CC1(C)CC=C(c2cc(C3(CO)CCOCC3)ccc2NC(=O)c2nc(C#N)c[nH]2)CC1]

To a mixture of 4-[4-[(4-cyano-1H-pyrrole-2-carbonyl)-amino]-3-(4,4-dimethyl-cyclohex-1-enyl)-phenyl]-tetrahydro-pyran-4-carboxylic acid methyl ester (as prepared in the Example 16, step (f), 300 mg, 0.649 mmol) and NaBH$_4$ (123 mg, 3.24 mmol) in 10 mL of t-BuOH at 80° C. was added MeOH (1.30 mL) over 20 min. The resulting mixture was stirred at 80° C. for 32 h under Ar. After cooling to RT, the mixture was treated with 15% citric acid aqueous solution until a pH of 5. The mixture was then treated with 30 mL of H$_2$O and extracted with EtOAc (3×20 mL). The combined organic layers were washed with H$_2$O (20 mL), brine (10 mL), dried (Na$_2$SO$_4$) and concentrated in vacuo. The residue was purified by flash chromatography on silica gel with 2-3% MeOH/DCM to afford 107 mg (38%) of the title compound as a white solid: δ 8.19 (d, 1H, J=8.6 Hz), 7.95 (s, 1H), 7.31 (dd, 1H, J=8.6, 2.3 Hz), 7.19 (d, 1H, J=2.3 Hz), 5.75 (m, 1H), 3.80 (m, 2H), 3.47-3.57 (m, 2H), 3.52 (s, 2H), 2.32 (m, 2H), 2.05-2.17 (m, 4H), 1.90-1.99 (m, 2H), 1.59 (t, 2H, J=6.3 Hz), 1.08 (s, 6H). Mass Spectrum (ESI, m/z): Calcd. for C$_{25}$H$_{30}$N$_4$O$_3$, 435.2 (M+H). found 435.1.

Example 26

4-Cyano-1H-imidazole-2-carboxylic acid [2-(4,4-dimethyl-cyclohex-1-enyl)-4-(4-morpholin-4-ylm-ethyl-tetrahydro-pyran-4-yl)-phenyl]-amide

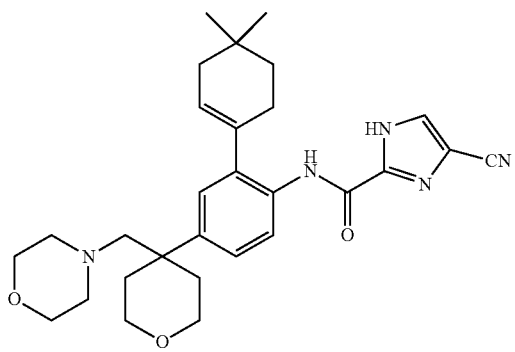 [SMILES: CC1(C)CC=C(c2cc(C3(CN4CCOCC4)CCOCC3)ccc2NC(=O)c2nc(C#N)c[nH]2)CC1]

a) 4-Cyano-1H-imidazole-2-carboxylic acid [2-(4,4-dimethyl-cyclohex-1-enyl)-4-(4-formyl-tetrahydro-pyran-4-yl)-phenyl]-amide The title compound was prepared by the procedure of Example 21, step (a) using 4-cyano-1H-imidazole-2-carboxylic acid [2-(4,4-dimethyl-cyclohex-1-enyl)-4-(4-hydroxymethyl-tetrahydro-pyran-4-yl)-phenyl]-amide (as prepared in Example 25, 40.0 mg, 0.0921 mmol) and Dess-Martin periodinane (80.5 mg, 0.184 mmol). The title compound (40 mg, 100%) was obtained as a white solid and used in the next step without further purification. Mass spectrum (ESI, m/z): Calcd. for C$_{25}$H$_{28}$N$_4$O$_3$, 433.2 (M+H). found 433.4.

b) 4-Cyano-1H-imidazole-2-carboxylic acid [2-(4,4-dimethyl-cyclohex-1-enyl)-4-(4-morpholin-4-ylm-ethyl-tetrahydro-pyran-4-yl)-phenyl]-amide The title compound was prepared by the procedure of Example 21, step (b) using 4-cyano-1H-imidazole-2-carboxylic acid [2-(4,4-dimethyl-cyclohex-1-enyl)-4-(4-formyl-tetrahydro-pyran-4-yl)-phenyl]-amide (as prepared in the previous step, 40.0 mg, 0.0921 mmol), morpholine (13 μL, 0.14 mmol) and sodium triacetoxyborohydride (5.2 mg, 0.14 mmol). Silica gel chromatography (10-20% EtOAc/DCM then 1-2% MeOH/DCM) afforded the title compound (20 mg, 43%) as a white solid. $^1$H-NMR (CDCl$_3$; 400 MHz): δ 12.61 (s, 1H), 9.70 (s, 1H), 8.33 (d, 1H, J=8.6 Hz), 7.75 (s, 1H), 7.28 (dd, 1H, J=8.6, 2.3 Hz), 7.16 (d, 1H, J=2.3 Hz), 5.78 (m, 1H), 3.79 (m, 2H), 3.59 (m, 2H), 3.50-3.62 (m, 4H), 2.45 (s, 2H), 2.25-2.31 (m, 2H), 2.11-2.22 (m, 8H), 1.93 (m, 2H), 1.61 (t, 2H, J=6.3 Hz), 1.13 (s, 6H). Mass spectrum (ESI, m/z): Calcd. for C$_{29}$H$_{37}$N$_5$O$_3$, 504.3 (M+H). found 504.3.

The following compounds have been prepared according to the examples as indicated:

| Example No. | Name | Structure | Procedure Reference | Mass Spectrum |
|---|---|---|---|---|
| 27 | 4-Cyano-1H-imidazole-2-carboxylic acid [2-cyclohex-1-enyl-4-(4-hydroxy-tetrahydro-pyran-4-yl)-phenyl]-amide | 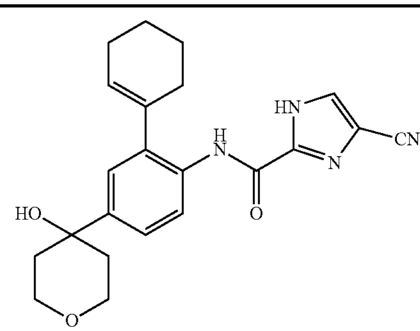 | Example 14, step (d) | (ESI, m/z) Calcd. for C$_{22}$H$_{24}$N$_4$O$_3$, 393.2 (M + H), found 393.1. |

| Example No. | Name | Structure | Procedure Reference | Mass Spectrum |
|---|---|---|---|---|
| 28 | 4-Cyano-1H-imidazole-2-carboxylic acid [2-cyclohex-1-enyl-4-(4dimethylcarbamoyl-tetrahydro-pyran-4-yl)-phenyl]-amide | 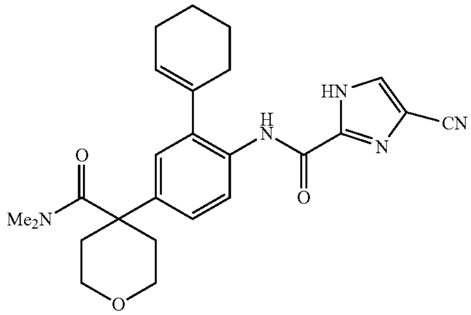 [SMILES: CN(C)C(=O)C1(c2ccc(NC(=O)c3nc(C#N)c[nH]3)c(C3=CCCCC3)c2)CCOCC1] | Example 19 | (ESI, m/z) Calcd. for $C_{25}H_{29}N_5O_3$, 448.2 (M + H), found 448.2. |
| 29 | 4-Cyano-1H-imidazole-2-carboxylic acid [4-(4-dimethylcarbamoyl-tetrahydro-pyran-4-yl)-2-(4,4-dimethyl-cyclohex-1-enyl)-phenyl]-amide | 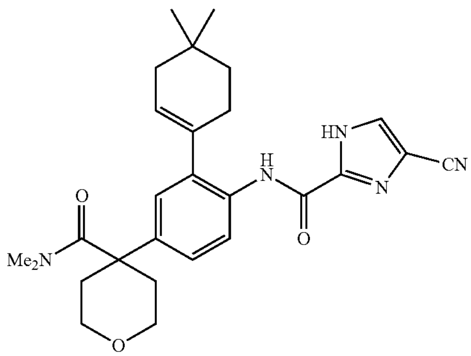 [SMILES: CN(C)C(=O)C1(c2ccc(NC(=O)c3nc(C#N)c[nH]3)c(C3=CCC(C)(C)CC3)c2)CCOCC1] | Example 24 | (ESI, m/z) Calcd. for $C_{27}H_{33}N_5O_3$, 476.3 (M + H), found 476.2. |

Examples 30 and 31

4-Cyano-1H-imidazole-2-carboxylic acid [2-(4,4-dimethyl-cyclohex-1-enyl)-4-(cis-4-hydroxy-cis-2,6-dimethyl-tetrahydro-pyran-4-yl)-phenyl]-amide and 4-cyano-1H-imidazole-2-carboxylic acid [2-(4,4-dimethyl-cyclohex-1-enyl)-4-(trans-4-hydroxy-cis-2,6-dimethyl-tetrahydro-pyran-4-yl)-phenyl]-amide

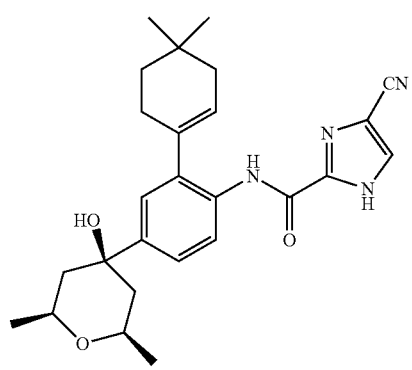

31

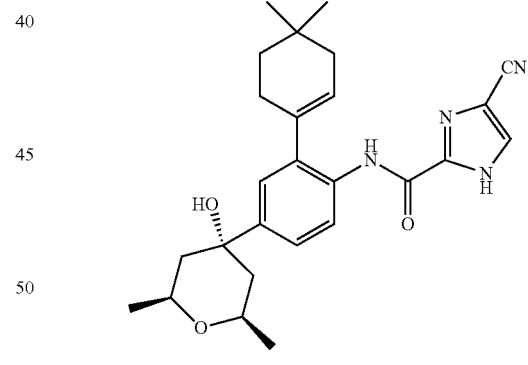

32

The title compounds were prepared as described in Example 1, step (h) using 4-cyano-1H-imidazole-2-carboxylic acid [4-bromo-2-(4,4-dimethyl-cyclohex-1-enyl)-phenyl]-amide (as prepared in Example 1 (step g)) and cis-2,6-dimethyltetrahydropyran-4-one (*Monatshefte fuer Chemie*, 136(7), 1197-1203, (2005)).

31: Mass spectrum (ESI, m/z): Calcd. for $C_{26}H_{32}N_4O_3$, 449.2 (M+H). found 449.2.

32: Mass spectrum (ESI, m/z): Calcd. for $C_{26}H_{32}N_4O_3$, 449.2 (M+H). found 449.2.

Example 32

4-Cyano-1H-imidazole-2-carboxylic acid [2-(4,4-dimethyl-cyclohex-1-enyl)-6-(4-hydroxy-Cis-2,6-dimethyl-tetrahydro-pyran-4-yl)-pyridin-3-yl]-amide

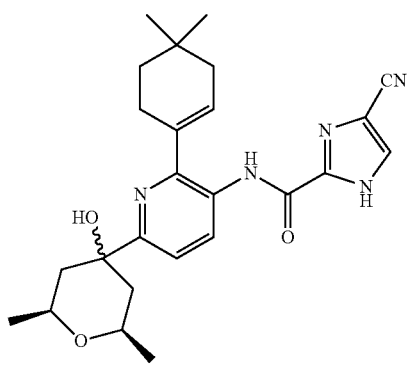 [SMILES: C[C@@H]1CC(O)(c2ccc(NC(=O)c3nc(C#N)c[nH]3)c(C3=CCC(C)(C)CC3)n2)C[C@H](C)O1]

a) 6-Bromo-2-iodo-pyridin-3-ylamine

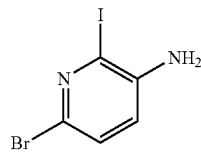

To a stirred solution of 6-bromo-pyridin-3-ylamine (10.2 g, 0.0580 mol) and Ag$_2$SO$_4$ (18.1 g, 0.0580 mol) in EtOH (150 mL) was added I$_2$ (7.59 g, 0.0580 mol) and the reaction was allowed to stir overnight. At this time hexane (200 mL) was added and the resultant mixture was filtered through Celite. The solvent was removed in vacuo, dissolved in CHCl$_3$ (200 mL), washed with aqueous saturated Na$_2$S$_2$O$_3$ (100 mL), water (1×100 mL), and dried (Na$_2$SO$_4$). The solvent was concentrated in vacuo and the residue was dissolved in hot EtOAc (100 mL), filtered and treated with hexanes (100 mL). Filtration gave 11.2 g (65%) of 6-bromo-2-iodo-pyridin-3-ylamine as a white crystalline material. $^1$H-NMR (CDCl$_3$; 400 MHz): δ 7.10 (d, 1H, J=8.2 Hz), 6.74 (d, 1H, J=8.2 Hz), 4.06 (br s, 2H).

b) 6-Bromo-2-(4,4-dimethyl-cyclohex-1-enyl)-pyridin-3-ylamine

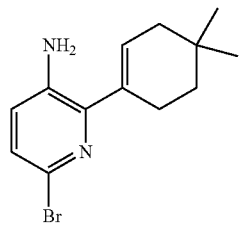 [SMILES: CC1(C)CC=C(c2nc(Br)ccc2N)CC1]

A solution of 6-bromo-2-iodo-pyridin-3-ylamine (as prepared in the previous step, 1.00 g, 3.35 mmol) in toluene (27 mL) and EtOH (13.5 mL) was treated with 2.0 M aq Na$_2$CO$_3$ (13.4 mL, 26.8 mmol) and 4,4-dimethyl-cyclohex-1-enylboronic acid (567 mg, 3.68 mmol). The mixture was degassed via sonication, placed under Ar, treated with Pd(PPh$_3$)$_4$ (271 mg, 0.234 mmol), and heated to 80° C. for 5 h. The cooled mixture was diluted with EtOAc (100 mL) and washed with water (2×50 mL). The combined aqueous layers were extracted with EtOAc (1×100 mL). The combined organic layers were dried over MgSO$_4$ and concentrated in vacuo. Silica gel chromatography of the residue on a Varian Mega-Bond Elut 50-g column with 10% EtOAc-hexane afforded 668 mg (71%) of 6-bromo-2-(4,4-dimethyl-cyclohex-1-enyl)-pyridin-3-ylamine as a tan solid. $^1$H-NMR (CDCl$_3$; 400 MHz): δ 7.06 (d, 1H, J=8.3 Hz), 6.85 (d, 1H, J=8.3 Hz), 5.95 (m, 1H), 3.86 (br s, 2H), 2.43-2.39 (m, 2H), 1.99-1.97 (m, 2H), 1.51 (t, 2H, J=6.4 Hz), 0.99 (s, 6H).

c) 4-Cyano-1-(2-trimethylsilanyl-ethoxymethyl)-1H-imidazole-2-carboxylic acid [6-bromo-2-(4,4-dimethyl-cyclohex-1-enyl)-pyridin-3-yl]-amide

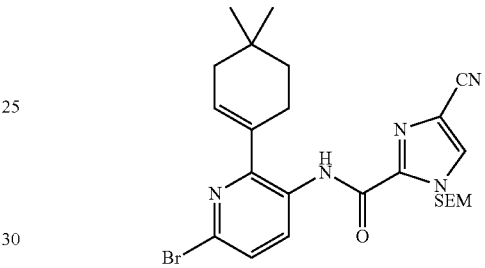

The title compound was prepared from 6-bromo-2-(4,4-dimethyl-cyclohex-1-enyl)-pyridin-3-ylamine (as prepared in the previous step, 60 mg, 0.21 mmol), potassium 4-cyano-1-(2-trimethylsilanyl-ethoxymethyl)-1H-imidazole-2-carboxylate (as prepared in Example 1, step (d), 91.0 mg, 0.290 mmol), PyBroP (157 mg, 0.330 mmol) and DIEA (91.0 µL, 0.520 mmol) according to the procedure in Example 1, step (f) (84 mg, 78%). $^1$H-NMR (CDCl$_3$; 400 MHz): δ 9.91 (s, 1H), 8.64 (d, 1H, J=8.6 Hz), 7.79 (s, 1H), 7.38 (d, 1H, J=8.6 Hz), 6.00 (m, 1H), 5.92 (s, 2H), 3.67 (m, 2H), 2.46 (m, 2H), 2.14 (m, 2H), 1.62 (t, 2H, J=6.3 Hz), 1.12 (s, 6H), 0.98 (m, 2H).

d) 5-Cyano-1H-imidazole-2-carboxylic acid [6-bromo-2-(4,4-dimethyl-cyclohex-1-enyl)-pyridin-3-yl]-amide

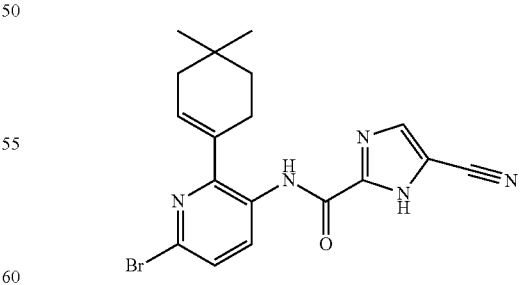

The title compound was prepared from 4-cyano-1-(2-trimethylsilanyl-ethoxymethyl)-1H-imidazole-2-carboxylic acid [6-bromo-2-(4,4-dimethyl-cyclohex-1-enyl)-pyridin-3-yl]-amide (as prepared in the previous step) according to the procedure in Example 1, step (g). $^1$H-NMR (CD$_3$OD; 400 MHz): δ 8.53 (d, 1H, J=8.8 Hz), 8.03 (s, 1H), 7.48 (d, 1H, J=8.8 Hz), 6.04-5.99 (m, 1H), 2.48-2.40 (m, 2H), 2.13-2.08 (m, 2H), 1.61 (t, 2H, J=6.0 Hz), 1.09 (s, 6H). Mass spectrum (ESI, m/z): Calcd. for $C_{18}H_{18}BrN_5O$, 400.1 (M+H). found 400.0.

e) 4-Cyano-1H-imidazole-2-carboxylic acid [2-(4,4-dimethyl-cyclohex-1-enyl)-6-(4-hydroxy-cis-2,6-dimethyl-tetrahydro-pyran-4-yl)-pyridin-3-yl]-amide The title compound was prepared as described in Example 1, step (h) using 4-cyano-1H-imidazole-2-carboxylic acid [4-bromo-2-(4,4-dimethyl-cyclohex-1-enyl)-pyridin-3-yl]-amide (as prepared in the previous step) and cis-2,6-dimethyltertahydopyran-4-one (*Monatshefte fuer Chemie*, 136(7), 1197-1203, (2005)).

Mass spectrum (ESI, m/z): Calcd. for $C_{25}H_{31}N_5O_3$, 450.2 (M+H). found 450.2.

Example 33

4-Cyano-1H-imidazole-2-carboxylic acid [2-(4,4-dimethyl-cyclohex-1-enyl)-6-(4-hydroxy-tetrahydro-pyran-4-yl)-pyridin-3-yl]-amide

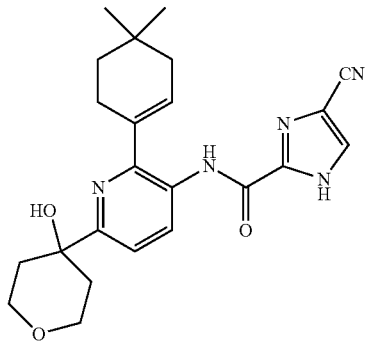 [SMILES: CC1(C)CC=C(c2nc(C3(O)CCOCC3)ccc2NC(=O)c2nc(C#N)c[nH]2)CC1]

The title compound was prepared as described in Example 1 step (h) using 4-cyano-1H-imidazole-2-carboxylic acid [4-bromo-2-(4,4-dimethyl-cyclohex-1-enyl)-pyridine-3-yl]-amide (as prepared in the Example 32 steps (d)) and tetrahydropyran-4-one. Mass spectrum (ESI, m/z): Calcd. for $C_{25}H_{27}N_5O_3$, 422.2 (M+H). found 422.2.

Example 34

5-Cyano-1H-imidazole-2-carboxylic acid [2-cyclohex-1-enyl-4-(4-methanesulfonyl-tetrahydro-pyran-4-yl)-phenyl]-amide

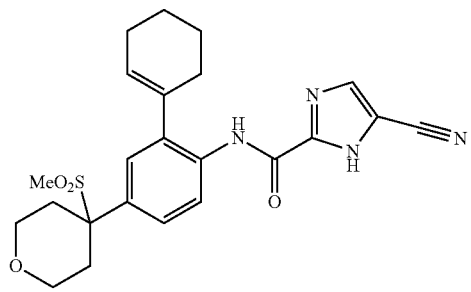 [SMILES: CS(=O)(=O)C1(c2ccc(NC(=O)c3ncc(C#N)[nH]3)c(C3=CCCCC3)c2)CCOCC1]

To a mixture of 5-cyano-1H-imidazole-2-carboxylic acid [2-cyclohex-1-enyl-4-(4-hydroxy-tetrahydro-pyran-4-yl)-phenyl]-amide (as prepared in Example 27, 75 mg, 0.19 mmol) and sodium methylsulfinate (195 mg, 1.90 mmol) in 4 mL of methanol was added 0.28 mL (3.80 mmol) of TFA. The mixture was stirred overnight at 70° C. and then concentrated in vacuo. The crude residue was partitioned in EtOAc (20 mL) and saturated aqueous $NaHCO_3$ (20 mL). The organic layer was dried ($Na_2SO_4$) and then concentrated in vacuo. The residue was purified by preparative TLC on silica gel (20% ethyl acetate-hexane) to afford the title compound as a light brown oil (18 mg, 21%). $^1$H-NMR ($CDCl_3$; 400 MHz): δ 9.64 (s, 1H), 8.32 (d, 1H, J=8.0), 7.71 (s, 1H), 7.33 (m, 1H), 7.23 (d, 1H, J=1.8 Hz), 5.87 (s, 1H), 3.90-3.81 (m, 4H), 3.01 (s, 3H), 2.30-2.25 (m, 4H), 2.07-1.79 (m, 8H).

Example 35

4-Cyano-1H-imidazole-2-carboxylic acid [4-(1-acetyl-4-hydroxy-piperidin-4-yl)-2-(4,4-dimethyl-cyclohex-1-enyl)-phenyl]-amide

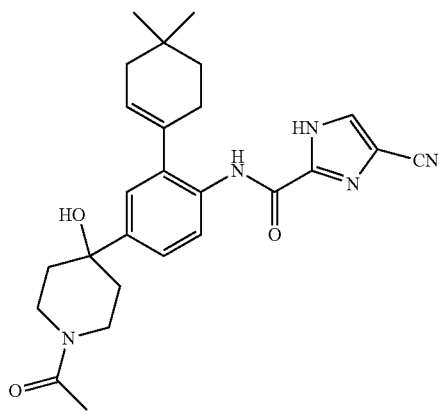 [SMILES: CC(=O)N1CCC(O)(c2ccc(NC(=O)c3nc(C#N)c[nH]3)c(C3=CCC(C)(C)CC3)c2)CC1]

The title compound was prepared by the procedure of Example 11 using 4-cyano-1H-imidazole-2-carboxylic acid [4-bromo-2-(4,4-dimethyl-cyclohex-1-enyl)-phenyl]-amide (as prepared in Example 1, step (g), 80.0 mg, 0.200 mmol) and 1-acetyl-piperidin-4-one (123 µL, 1.00 mmol). Silica gel chromatography (2-5% MeOH/DCM) afforded the title compound (59.1 mg, 64%) as a colorless oil. $^1$H-NMR ($CD_3OD$; 400 MHz): δ 8.18 (d, 1H, J=8.6 Hz), 8.00 (s, 1H), 7.39 (dd, 1H, J=8.6, 2.3 Hz), 7.35 (d, 1H, J=2.3 Hz), 5.74 (m, 1H), 4.45 (m, 1H), 3.84 (m, 1H), 3.60 (m, 1H), 3.11 (m, 1H), 2.28-2.35 (m, 2H), 2.15 (s, 3H), 1.91-2.10 (m, 4H), 1.76 (m, 2H), 1.59 (t, 2H, J=6.3 Hz), 1.09 (s, 6H). Mass spectrum (ESI, m/z): Calcd. for $C_{26}H_{31}N_5O_3$, 462.2 (M+H). found 462.0.

The following examples are produced according to procedures of previous examples with the corresponding reagents as indicated in the table below:

| Example No. | Name | Structure | Procedure Reference | Reagents |
|---|---|---|---|---|
| 36 | 4-Cyano-1H-imidazole-2-carboxylic acid {2-(4,4-dimethyl-cyclohex-1-enyl)-4-[4-(2-pyrrolidin-1-yl-ethylamino)-tetrahydro-pyran-4-yl]-phenyl}-amide | 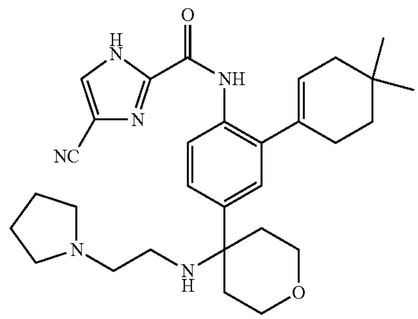 [SMILES: CC1(C)CC=C(c2cc(C3(NCCN4CCCC4)CCOCC3)ccc2NC(=O)c2nc(C#N)c[nH]2)CC1] | Example 4 | |
| 37 | 4-Cyano-1H-imidazole-2-carboxylic acid [4-[4-(2-acetylamino-ethylamino)-tetrahydro-pyran-4-yl]-2-(4,4-dimethyl-cyclohex-1-enyl)-phenyl]-amide | 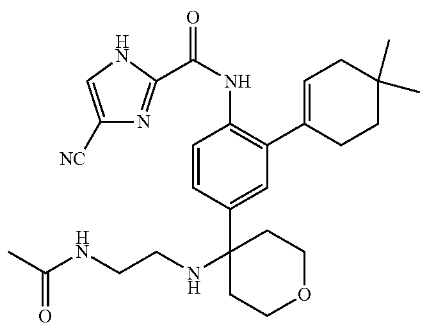 [SMILES: CC(=O)NCCNC1(c2ccc(NC(=O)c3nc(C#N)c[nH]3)c(C3=CCC(C)(C)CC3)c2)CCOCC1] | Example 4 | |
| 38 | 4-Cyano-1H-imidazole-2-carboxylic acid {4-[4-(2-acetylamino-ethylamino)-tetrahydro-pyran-4-yl]-2-cyclohex-1-enyl-phenyl}-amide | 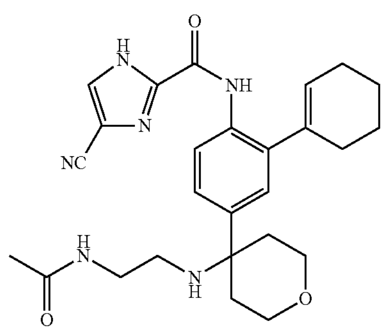 [SMILES: CC(=O)NCCNC1(c2ccc(NC(=O)c3nc(C#N)c[nH]3)c(C3=CCCCC3)c2)CCOCC1] | Example 4 | |
| 39 | 4-Cyano-1H-pyrrole-2-carboxylic acid {2-(4,4-dimethyl-cyclohex-1-enyl)-4-[4-(2-methoxy-ethylamino)-tetrahydro-pyran-4-yl]-phenyl}-amide | 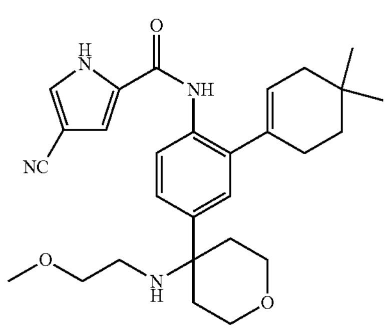 | Example 1, steps (f), (h); Example 4 | (*Canadian J. Chem.* 59, 2673 (1981)); |

| Example No. | Name | Structure | Procedure Reference | Reagents |
|---|---|---|---|---|
| 40 | 4-Cyano-1H-imidazole-2-carboxylic acid [4-[4-(4-acetyl-piperazin-1-yl)-tetrahydro-pyran-4-yl]-2-(4,4-dimethyl-cyclohex-1-enyl)-phenyl]-amide | 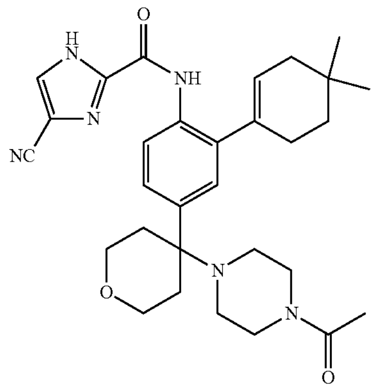 [SMILES: CC(=O)N1CCN(C2(c3ccc(NC(=O)c4nc(C#N)c[nH]4)c(C4=CCC(C)(C)CC4)c3)CCOCC2)CC1] | Example 4 | (acetylpiperazine) |
| 41 | 4-Cyano-1H-imidazole-2-carboxylic acid [4-(4-amino-1,1-dioxo-hexahydro-1$\lambda^6$-thiopyran-4-yl)-2-(4,4-dimethyl-cyclohex-1-enyl)-phenyl]-amide | 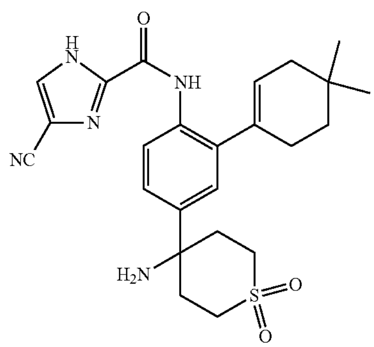 [SMILES: CC1(C)CC=C(c2cc(C3(N)CCS(=O)(=O)CC3)ccc2NC(=O)c2nc(C#N)c[nH]2)CC1] | Example 12; Example 4 | $NH_4OH$ |
| 42 | 4-Cyano-1H-imidazole-2-carboxylic acid [4-(4-dimethylamino-1,1-dioxo-hexahydro-1$\lambda^6$-thiopyran-4-yl)-2-(4,4-dimethyl-cyclohex-1-enyl)-phenyl]-amide | 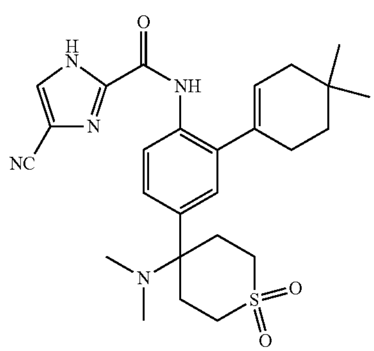 [SMILES: CN(C)C1(c2ccc(NC(=O)c3nc(C#N)c[nH]3)c(C3=CCC(C)(C)CC3)c2)CCS(=O)(=O)CC1] | Example 12; Example 4 | $HNMe_2$ |
| 43 | 4-Cyano-1H-imidazole-2-carboxylic acid [4-(1-acetyl-4-dimethylamino-piperidin-4-yl)-2-(4,4-dimethyl-cyclohex-1-enyl)-phenyl]-amide | 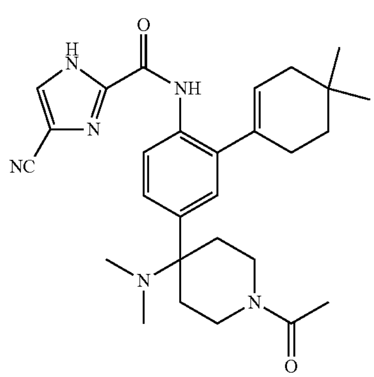 [SMILES: CC(=O)N1CCC(c2ccc(NC(=O)c3nc(C#N)c[nH]3)c(C3=CCC(C)(C)CC3)c2)(N(C)C)CC1] | Example 35; Example 4 | $HNMe_2$ |

-continued

| Example No. | Name | Structure | Procedure Reference | Reagents |
|---|---|---|---|---|
| 44 | 4-Cyano-1H-imidazole-2-carboxylic acid {2-(4,4-dimethyl-cyclohex-1-enyl)-4-[4-(2-pyrrolidin-1-yl-ethoxy)-tetrahydro-pyran-4-yl]-phenyl}-amide | 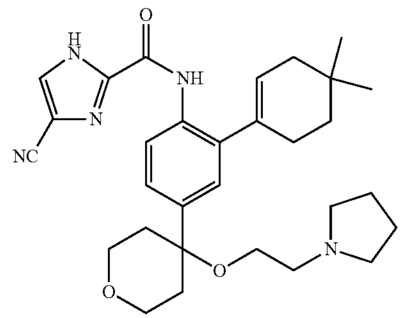 [SMILES: CC1(C)CC=C(c2cc(C3(OCCN4CCCC4)CCOCC3)ccc2NC(=O)c2nc(C#N)c[nH]2)CC1] | Example 2 | |
| 45 | 4-Cyano-1H-pyrrole-2-carboxylic acid {2-(4,4-dimethyl-cyclohex-1-enyl)-4-[4-(2-pyrrolidin-1-yl-ethoxy)-tetrahydro-pyran-4-yl]-phenyl}-amide | 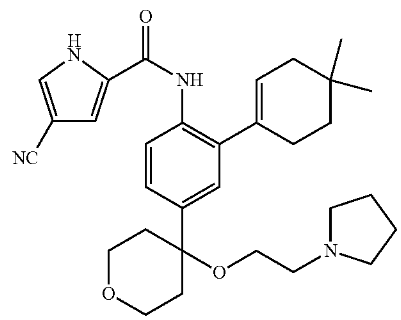 [SMILES: CC1(C)CC=C(c2cc(C3(OCCN4CCCC4)CCOCC3)ccc2NC(=O)c2cc(C#N)c[nH]2)CC1] | Example 1, steps (f), (h); Example 2 | (*Canadian J. Chem.* 59, 2673 (1981)); |
| 46 | 4-Cyano-1H-pyrrole-2-carboxylic acid [4-[4-(2-dimethylamino-ethoxy)-tetrahydro-pyran-4-yl]-2-(4,4-dimethyl-cyclohex-1-enyl)-phenyl]-amide | 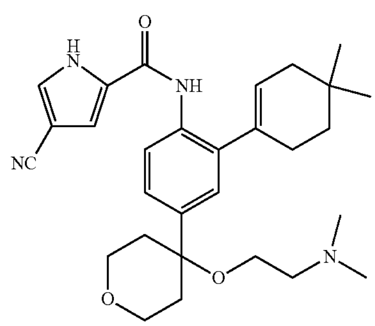 [SMILES: CN(C)CCOC1(c2ccc(NC(=O)c3cc(C#N)c[nH]3)c(C3=CCC(C)(C)CC3)c2)CCOCC1] | Example 1, steps (f), (h); Example 2 | (*Canadian J. Chem.* 59, 2673 (1981)); |
| 47 | 4-Cyano-1H-imidazole-2-carboxylic acid {2-(4-methyl-piperidin-1-yl)-4-[4-(2-pyrrolidin-1-yl-ethylamino)-tetrahydro-pyran-4-yl]-phenyl}-amide | 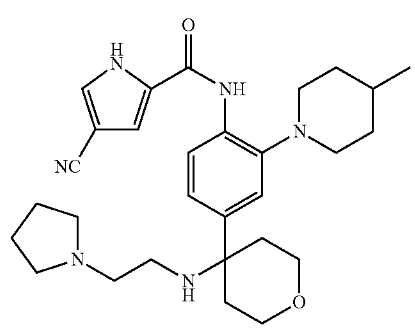 [SMILES: CC1CCN(c2cc(C3(NCCN4CCCC4)CCOCC3)ccc2NC(=O)c2cc(C#N)c[nH]2)CC1] | Example 1, steps (f)-(h); Example 4 | (US 2005131022 A1); |

-continued

| Example No. | Name | Structure | Procedure Reference | Reagents |
|---|---|---|---|---|
| 48 | 4-Cyano-1H-imidazole-2-carboxylic acid [4-[4-(2-dimethylamino-ethylamino)-tetrahydro-pyran-4-yl]-2-(4-methyl-piperidin-1-yl)-phenyl]-amide | 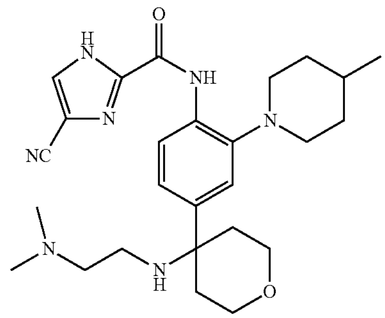 | Example 1, steps (f)-(h); Example 4 | (US 2005131022 A1); |
| 49 | 4-Cyano-1H-imidazole-2-carboxylic acid [4-[4-(2-dimethylamino-ethoxy)-tetrahydro-pyran-4-yl]-2-(4-methyl-piperidin-1-yl)-phenyl]-amide | 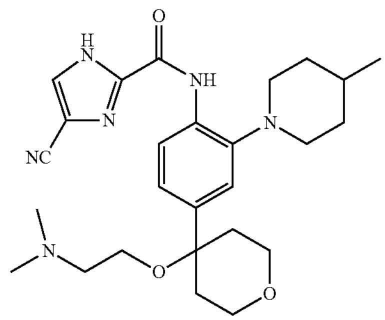 | Example 1, steps (f)-(h); Example 2 | (US 2005131022 A1); |
| 50 | 4-Cyano-1H-imidazole-2-carboxylic acid {2-(4-methyl-piperidin-1-yl)-4-[4-(2-pyrrolidin-1-yl-ethoxy)-tetrahydro-pyran-4-yl]-phenyl}-amide | 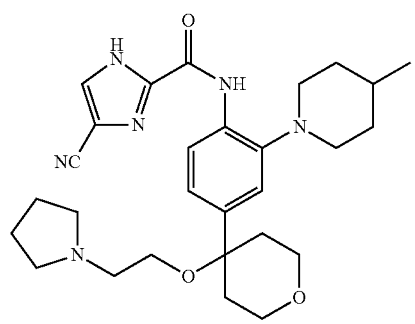 [SMILES: CC1CCN(c2cc(C3(OCCN4CCCC4)CCOCC3)ccc2NC(=O)c2nc(C#N)c[nH]2)CC1] | Example 1, steps (f)-(h); Example 2 | (US 2005131022 A1); |
| 51 | 4-Cyano-1H-imidazole-2-carboxylic acid [4-(4-amino-tetrahydro-pyran-4-yl)-2-(4-methyl-piperidin-1-yl)-phenyl]-amide | 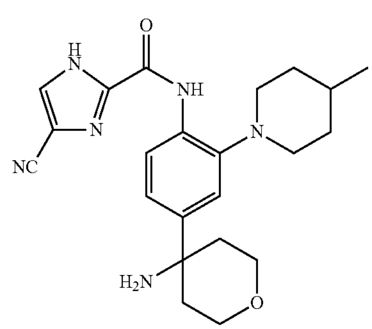 [SMILES: CC1CCN(c2cc(C3(N)CCOCC3)ccc2NC(=O)c2nc(C#N)c[nH]2)CC1] | Example 1, Steps (f)-(h); Example 4 | (US 2005131022 A1); NH$_4$OH |

| Example No. | Name | Structure | Procedure Reference | Reagents |
|---|---|---|---|---|
| 52 | 4-Cyano-1H-imidazole-2-carboxylic acid [4-(4-dimethylamino-tetrahydro-pyran-4-yl)-2-(4-methyl-piperidin-1-yl)-phenyl]-amide | 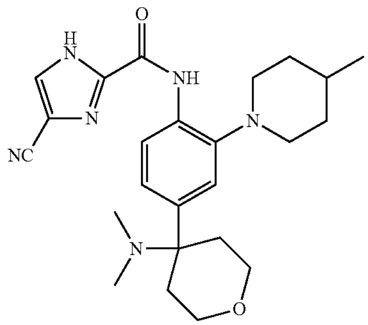 [SMILES: CC1CCN(c2cc(C3(N(C)C)CCOCC3)ccc2NC(=O)c2nc(C#N)c[nH]2)CC1] | Example 1, Steps (f)-(h); Example 4 | (US 2005131022 A1); HNMe$_2$ |
| 53 | 4-Cyano-1H-imidazole-2-carboxylic acid [2-(4-methyl-piperidin-1-yl)-4-(4-pyrrolidin-1-yl-tetrahydro-pyran-4-yl)-phenyl]-amide | 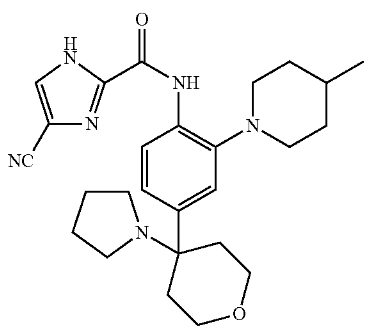 [SMILES: CC1CCN(c2cc(C3(N4CCCC4)CCOCC3)ccc2NC(=O)c2nc(C#N)c[nH]2)CC1] | Example 1, Steps (f)-(h); Example 4 | (US 2005131022 A1); |
| 54 | 4-Cyano-1H-imidazole-2-carboxylic acid [4-(1,1-dioxo-4-pyrrolidin-1-yl-hexahydro-1λ$^6$-thiopyran-4-yl)-2-(4-methyl-piperidin-1-yl)-phenyl]-amide | 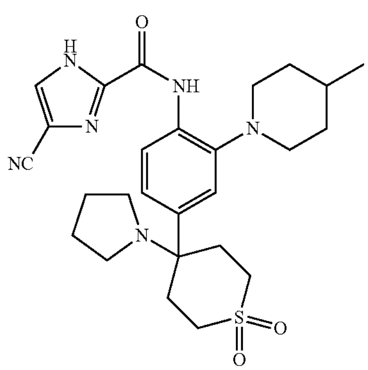 [SMILES: CC1CCN(c2cc(C3(N4CCCC4)CCS(=O)(=O)CC3)ccc2NC(=O)c2nc(C#N)c[nH]2)CC1] | Example 1, Steps (f)-(h); Example 12 Example 4 | (US 2005131022 A1); MCPBA; |

-continued

| Example No. | Name | Structure | Procedure Reference | Reagents |
|---|---|---|---|---|
| 55 | 4-Cyano-1H-imidazole-2-carboxylic acid [4-(1-acetyl-4-pyrrolidin-1-yl-piperidin-4-yl)-2-(4-methyl-piperidin-1-yl)-phenyl]-amide | 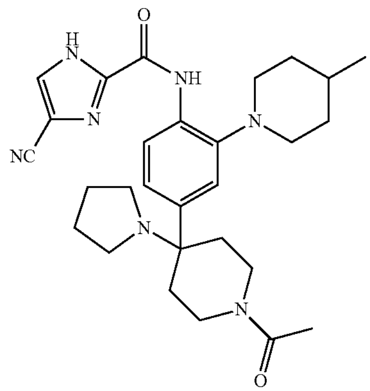 [SMILES: CC(=O)N1CCC(c2ccc(NC(=O)c3nc(C#N)c[nH]3)c(N3CCC(C)CC3)c2)(N2CCCC2)CC1] | Example 1, Steps (f)-(h); Example 4 | (US 2005131022 A1); |
| 56 | 4-Cyano-1H-imidazole-2-carboxylic acid [2-(4,4-dimethyl-cyclohex-1-enyl)-4-(4-pyrrolidin-1-ylmethyl-tetrahydro-pyran-4-yl)-phenyl]-amide | 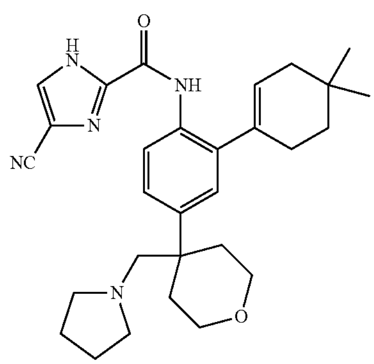 [SMILES: CC1(C)CC=C(c2cc(C3(CN4CCCC4)CCOCC3)ccc2NC(=O)c2nc(C#N)c[nH]2)CC1] | Example 26, step (b) | |
| 57 | 4-Cyano-1H-imidazole-2-carboxylic acid [4-(4-dimethylaminomethyl-tetrahydro-pyran-4-yl)-2-(4,4-dimethyl-cyclohex-1-enyl)-phenyl]-amide | 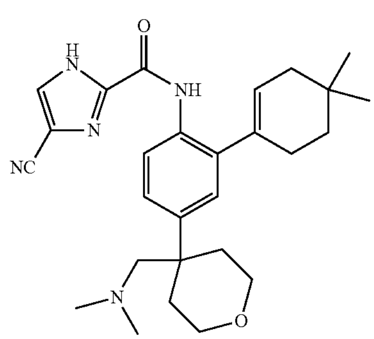 [SMILES: CN(C)CC1(c2ccc(NC(=O)c3nc(C#N)c[nH]3)c(C3=CCC(C)(C)CC3)c2)CCOCC1] | Example 26, step (b) | $HNMe_2$ |

| Example No. | Name | Structure | Procedure Reference | Reagents |
|---|---|---|---|---|
| 58 | 4-Cyano-1H-imidazole-2-carboxylic acid [4-(4-dimethylaminomethyl-1,1-dioxo-hexahydro-1λ6-thiopyran-4-yl)-2-(4,4-dimethyl-cyclohex-1-enyl)-phenyl]-amide | 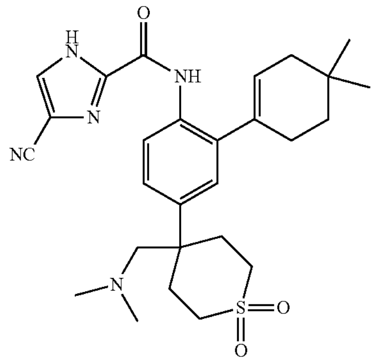 [SMILES: CN(C)CC1(c2ccc(NC(=O)c3nc(C#N)c[nH]3)c(C3=CCC(C)(C)CC3)c2)CCS(=O)(=O)CC1] | Example 16; step (a); Example 12; Example 16, Steps (b)-(f); Example 25; Example 26, steps (a)-(b) | (Phosphorus, Sulfur and Silicon and the Related Elements, 47(1-2), 157-64 (1990)); MCPBA; HNMe$_2$ |
| 59 | 4-Cyano-1H-imidazole-2-carboxylic acid [2-(4,4-dimethyl-cyclohex-1-enyl)-4-(4-hydroxy-2,6-dimethyl-tetrahydro-thiopyran-4-yl)-phenyl]-amide | 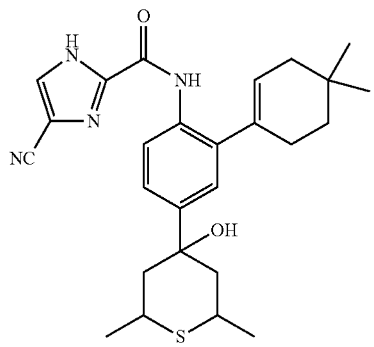 [SMILES: CC1CC(O)(c2ccc(NC(=O)c3nc(C#N)c[nH]3)c(C3=CCC(C)(C)CC3)c2)CC(C)S1] | Ex. 1, step (h) | Khimiya Geterotsikliches kikh Soedinenii, Sbornik, No. 2 (Kislorodsoderz hashchie Geterotsikly), 174-80, (1970) |
| 60 | 4-Cyano-1H-imidazole-2-carboxylic acid [2-(4,4-dimethyl-cyclohex-1-enyl)-4-(4-hydroxy-2,6-dimethyl-1,1-dioxo-hexahydro-1λ6-thiopyran-4-yl)-phenyl]-amide | 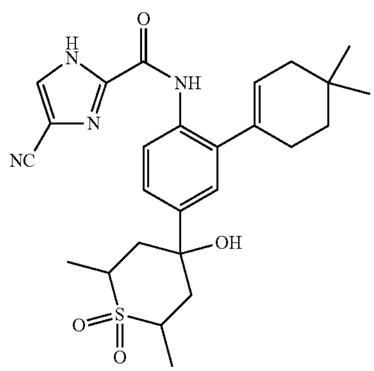 [SMILES: CC1CC(O)(c2ccc(NC(=O)c3nc(C#N)c[nH]3)c(C3=CCC(C)(C)CC3)c2)CC(C)S1(=O)=O] | Ex. 1, step (h) | Journal of the American Chemical Society, 97(13), 3666-72, (1975) |
| 61 | 4-Cyano-1H-imidazole-2-carboxylic acid [2-(4,4-dimethyl-cyclohex-1-enyl)-4-(3-hydroxy-8,8-dioxo-8 λ6-thia-bicyclo[3.2.1]oct-3-yl)-phenyl]-amide | 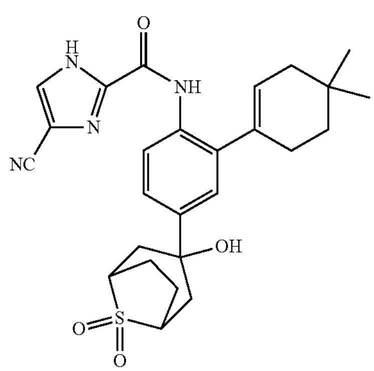 [SMILES: CC1(C)CC=C(c2cc(C3(O)CC4CCC(C3)S4(=O)=O)ccc2NC(=O)c2nc(C#N)c[nH]2)CC1] | Ex. 1, step (h) | Heterocycles 13 (Spec. Issue), 293-6, (1979) |

-continued

| Example No. | Name | Structure | Procedure Reference | Reagents |
|---|---|---|---|---|
| 62 | 4-Cyano-1H-imidazole-2-carboxylic acid [2-(4,4-dimethyl-cyclohex-1-enyl)-4-(3-hydroxy-8-methyl-8-aza-bicyclo[3.2.1]oct-3-yl)-phenyl]-amide | 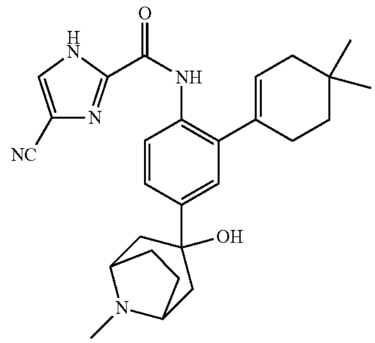 [SMILES: CN1C2CCC1CC(O)(c1ccc(NC(=O)c3nc(C#N)c[nH]3)c(C3=CCC(C)(C)CC3)c1)C2] | Ex. 1, step (h) | |
| 63 | 4-Cyano-1H-imidazole-2-carboxylic acid [2-(4,4-dimethyl-cyclohex-1-enyl)-4-(4-hydroxy-1,2,6-trimethyl-piperidin-4-yl)-phenyl]-amide | 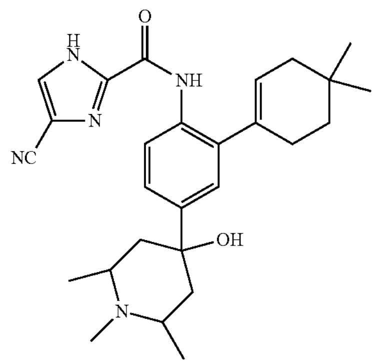 [SMILES: CC1CC(O)(c2ccc(NC(=O)c3nc(C#N)c[nH]3)c(C3=CCC(C)(C)CC3)c2)CC(C)N1C] | Ex. 1, step (h) | *Journal of Organic Chemistry*, 15 337-42, (1950) |
| 64 | 4-Cyano-1H-imidazole-2-carboxylic acid [2-(4,4-dimethyl-cyclohex-1-enyl)-4-(4-hydroxy-1,2,2,6,6-pentamethyl-piperidin-4-yl)-phenyl]-amide | 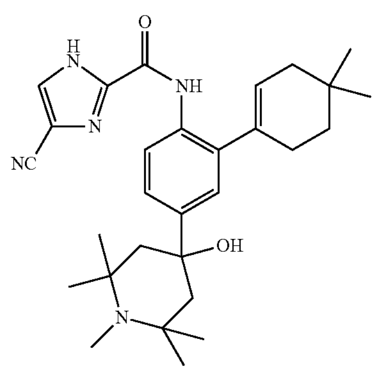 [SMILES: CN1C(C)(C)CC(O)(c2ccc(NC(=O)c3nc(C#N)c[nH]3)c(C3=CCC(C)(C)CC3)c2)CC1(C)C] | Ex. 1, step (h) | EP 729947 |
| 65 | 4-Cyano-1H-imidazole-2-carboxylic acid {2-(4,4-dimethyl-cyclohex-1-enyl)-4-[4-(2-methoxy-ethylamino)-2,6-dimethyl-1,1-dioxo-hexahydro-1λ⁶-thiopyran-4-yl]-phenyl}-amide | 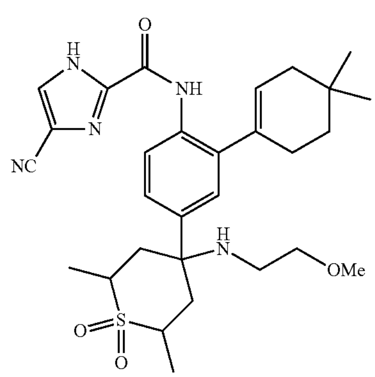 [SMILES: COCCNC1(c2ccc(NC(=O)c3nc(C#N)c[nH]3)c(C3=CCC(C)(C)CC3)c2)CC(C)S(=O)(=O)C(C)C1] | Ex. 1, step (h) | *Journal of the American Chemical Society*, 97(13), 3666-72. (1975). 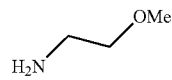 |

-continued

| Example No. | Name | Structure | Procedure Reference | Reagents |
|---|---|---|---|---|
| 66 | 4-Cyano-1H-imidazole-2-carboxylic acid {2-(4,4-dimethyl-cyclohex-1-enyl)-4-[1,2,2,6,6-pentamethyl-4-(2-morpholin-4-yl-ethylamino)-piperidin-4-yl]-phenyl}-amide | 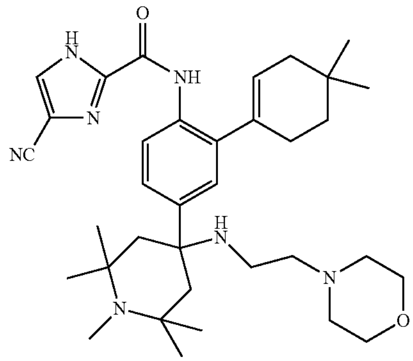 [SMILES: CN1C(C)(C)CC(NCCN2CCOCC2)(c2ccc(NC(=O)c3nc(C#N)c[nH]3)c(C3=CCC(C)(C)CC3)c2)CC1(C)C] | Ex. 1, step (h) | EP 729947 |
| 67 | 3-{4-[4-[(4-Cyano-1H-imidazole-2-carbonyl)-amino]-3-(4,4-dimethyl-cyclohex-1-enyl)-phenyl]-1,2,6-trimethyl-piperidin-4-ylamino}-propionic acid methyl ester | 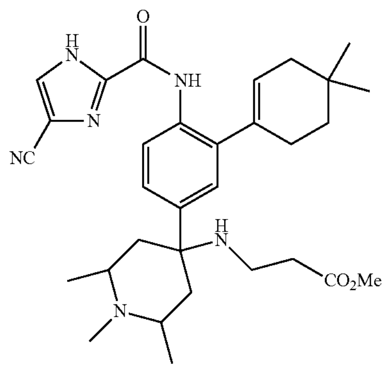 [SMILES: COC(=O)CCNC1(c2ccc(NC(=O)c3nc(C#N)c[nH]3)c(C3=CCC(C)(C)CC3)c2)CC(C)N(C)C(C)C1] | Ex. 1, step (h) | *Journal of Organic Chemistry*, 15 337-42, (1950) |
| 68 | 4-Cyano-1H-imidazole-2-carboxylic acid (2-(4,4-dimethyl-cyclohex-1-enyl)-4-{2,6-dimethyl-4-[2-(4-methyl-piperazin-1-yl)-ethylamino]-1,1-dioxo-hexahydro-1λ⁶-thiopyran-4-yl}-phenyl)-amide | 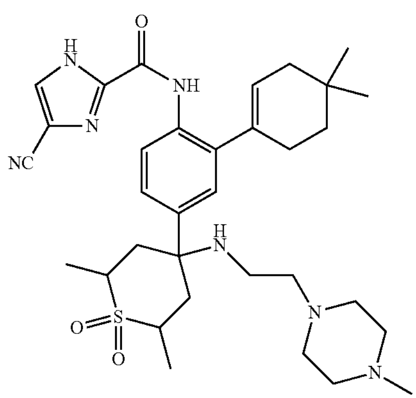 [SMILES: CC1CC(NCCN2CCN(C)CC2)(c2ccc(NC(=O)c3nc(C#N)c[nH]3)c(C3=CCC(C)(C)CC3)c2)CC(C)S1(=O)=O] | Ex. 1, step (h) | *Journal of the American Chemical Society*, 97(13), 3666-72. (1975). |
| 69 | 4-Cyano-1H-imidazole-2-carboxylic acid [2-cyclohex-1-enyl-4-(4-hydroxy-1,2,6-trimethyl-piperidin-4-yl)-phenyl]-amide | 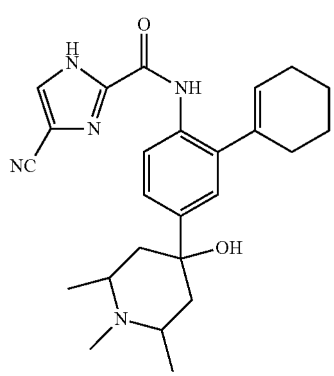 [SMILES: CC1CC(O)(c2ccc(NC(=O)c3nc(C#N)c[nH]3)c(C3=CCCCC3)c2)CC(C)N1C] | Ex. 14, step (d) | *Journal of Organic Chemistry*, 15 337-42, (1950) |

-continued

| Example No. | Name | Structure | Procedure Reference | Reagents |
|---|---|---|---|---|
| 70 | 4-Cyano-1H-imidazole-2-carboxylic acid {2-cyclohex-1-enyl-4-[1,2,6-trimethyl-4-(2-morpholin-4-yl-ethoxy)-piperidin-4-yl]-phenyl}-amide | 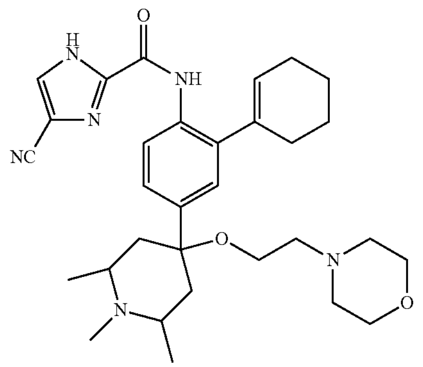 [SMILES: CC1CC(OCCN2CCOCC2)(c2ccc(NC(=O)c3nc(C#N)c[nH]3)c(C3=CCCCC3)c2)CC(C)N1C] | Ex. 14, step (d) Ex. 2 | *Journal of Organic Chemistry*, 15 337-42, (1950) |
| 71 | 4-Cyano-1H-imidazole-2-carboxylic acid {2-cyclohex-1-enyl-4-[1,2,6-trimethyl-4-(2-pyrrolidin-1-yl-ethoxy)-piperidin-4-yl]-phenyl}-amide | 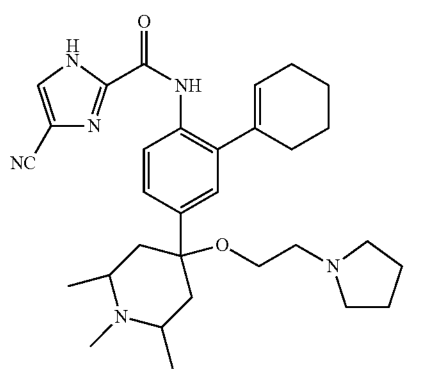 [SMILES: CC1CC(OCCN2CCCC2)(c2ccc(NC(=O)c3nc(C#N)c[nH]3)c(C3=CCCCC3)c2)CC(C)N1C] | Ex. 14, step (d) Ex. 2 | *Journal of Organic Chemistry*, 15 337-42, (1950) |
| 72 | 4-Cyano-1H-imidazole-2-carboxylic acid (2-cyclohex-1-enyl-4-{4-[2-(1,1-dioxo-1$\lambda^6$-thiomorpholin-4-yl)-ethoxy]-1,2,6-trimethyl-piperidin-4-yl}-phenyl)-amide | 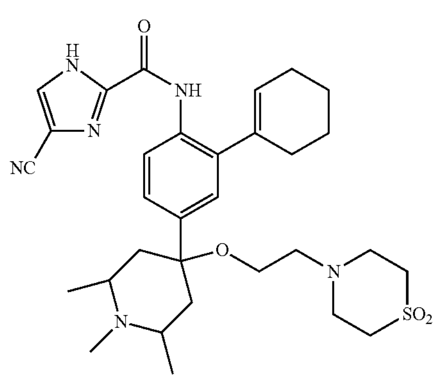 [SMILES: CC1CC(OCCN2CCS(=O)(=O)CC2)(c2ccc(NC(=O)c3nc(C#N)c[nH]3)c(C3=CCCCC3)c2)CC(C)N1C] | Ex. 14, step (d) Ex. 2 | *Journal of Organic Chemistry*, 15 337-42, (1950)<br><br>(ChemPacific) |

Example 73

4-Cyano-1H-imidazole-2-carboxylic acid [4-(4-aminomethyl-tetrahydro-pyran-4-yl)-2-(4,4-dimethyl-cyclohex-1-enyl)-phenyl]-amide

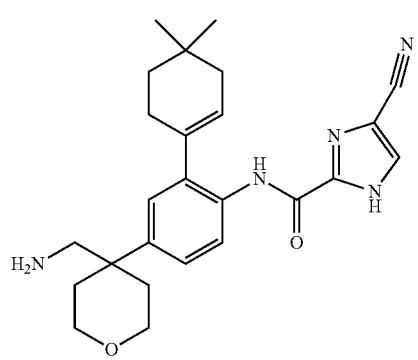 [SMILES: CC1(C)CC=C(c2cc(C3(CN)CCOCC3)ccc2NC(=O)c2nc(C#N)c[nH]2)CC1]

a) 4-(4-Nitro-phenyl)-tetrahydro-pyran-4-carbonitrile

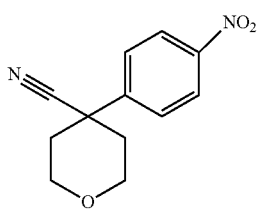 [SMILES: N#CC1(c2ccc([N+](=O)[O-])cc2)CCOCC1]

A slurry of NaH (95%, dry, 2.4 eq) in DMSO is treated with 4-(nitro-phenyl)-acetonitrile (1 eq) portionwise and stirred at RT until $H_2$ evolution ceases. The mixture is treated with 1-bromo-2-(2-bromo-ethoxy)-ethane (1.2 eq) and stirred at 70° C. for 3 h. The solution is diluted with EtOAc and washed with water. The organic layer is dried ($MgSO_4$) and concentrated in vacuo. The residue is purified by silica gel chromatography with an appropriate solvent to afford the title compound.

b) C-[4-(4-Nitro-phenyl)-tetrahydro-pyran-4-yl]-methylamine

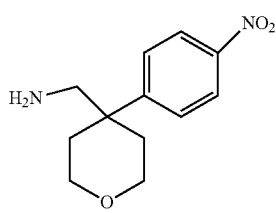 [SMILES: NCC1(c2ccc([N+](=O)[O-])cc2)CCOCC1]

A solution of 4-(4-nitro-phenyl)-tetrahydro-pyran-4-carbonitrile (as prepared in the previous step) in THF is treated with $ZrCl_4$ and $NaBH_4$ (*Synthesis*, (12), 995-6 (1988)) at RT. The mixture is diluted with EtOAc and washed with water. The organic layer is dried ($MgSO_4$) and concentrated in vacuo. The residue is purified by silica gel chromatography with the appropriate solvent to afford the title compound.

c) [4-(4-Nitro-phenyl)-tetrahydro-pyran-4-ylmethyl]-carbamic acid tert-butyl ester

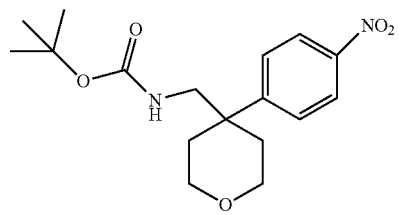 [SMILES: CC(C)(C)OC(=O)NCC1(c2ccc([N+](=O)[O-])cc2)CCOCC1]

A solution of C-[4-(4-nitro-phenyl)-tetrahydro-pyran-4-yl]-methylamine (as prepared in the previous step) in THF is treated with $BOC_2O$ at RT. The mixture is diluted with EtOAc and washed with water. The organic layer is dried ($MgSO_4$) and concentrated in vacuo. The residue is purified by silica gel chromatography with the appropriate solvent to afford the title compound.

d) 4-Cyano-1H-imidazole-2-carboxylic acid [4-(4-aminomethyl-tetrahydro-pyran-4-yl)-2-(4,4-dimethyl-cyclohex-1-enyl)-phenyl]-amide The title compound is prepared from [4-(4-nitro-phenyl)-tetrahydro-pyran-4-ylmethyl]-carbamic acid tert-butyl ester (as prepared in the previous step) according the procedure in Example 22 step (c) and Example 1, steps (e)-(g).

Example 74

4-Cyano-1H-imidazole-2-carboxylic acid [4-(4-carbamoyl-1,1-dioxo-hexahydro-1$\lambda^6$thiopyran-4-yl)-2-(4,4-dimethyl-cyclohex-1-enyl)-phenyl]-amide

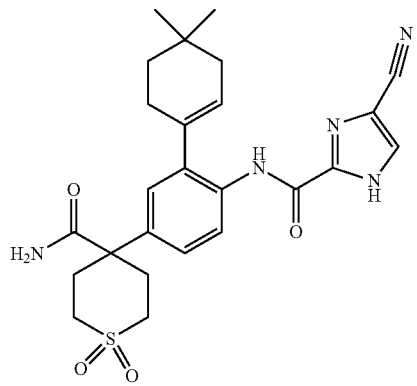 [SMILES: CC1(C)CC=C(c2cc(C3(C(N)=O)CCS(=O)(=O)CC3)ccc2NC(=O)c2nc(C#N)c[nH]2)CC1]

a) 4-(4-Nitro-phenyl)-1,1-dioxo-hexahydro-1$\lambda^6$-thiopyran-4-carbonitrile

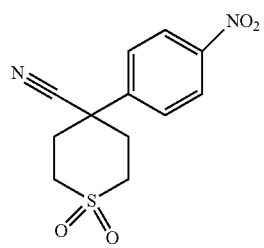 [SMILES: N#CC1(c2ccc([N+](=O)[O-])cc2)CCS(=O)(=O)CC1]

The title compound is prepared from 4-(nitro-phenyl)-acetonitrile and 1-bromo-2-(2-bromo-ethanesulfonyl)-ethane according to the procedure in Example 73, step (a).

b) 4-(4-Nitro-phenyl)-1,1-dioxo-hexahydro-1λ⁶-thiopyran-4-carboxylic acid amide

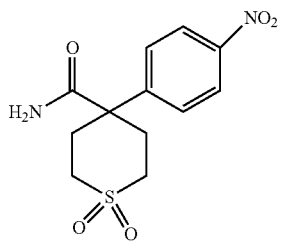 [SMILES: NC(=O)C1(c2ccc([N+](=O)[O-])cc2)CCS(=O)(=O)CC1]

A solution of 4-(4-nitro-phenyl)-1,1-dioxo-1λ⁶-thiopyran-4-carbonitrile (as prepared in the previous step) in ethanol and water is treated with NaBO₃ (*Synthetic Communications*, 20(4), 563-71, (1990)). The mixture is diluted with EtOAc and washed with water. The organic layer is dried (MgSO₄) and concentrated in vacuo. The residue is purified by silica gel chromatography with the appropriate solvent to afford the title compound.

c) 4-Cyano-1H-imidazole-2-carboxylic acid [4-(4-carbamoyl-1,1-dioxo-hexahydro-1λ⁶thiopyran-4-yl)-2-(4,4-dimethyl-cyclohex-1-enyl)-phenyl]-amide The title compound was prepared from 4-(4-nitro-phenyl)-1,1-dioxo-hexahydro-1λ⁶-thiopyran-4-carboxylic acid amide (as prepared in the previous step) according to the procedure of Example 22, step (c) and Example 1, steps (e)-(g).

Example 75

4-Cyano-1H-imidazole-2-carboxylic acid (2-(4,4-dimethyl-cyclohex-1-enyl)-4-{4-[(2-methoxy-ethylamino)-methyl]-tetrahydro-pyran-4-yl}-phenyl)-amide

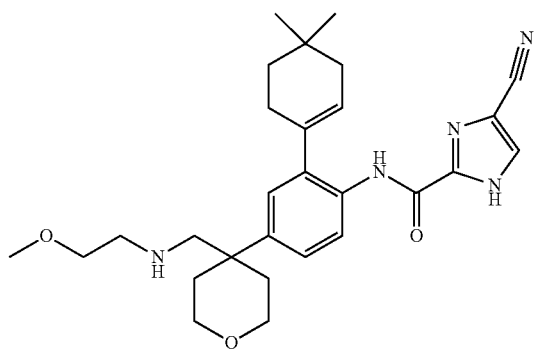 [SMILES: COCCNCC1(c2ccc(NC(=O)c3nc(C#N)c[nH]3)c(C3=CCC(C)(C)CC3)c2)CCOCC1]

a) (2-Methoxy-ethyl)-[4-(4-nitro-phenyl)-tetrahydro-pyran-4-ylmethyl]-amine

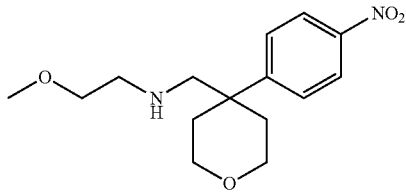 [SMILES: COCCNCC1(c2ccc([N+](=O)[O-])cc2)CCOCC1]

A solution of C-[4-(4-nitro-phenyl)-tetrahydro-pyran-4-yl]-methylamine (as prepared in Example 73, step (b)) in THF is treated with 1-bromo-2-methoxy-ethane and TEA. The mixture is diluted with EtOAc and washed with water. The organic layer is dried (MgSO₄) and concentrated in vacuo. The residue is purified by silica gel chromatography with the appropriate solvent to afford the title compound.

b) 4-Cyano-1H-imidazole-2-carboxylic acid (2-(4,4-dimethyl-cyclohex-1-enyl)-4-{4-[(2-methoxy-ethylamino)-methyl]-tetrahydro-pyran-4-yl}-phenyl)-amide The title compound is prepared from (2-methoxy-ethyl)-[4-(4-nitro-phenyl)-tetrahydro-pyran-4-ylmethyl]-amine (as prepared in the previous step) according to the procedure in Example 22 step (c) and Example 1, steps (e)-(g).

Example 76

4-Cyano-1H-imidazole-2-carboxylic acid [2-(4,4-dimethyl-cyclohex-1-enyl)-4-(4-methylaminomethyl-tetrahydro-pyran-4-yl)-phenyl]-amide

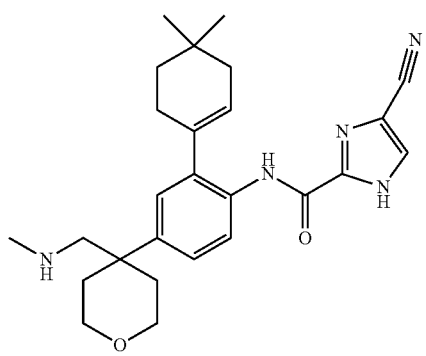 [SMILES: CNCC1(c2ccc(NC(=O)c3nc(C#N)c[nH]3)c(C3=CCC(C)(C)CC3)c2)CCOCC1]

a) Methyl-[4-(4-nitro-phenyl)-tetrahydro-pyran-4-ylmethyl]-amine

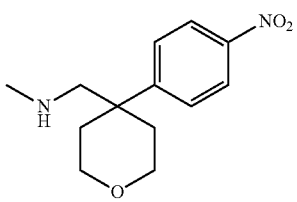 [SMILES: CNCC1(c2ccc([N+](=O)[O-])cc2)CCOCC1]

A solution of C-[4-(4-nitro-phenyl)-tetrahydro-pyran-4-yl]-methylamine (as prepared in Example 73, step (b)) in DCM is treated with formaldehyde according to the literature procedure found in *J. Org. Chem.*, 61, 3849-3862, (1996). The mixture is diluted with EtOAc and washed with water. The organic layer is dried (MgSO$_4$) and concentrated in vacuo. The residue is purified by silica gel chromatography with the appropriate solvent to afford the title compound.

b) 4-Cyano-1H-imidazole-2-carboxylic acid [2-(4,4-dimethyl-cyclohex-1-enyl)-4-(4-methylaminom-ethyl-tetrahydro-pyran-4-yl)-phenyl]-amide The title compound is prepared from methyl-[4-(4-nitro-phenyl)-tetrahydro-pyran-4-yl-methyl]-amine (as prepared in the previous step) according to the procedures in Example 22 step (c) and Example 1, steps (e)-(g).

Example 77

4-Cyano-1H-imidazole-2-carboxylic acid [4-(1-acetyl-4-methylaminomethyl-piperidin-4-yl)-2-(4,4-dimethyl-cyclohex-1-enyl)-phenyl]-amide

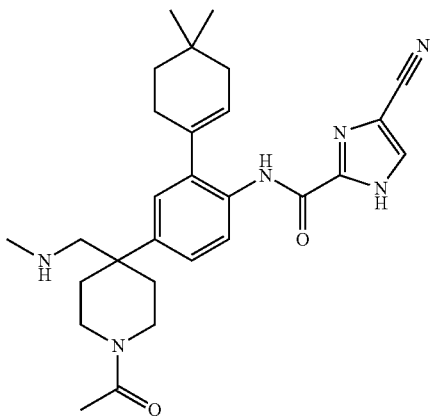 [SMILES: CNCC1(c2ccc(NC(=O)c3nc(C#N)c[nH]3)c(C3=CCC(C)(C)CC3)c2)CCN(C(C)=O)CC1]

a) 4-(4-Nitro-phenyl)-piperidine-4-carbonitrile

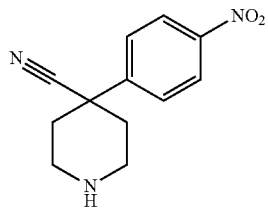 [SMILES: N#CC1(c2ccc([N+](=O)[O-])cc2)CCNCC1]

The title compound is prepared from 4-(nitro-phenyl)-acetonitrile and mechlorethamine hydrochloride according to the procedure in Example 73, step (a).

b) 1-Acetyl-4-(4-nitro-phenyl)-piperidine-4-carbonitrile

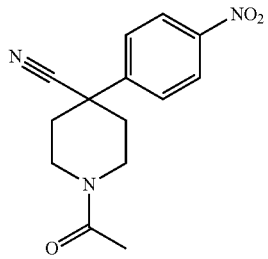 [SMILES: CC(=O)N1CCC(C#N)(c2ccc([N+](=O)[O-])cc2)CC1]

A solution of 4-(4-nitro-phenyl)-piperidine-4-carbonitrile (as prepared in the previous step) in CH$_2$Cl$_2$ is treated with CH$_3$COCl and DIEA. The mixture is washed with water, and the organic layer is dried (MgSO$_4$) and concentrated in vacuo. The residue is purified by silica gel chromatography with the appropriate solvent to afford the title compound.

c) 1-Acetyl-4-(4-nitro-phenyl)-piperidine-4-carboxylic acid

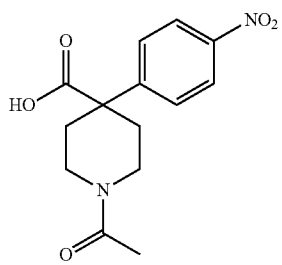 [SMILES: CC(=O)N1CCC(C(=O)O)(c2ccc([N+](=O)[O-])cc2)CC1]

A solution of 1-acetyl-4-(4-nitro-phenyl)-piperidine-4-carbonitrile (as prepared in the previous step) in EtOH and aqueous NaOH is heated to reflux. The mixture is treated with aqueous HCl and extracted with EtOAc. The organic layer is dried over MgSO$_4$ and concentrated in vacuo. The residue is purified by reverse phase chromatography to afford the title compound.

d) 4-Cyano-1H-imidazole-2-carboxylic acid [4-(1-acetyl-4-methylaminomethyl-piperidin-4-yl)-2-(4,4-dimethyl-cyclohex-1-enyl)-phenyl]-amide The title compound is prepared from 1-acetyl-4-(4-nitro-phenyl)-piperidine-4-carboxylic acid (as prepared in the previous step) according to the procedures in Example 20, Example 21 steps (a)-(b), Example 22 steps (c)-(d), and Example 1 steps (e)-(g).

Example 78

4-Cyano-4-[4-[(4-cyano-1H-imidazole-2-carbonyl)-amino]-3-(4,4-dimethyl-cyclohex-1-enyl)-phenyl]-piperidine-1-carboxylic acid amide

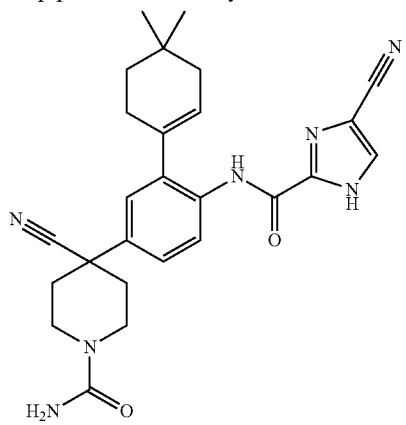

115 a) 4-Cyano-4-(4-nitro-phenyl)-piperidine-1-carboxylic acid amide

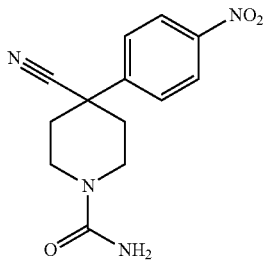 [SMILES: N#CC1(c2ccc([N+](=O)[O-])cc2)CCN(C(N)=O)CC1]

116

The title compound is prepared from 4-(4-nitro-phenyl)-piperidine-4-carbonitrile (as prepared in Example 77, step (a)) using 4-nitro-phenyl chloroformate and ammonia in 1,4-dioxane according to the procedure in *QSAR & Combinatorial Science*, 23(10), 854-858 (2004).

b) 4-Cyano-4-[4-[(4-cyano-1H-imidazole-2-carbonyl)-amino]-3-(4,4-dimethyl-cyclohex-1-enyl)-phenyl]-piperidine-1-carboxylic acid amide The title compound is prepared from 4-cyano-4-(4-nitro-phenyl)-piperidine-1-carboxylic acid amide (as prepared in the previous step) according to the procedures in Example 22 step (c) and Example 1, steps (e)-(g).

The following examples are produced according to procedures of previous examples with the corresponding reagents as indicated in the table below:

| Example No. | Name | Structure | Procedure Reference | Reagents |
|---|---|---|---|---|
| 79 | 4-Cyano-1H-imidazole-2-carboxylic acid [4-[(4-acetylamino-methyl)-tetrahydro-pyran-4-yl]-2-(4,4-diethylcyclohex-1-enyl)-phenyl]-amide | 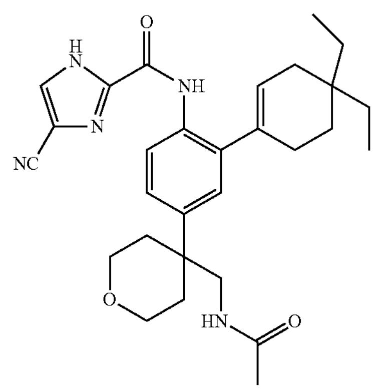 [SMILES: CCC1(CC)CC=C(c2cc(C3(CNC(C)=O)CCOCC3)ccc2NC(=O)c2nc(C#N)c[nH]2)CC1] | Ex. 73, steps (a)-(c); Ex. 22, step (c) and Ex. 1, steps (e)-(g) | (WO 2005063705) |
| 80 | 4-Cyano-1H-pyrrole-2-carboxylic acid [4-(1-acetyl-4-methylaminomethyl-piperidin-4-yl)-2-(4,4-diethyl-cyclohex-1-enyl)-phenyl]-amide | 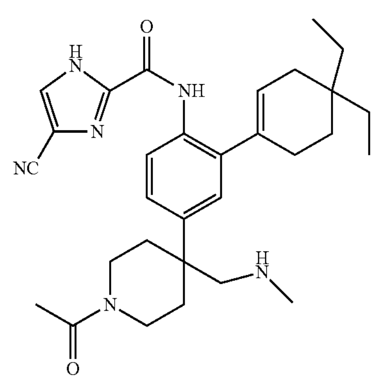 [SMILES: CCC1(CC)CC=C(c2cc(C3(CNC)CCN(C(C)=O)CC3)ccc2NC(=O)c2nc(C#N)c[nH]2)CC1] | Ex. 77, steps (a) and (b) | (WO 2005063705) (*Canadian J. Chem.* 59, 2673 (1981)) |

| Example No. | Name | Structure | Procedure Reference | Reagents |
|---|---|---|---|---|
| 81 | 4-Cyano-1H-imidazole-2-carboxylic acid [2-(4,4-dimethyl-cyclohex-1-enyl)-4-(4-methylaminomethyl-1,1-dioxo-hexahydro-1λ⁶-thiopyran-4-yl)-phenyl]-amide | 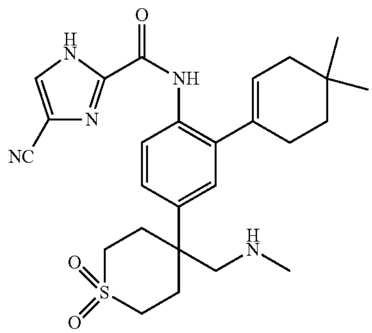 [SMILES: CNCC1(c2ccc(NC(=O)c3nc(C#N)c[nH]3)c(C3=CCC(C)(C)CC3)c2)CCS(=O)(=O)CC1] | Ex. 74, step (a); Ex. 73, step (b)-(d); Ex. 76, step (a) | |

Example 82

4-Cyano-1H-imidazole-2-carboxylic acid {2-(4,4-dimethyl-cyclohex-1-enyl)-6-[4-(4-methyl-piperazin-1-yl)-tetrahydro-pyran-4-yl]-pyridin-3-yl}-amide

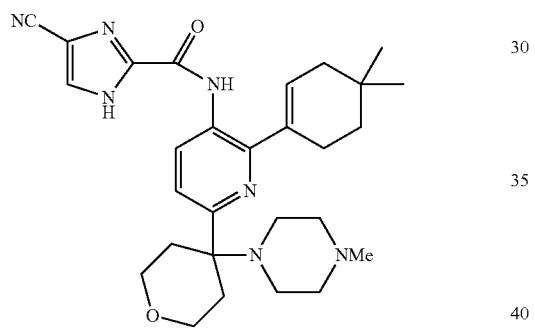

a) 4-Cyano-1H-imidazole-2-carboxylic acid [2-(4,4-dimethyl-cyclohex-1-enyl)-6-(4-hydroxy-tetrahydro-pyran-4-yl)-pyridin-3-yl]-amide

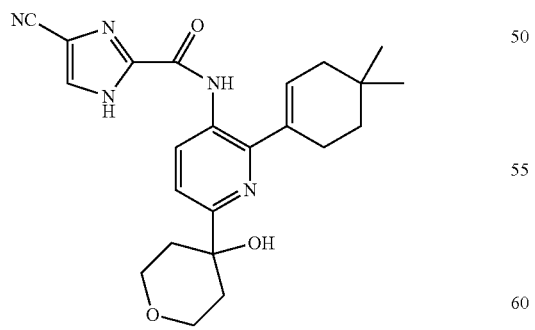

The title compound was prepared from 5-cyano-1H-imidazole-2-carboxylic acid [6-bromo-2-(4,4-dimethyl-cyclohex-1-enyl)-pyridin-3-yl]-amide (as prepared in Example 32, step (d)) and tetrahydro-pyran-4-one according to the procedure in Example 1, step (h).

b) 4-Cyano-1H-imidazole-2-carboxylic acid {2-(4,4-dimethyl-cyclohex-1-enyl)-6-[4-(4-methyl-piperazin-1-yl)-tetrahydro-pyran-4-yl]-pyridin-3-yl}-amide The title compound is prepared from 4-cyano-1H-imidazole-2-carboxylic acid [2-(4,4-dimethyl-cyclohex-1-enyl)-6-(4-hydroxy-tetrahydro-pyran-4-yl)-pyridin-3-yl]-amide (as prepared in the previous step) and N-methylpiperazine according to the procedure in Example 4.

The following examples are produced according to procedures of previous examples with the corresponding reagents as indicated in the table below:

| Example No. | Name | Structure | Procedure Reference | Reagents |
|---|---|---|---|---|
| 83 | 4-Cyano-1H-imidazole-2-carboxylic acid {2-(4,4-dimethyl-cyclohex-1-enyl)-6-[4-(2-morpholin-4-yl-ethylamino)-tetrahydro-pyran-4-yl]-pyridin-3-yl}-amide | 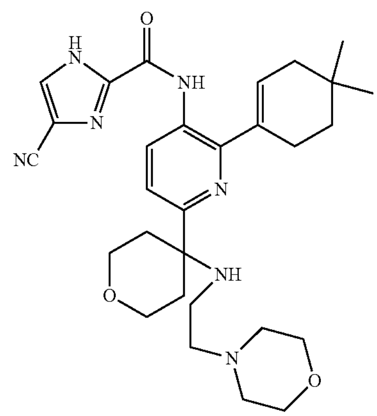 [SMILES: CC1(C)CC=C(c2nc(C3(NCCN4CCOCC4)CCOCC3)ccc2NC(=O)c2nc(C#N)c[nH]2)CC1] | Example 82 | (Combi-Blocks) |
| 84 | 4-Cyano-1H-imidazole-2-carboxylic acid {2-(4,4-diethyl-cyclohex-1-enyl)-6-[4-(3-dimethylamino-propoxy)-tetrahydro-pyran-4-yl]-pyridin-3-yl}-amide | 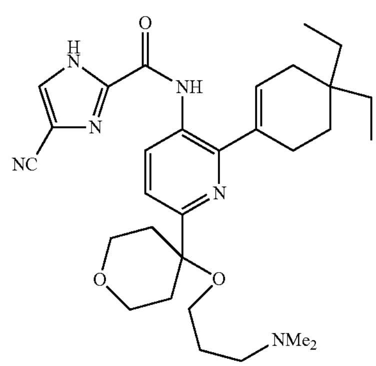 [SMILES: CCC1(CC)CC=C(c2nc(C3(OCCCN(C)C)CCOCC3)ccc2NC(=O)c2nc(C#N)c[nH]2)CC1] | Example 82, step (a); Ex. 2 | (WO 2005063705) |
| 85 | 4-Cyano-1H-imidazole-2-carboxylic acid {2-(4,4-dimethyl-cyclohex-1-enyl)-6-[4-(4-ethyl-piperazin-1-yl)-tetrahydro-pyran-4-yl]-pyridin-3-yl}-amide | 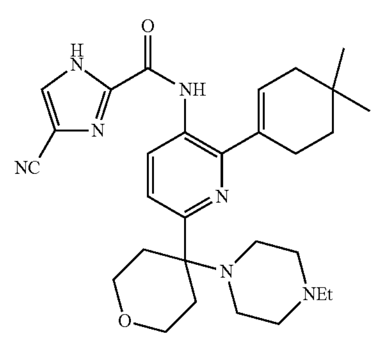 | Ex. 82 | (Combi-Blocks) |

Example 86

4-Cyano-1H-imidazole-2-carboxylic acid [2-(4-methyl-piperidin-1-yl)-4-(4-pyrrolidin-1-ylmethyl-tetrahydro-pyran-4-yl)-phenyl]-amide

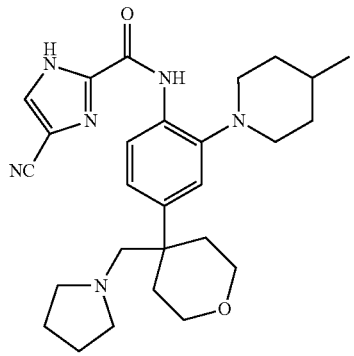 [SMILES: CC1CCN(c2cc(C3(CN4CCCC4)CCOCC3)ccc2NC(=O)c2nc(C#N)c[nH]2)CC1]

a) 4-[3-(4-Methyl-piperidin-1-yl)-4-nitro-phenyl]-tetrahydro-pyran-4-carboxylic acid methyl ester

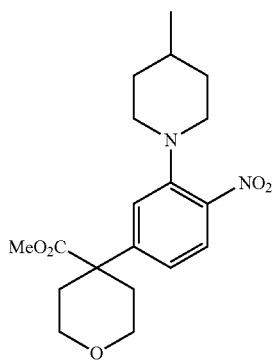 [SMILES: COC(=O)C1(c2ccc([N+](=O)[O-])c(N3CCC(C)CC3)c2)CCOCC1]

The title compound is prepared by the procedure of Example 16, step (a) using tetrahydro-pyran-4-carboxylic acid methyl ester and 1-(5-bromo-2-nitro-phenyl)-4-methyl-piperidine (US 2005131022 A1).

b) 4-[4-Amino-3-(4-methyl-piperidin-1-yl)-phenyl]-tetrahydro-pyran-4-carboxylic acid methyl ester

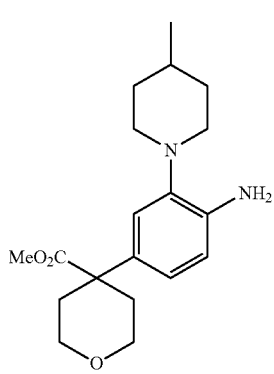 [SMILES: COC(=O)C1(c2ccc(N)c(N3CCC(C)CC3)c2)CCOCC1]

The title compound is prepared by the reaction procedure of Example 16, step (b) using 4-[3-(4-methyl-piperidin-1-yl)-4-nitro-phenyl]-tetrahydro-pyran-4-carboxylic acid methyl ester (as prepared in the previous step).

c) 4-[4-{[4-Cyano-1-(2-trimethylsilanyl-ethoxymethyl)-1H-imidazole-2-carbonyl]-amino}-3-(4-methyl-piperidin-1-yl)-phenyl]-tetrahydro-pyran-4-carboxylic acid methyl ester

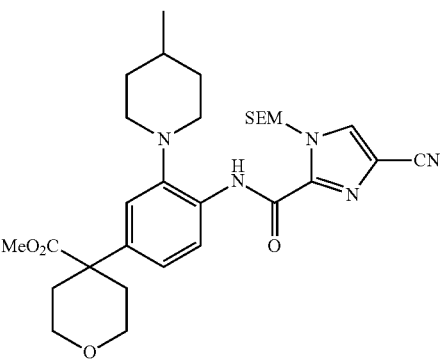 [SMILES: COC(=O)C1(c2ccc(NC(=O)c3nc(C#N)cn3COCC[Si](C)(C)C)c(N3CCC(C)CC3)c2)CCOCC1]

The title compound is prepared by the procedure of Example 16, step (e) using 4-[4-amino-3-(4-methyl-piperidin-1-yl)-phenyl]-tetrahydro-pyran-4-carboxylic acid methyl ester (as prepared in the previous step) and potassium 4-cyano-1-(2-trimethylsilanyl-ethoxymethyl)-1H-imidazole-2-carboxylate (as prepared in Example 1, step (d)).

d) 4-[4-[(4-Cyano-1H-imidazole-2-carbonyl)-amino]-3-(4-methyl-piperidin-1-yl)-phenyl]-tetrahydro-pyran-4-carboxylic acid methyl ester

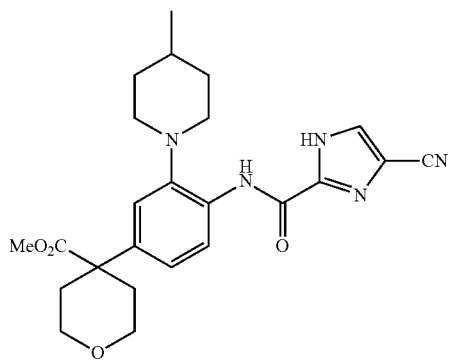 [SMILES: COC(=O)C1(c2ccc(NC(=O)c3nc(C#N)c[nH]3)c(N3CCC(C)CC3)c2)CCOCC1]

The title compound is prepared by the procedure of Example 16, step (f) using 4-[4-{[4-cyano-1-(2-trimethylsilanyl-ethoxymethyl)-1H-imidazole-2-carbonyl]-amino}-3-(4-methyl-piperidin-1-yl)-phenyl]-tetrahydro-pyran-4-carboxylic acid methyl ester (as prepared in the previous step).

e) 4-Cyano-1H-imidazole-2-carboxylic acid [4-(4-hydroxymethyl-tetrahydro-pyran-4-yl)-2-(4-methyl-piperidin-1-yl)-phenyl]-amide

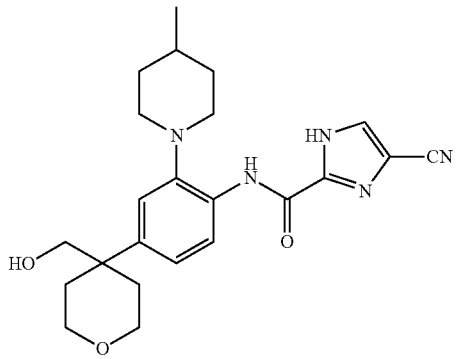 [SMILES: CC1CCN(c2cc(C3(CO)CCOCC3)ccc2NC(=O)c2nc(C#N)c[nH]2)CC1]

The title compound is prepared by the procedure of Example 25 using 4-[4-[(4-cyano-1H-imidazole-2-carbonyl)-amino]-3-(4-methyl-piperidin-1-yl)-phenyl]-tetrahydro-pyran-4-carboxylic acid methyl ester (as prepared in the previous step).

f) 4-Cyano-1H-imidazole-2-carboxylic acid [4-(4-formyl-tetrahydro-pyran-4-yl)-2-(4-methyl-piperidin-1-yl)-phenyl]-amide

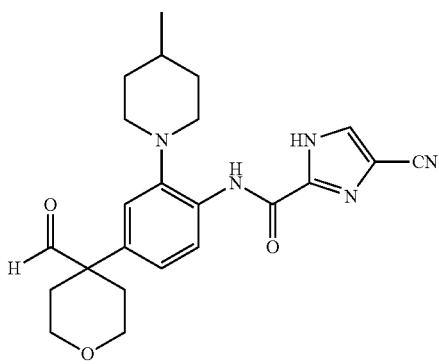 [SMILES: CC1CCN(c2cc(C3(C=O)CCOCC3)ccc2NC(=O)c2nc(C#N)c[nH]2)CC1]

The title compound is prepared by the procedure of Example 26, step (a) using 4-cyano-1H-imidazole-2-carboxylic acid [4-(4-hydroxymethyl-tetrahydro-pyran-4-yl)-2-(4-methyl-piperidin-1-yl)-phenyl]-amide (as prepared in the previous step).

g) 4-Cyano-1H-imidazole-2-carboxylic acid [2-(4-methyl-piperidin-1-yl)-4-(4-pyrrolidin-1-ylmethyl-tetrahydro-pyran-4-yl)-phenyl]-amide The title compound is prepared by the procedure of Example 26, step (b) using 4-cyano-1H-imidazole-2-carboxylic acid [4-(4-formyl-tetrahydro-pyran-4-yl)-2-(4-methyl-piperidin-1-yl)-phenyl]-amide (as prepared in the previous step) and pyrrolidine.

Example 87

4-Cyano-1H-imidazole-2-carboxylic acid [4-(4-cyano-1,1-dioxo-hexahydro-1$\lambda^6$-thiopyran-4-yl)-2-(4,4-dimethyl-cyclohex-1-enyl)-phenyl]-amide

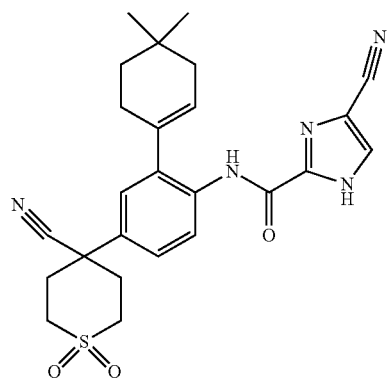 [SMILES: CC1(C)CC=C(c2cc(C3(C#N)CCS(=O)(=O)CC3)ccc2NC(=O)c2nc(C#N)c[nH]2)CC1]

a) 4-(4-Nitro-phenyl)-1,1-dioxo-hexahydro-1$\lambda^6$-thiopyran-4-carbonitrile

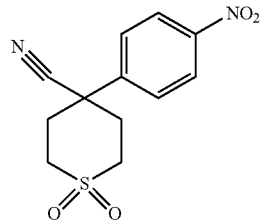 [SMILES: N#CC1(c2ccc([N+](=O)[O-])cc2)CCS(=O)(=O)CC1]

A slurry of NaH (71.4 mg, 1.79 mmol, 60% dispersion) in DMSO (3 mL) and THF (1 mL) was treated with solid (4-nitro-phenyl)-acetonitrile (121 mg, 0.744 mmol) and stirred at RT for 3 min. A solution of 1-bromo-2-(2-bromoethanesulfonyl)-ethane (250 mg, 0.893 mmol) in THF (3 mL) was added, and the mixture was heated to 70° C. for 1.5 h. The mixture was partitioned between EtOAc (100 mL) and water (75 mL), and brine (25 mL) was added. The aqueous layer was extracted with EtOAc (1×50 mL). The combined organic layers were dried over MgSO$_4$ and concentrated in vacuo. Silica gel chromatography of the residue on a 20-g Isolute SPE column with 10-50% EtOAc-hexane afforded the title compound (205 mg, 98%) as a white solid. $^1$H-NMR (CDCl$_3$;

400 MHz): δ 8.33 (d, 2H, J=8.8 Hz), 7.75 (d, 2H, J=8.8 Hz), 3.64-3.52 (m, 2H), 3.29-3.19 (m, 2H), 2.88-2.76 (m, 2H), 2.54-2.44 (m, 2H).

b) 4-(4-Amino-phenyl)-1,1-dioxo-hexahydro-1$\lambda^6$-thiopyran-4-carbonitrile

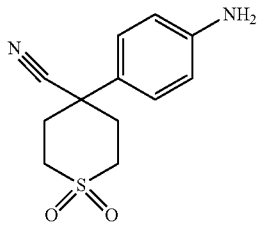 [SMILES: N#CC1(c2ccc(N)cc2)CCS(=O)(=O)CC1]

A suspension of 4-(4-nitro-phenyl)-1,1-dioxo-hexahydro-1$\lambda^6$-thiopyran-4-carbonitrile (205 mg, 0.731 mmol, as prepared in the previous step) in EtOH (5 mL) and water (5 mL) was treated with solid NH$_4$Cl (204 mg, 3.66 mmol) and Fe powder (392 mg, 7.31 mmol) and heated to 50° C. for 1.5 h. The cooled mixture was filtered through Celite, and the filter cake was washed with MeOH. The solvents were evaporated in vacuo. The residue was diluted with water (30 mL) and extracted with EtOAc (2×30 mL). The combined organic layers were dried over MgSO$_4$ and concentrated in vacuo. Silica gel chromatography of the residue on a 50-g Varian MegaBond Elut SPE column with 50% EtOAc-hexane afforded the title compound (114 mg, 62%) as a pale yellow solid. Mass spectrum (ESI, m/z): Calcd. for $C_{12}H_{14}N_2O_2S$, 251.1 (M+H). found 251.2.

c) 4-(4-Amino-3-bromo-phenyl)-1,1-dioxo-hexahydro-1$\lambda^6$-thiopyran-4-carbonitrile

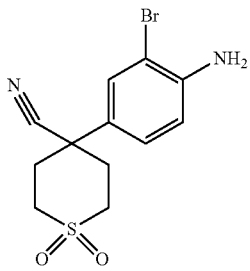 [SMILES: N#CC1(c2ccc(N)c(Br)c2)CCS(=O)(=O)CC1]

A solution of 4-(4-amino-phenyl)-1,1-dioxo-hexahydro-1$\lambda^6$-thiopyran-4-carbonitrile (114 mg, 0.455 mmol, as prepared in the previous step) in CH$_2$Cl$_2$ (15 mL) was cooled to 0° C., treated with solid NBS (77.0 mg, 0.433 mmol), and stirred at that temperature for 30 min. The mixture was diluted with CH$_2$Cl$_2$ (20 mL) and washed with satd aq NaHCO$_3$ (1×20 mL). The aqueous layer was extracted with CH$_2$Cl$_2$ (1×20 mL). The combined organic layers were dried over MgSO$_4$ and concentrated in vacuo. Silica gel chromatography of the residue on a 50-g Varian MegaBond Elut SPE column with 50% EtOAc-hexane afforded the title compound (136 mg, 90%) as a white solid. $^1$H-NMR (CDCl$_3$; 400 MHz): δ 7.53 (d, 1H, J=2.0 Hz), 7.23 (dd, 1H, J=8.4, 2.0 Hz), 6.79 (d, 1H, J=8.0 Hz), 4.40-4.15 (br s, 2H), 3.60-3.45 (m, 2H), 3.26-3.11 (m, 2H), 2.78-2.63 (m, 2H), 2.51-2.38 (m, 2H).

d) 4-[4-Amino-3-(4,4-dimethyl-cyclohex-1-enyl)-phenyl]-1,1-dioxo-hexahydro-1$\lambda^6$-thiopyran-4-carbonitrile

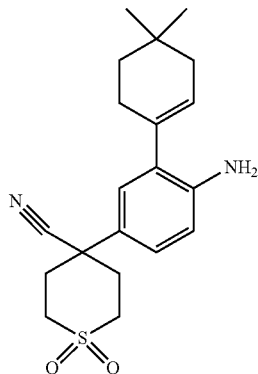 [SMILES: CC1(C)CC=C(c2cc(C3(C#N)CCS(=O)(=O)CC3)ccc2N)CC1]

A solution of 4-(4-amino-3-bromo-phenyl)-1,1-dioxo-hexahydro-1$\lambda^6$-thiopyran-4-carbonitrile (109 mg, 0.332 mmol, as prepared in the previous step) in DMF (4 mL) was treated with 2-(4,4-dimethyl-cyclohex-1-enyl)-4,4,5,5-tetramethyl-[1,3,2]dioxaborolane (94.1 mg, 0.398 mmol) and aq Na$_2$CO$_3$ (1.32 mL, 2.66 mmol, 2.0 M). The mixture was degassed via sonication, placed under Ar, treated with Pd(dppf)Cl$_2$ (24.3 mg, 0.034 mmol), and heated to 60° C. for 24 h. The cooled mixture was diluted with EtOAc and water. The aqueous layer was extracted with EtOAc (4×). The combined organic layers were dried over MgSO$_4$ and concentrated in vacuo. Purification of the residue by silica gel chromatography on a 10-g Isolute SPE column (FlashMaster system) with 25% EtOAc-hexane afforded the title compound (119 mg, 100%) as a white solid. Mass spectrum (ESI, m/z): Calcd. for $C_{20}H_{26}N_2O_2S$, 359.2 (M+H). found 359.3.

e) 4-Cyano-1-(2-trimethylsilanyl-ethoxymethyl)-1H-imidazole-2-carboxylic acid [4-(4-cyano-1,1-dioxo-hexahydro-1$\lambda^6$-thiopyran-4-yl)-2-(4,4-dimethyl-cyclohex-1-enyl)-phenyl]-amide

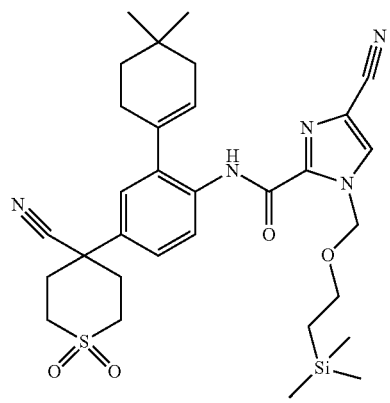 [SMILES: CC1(C)CC=C(c2cc(C3(C#N)CCS(=O)(=O)CC3)ccc2NC(=O)c2nc(C#N)cn2COCC[Si](C)(C)C)CC1]

A solution of 4-[4-amino-3-(4,4-dimethyl-cyclohex-1-enyl)-phenyl]-1,1-dioxo-hexahydro-1$\lambda^6$-thiopyran-4-carbonitrile (119 mg, 0.332 mmol, as prepared in the previous step)

and 4-cyano-1-(2-trimethylsilanyl-ethoxymethyl)-1H-imidazole-2-carboxylate potassium salt (123 mg, 0.398 mmol, as prepared in Example 1, step (d)) in CH$_2$Cl$_2$ (10 mL) was treated with PyBroP (217 mg, 0.465 mmol) and DIEA (231 μL, 1.33 mmol) at room temperature for 45 min. The mixture was diluted with CH$_2$Cl$_2$ (30 mL) and washed with satd aq NaHCO$_3$ (1×30 mL). The aqueous layer was extracted with CH$_2$Cl$_2$ (1×30 mL), and the combined organic layers were dried over MgSO$_4$ and concentrated in vacuo. Silica gel chromatography of the residue on a 20-g Isolute SPE column (FlashMaster system) with 10-25% EtOAc-hexane afforded the title compound (193 mg, 95%) as an off-white solid. Mass spectrum (ESI, m/z): Calcd. for C$_{31}$H$_{41}$N$_5$O$_4$SSi, 608.3 (M+H). found 608.3.

f) 4-Cyano-1H-imidazole-2-carboxylic acid [4-(4-cyano-1,1-dioxo-hexahydro-1λ$^6$-thiopyran-4-yl)-2-(4,4-dimethyl-cyclohex-1-enyl)-phenyl]-amide A solution of 4-cyano-1-(2-trimethylsilanyl-ethoxymethyl)-1H-imidazole-2-carboxylic acid [4-(4-cyano-1,1-dioxo-hexahydro-1λ$^6$-thiopyran-4-yl)-2-(4,4-dimethyl-cyclohex-1-enyl)-phenyl]-amide (193 mg, 0.318 mmol, as prepared in the previous step) in CH$_2$Cl$_2$ (10 mL) was treated with TFA (2 mL) and stirred at RT for 3 h. EtOH (5 mL) was added, and the mixture was concentrated to dryness. The residue was taken up in CH$_2$Cl$_2$ and carefully washed with satd aq NaHCO$_3$ (1×). The aqueous layer was extracted with CH$_2$Cl$_2$ (1×), and the combined aqueous layers were dried over MgSO$_4$ and concentrated in vacuo. Silica gel chromatography of the residue on a 20-g Isolute SPE column (FlashMaster system) with 25-50% EtOAc-hexane afforded the title compound (50.4 mg, 33%) as a white solid. $^1$H-NMR (CD$_3$OD; 400 MHz): δ 8.39 (d, 1H, J=8.8 Hz), 8.01 (s, 1H), 7.53 (dd, 1H, J=8.8, 2.0 Hz), 7.42 (d, 1H, J=2.0 Hz), 5.85-5.80 (m, 1H), 3.59-3.46 (m, 2H), 2.81-2.69 (m, 2H), 2.62-2.52 (m, 2H), 2.39-2.32 (m, 2H), 2.17-2.10 (m, 2H), 1.68-1.58 (m, 4H), 1.13 (s, 6H). Mass spectrum (ESI, m/z): Calcd. for C$_{25}$H$_{27}$N$_5$O$_3$S, 478.2 (M+H). found 478.2.

Example 88

4-Cyano-1H-imidazole-2-carboxylic acid [2-(4,4-dimethyl-cyclohex-1-enyl)-4-(4-hydroxy-2,2,6,6-tetramethyl-tetrahydro-pyran-4-yl)-phenyl]-amide

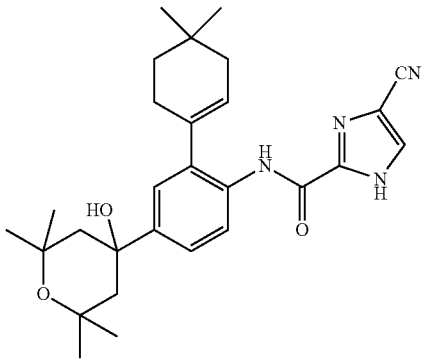 [SMILES: CC1(C)CC=C(c2cc(C3(O)CC(C)(C)OC(C)(C)C3)ccc2NC(=O)c2nc(C#N)c[nH]2)CC1]

The title compound was prepared as described in Example 1, step (h) using 4-cyano-1H-imidazole-2-carboxylic acid [4-bromo-2-(4,4-dimethyl-cyclohex-1-enyl)-phenyl]-amide (as prepared in Example 1, step (g) and 2,2,6,6-tetramethyl tetrahydropyran-4-one (WO 2005012220). $^1$H-NMR (CD$_3$OD; 400 MHz): δ 8.16 (d, 1H, J=8.4 Hz), 7.98 (s, 1H), 7.38 (dd, 1H, J=8.4, 2.0 Hz), 7.34 (d, 1H, J=2.0 Hz), 5.74 (br s, 1H), 2.32 (m, 2H), 2.08 (m, 2H), 1.87 (m, 4H), 1.56-1.58 (m, 8H), 1.56 (s, 6H), 1.21 (s, 6H).

Example 89

4-Cyano-1H-imidazole-2-carboxylic acid [2-(4,4-dimethyl-cyclohex-1-enyl)-4-(4-hydroxy-1-methoxy-2,2,6,6-tetramethyl-piperidin-4-yl)-phenyl]-amide

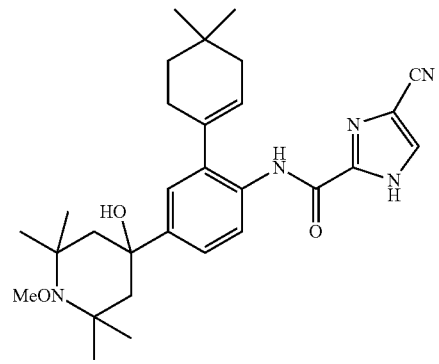

The title compound was prepared as described in Example 1 step (h) using 4-cyano-1H-imidazole-2-carboxylic acid [4-bromo-2-(4,4-dimethyl-cyclohex-1-enyl)-phenyl]-amide (as prepared in Example 1, step (g) and 1-methoxy-2,2,6,6-tetramethyl-piperidin-4-one (WO 9854174). $^1$H-NMR (CD$_3$OD; 400 MHz): δ 8.21 (d, 1H, J=8.4 Hz), 8.01 (s, 1H), 7.45 (dd, 1H, J=8.4, 2.0 Hz), 7.37 (d, 1H, J=2.0 Hz), 5.75 (br s, 1H), 4.08 (s, 3H), 2.35 (m, 4H), 2.09 (m, 4H), 1.72 (s, 6H), 1.61 (m, 2H), 1.50 (s, 6H), 1.10 (s, 6H). Mass spectrum (ESI, m/z): Calcd. for C$_{29}$H$_{39}$N$_5$O$_3$, 506.3 (M+H). found 506.3.

Example 90

4-Cyano-1H-imidazole-2-carboxylic acid {2-(4,4-dimethyl-cyclohex-1-enyl)-4-[4-hydroxy-1-(2,2,2-trifluoro-ethyl)-piperidin-4-yl]-phenyl}-amide

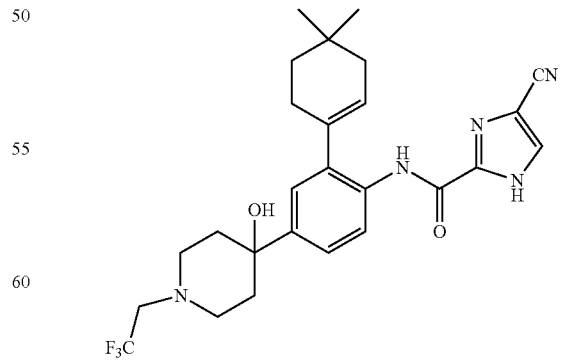

The title compound was prepared as described in Example 1, step (h) using 4-cyano-1H-imidazole-2-carboxylic acid [4-bromo-2-(4,4-dimethyl-cyclohex-1-enyl)-phenyl]-amide (as prepared in Example 1, step (g) and 1-(2,2,2-trifluoro-ethyl)-piperidin-4-one (WO 9621452). ¹H-NMR (CD₃OD; 400 MHz): δ 12.9 (br s, 1H), 9.62 (s, 1H), 8.21 (d, 1H, J=8.4 Hz), 7.63 (s, 1H), 7.38 (dd, 1H, J=8.4, 2.0 Hz), 7.24 (d, 1H, J=2.0 Hz), 5.73 (br s, 1H), 4.13 (m, 2H), 2.91-3.23 (m, 4H), 1.93-2.32 (m, 4H), 1.53 (m, 2H), 1.08 (s, 6H). Mass spectrum (ESI, m/z): Calcd. for $C_{26}H_{30}F_3N_5O_2$, 502.5 (M+H). found 502.2.

Example 91

4-Cyano-1H-imidazole-2-carboxylic acid {2-(4,4-dimethyl-cyclohex-1-enyl)-4-[4-hydroxy-2,2,6,6-tetramethyl-1-(2,2,2-trifluoro-ethyl)-piperidin-4-yl]-phenyl}-amide

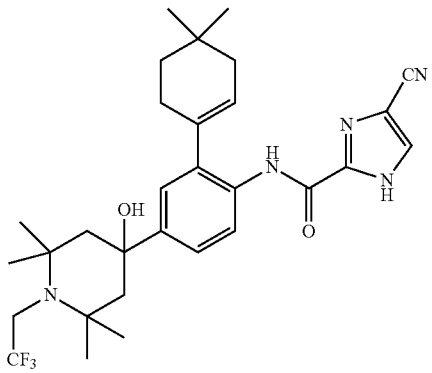 [SMILES: CC1(C)CC=C(c2cc(C3(O)CC(C)(C)N(CC(F)(F)F)C(C)(C)C3)ccc2NC(=O)c2nc(C#N)c[nH]2)CC1]

a) 2,2,6,6-Tetramethyl-1-(2,2,2-trifluoro-ethyl)-piperidin-4-one

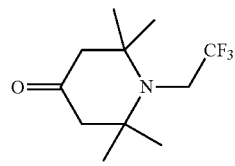 [SMILES: CC1(C)CC(=O)CC(C)(C)N1CC(F)(F)F]

To a solution of 2,2,6,6-tetramethyl-1-(2,2,2-trifluoro-ethyl)-piperidin-4-ol (780 mg, 3.25 mmol; *J. Phys. Org. Chem.*, 16(3), 175-182 (2003)) in DCM (50 mL) Dess-Martin periodinane (1.6 g, 3.2 mmol; *Adv. Syn. Catalysis,* 346, 111-124 (2004)) was added portionwise at 0° C. The resulting mixture was stirred at RT for 48 h, diluted with satd NaHCO₃ (50 mL) and was extracted with DCM (3×25 mL). The organic layers were combined, dried (Na₂SO₄) and concentrated in vacuo. The resulting oil was chromatographed on silica (10-50% EtOAc/hexane) to obtain the title compound 309 mg, 40%. Mass spectrum (ESI, m/z): Calcd. for $C_{11}H_{18}F_3N$, 238.1 (M+H). found 238.0.

b) 4-Cyano-1H-imidazole-2-carboxylic acid {2-(4,4-dimethyl-cyclohex-1-enyl)-4-[4-hydroxy-2,2,6,6-tetramethyl-1-(2,2,2-trifluoro-ethyl)-piperidin-4-yl]-phenyl}-amide The title compound was prepared as described in Example 1, step (h) using 4-cyano-1H-imidazole-2-carboxylic acid [4-bromo-2-(4,4-dimethyl-cyclohex-1-enyl)-phenyl]-amide (as prepared in Example 1, step (g) and 2,2,6,6-tetramethyl-1-(2,2,2-trifluoro-ethyl)-piperidin-4-one (as prepared above). ¹H-NMR (CD₃OD; 400 MHz): δ 8.22 (d, 1H, J=8.4 Hz), 7.98 (s, 1H), 7.43 (dd, 1H, J=8.4, 2.0 Hz), 7.33 (d, 1H, J=2.0 Hz), 5.73 (br s, 1H), 4.18 (m, 2H), 2.28-2.36 (m, 4H), 2.08 (m, 4H), 1.73 (s, 6H), 1.58 (m, 2H), 1.42 (m, 6H), 1.08 (s, 6H). Mass spectrum (ESI, m/z): Calcd. for $C_{30}H_{38}F_3N_5O_2$, 558.3 (M+H). found 558.0.

Example 92

4-Cyano-1H-imidazole-2-carboxylic acid [2-(4,4-dimethyl-cyclohex-1-enyl)-4-(3-hydroxy-8-oxa-bicyclo[3.2.1]oct-3-yl)-phenyl]-amide

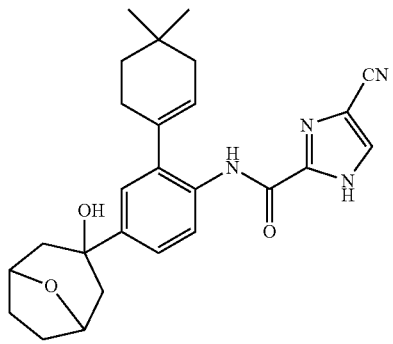 [SMILES: CC1(C)CC=C(c2cc(C3(O)CC4CCC(C3)O4)ccc2NC(=O)c2nc(C#N)c[nH]2)CC1]

The title compound was prepared as described in Example 1, step (h) using 4-cyano-1H-imidazole-2-carboxylic acid [4-bromo-2-(4,4-dimethyl-cyclohex-1-enyl)-phenyl]-amide (as prepared in Example 1, step (g)) and 8-oxa-bicyclo[3.2.1]octan-3-one (*Liebigs Annalen der Chemie*, (1), 1-5 (1987)). ¹H-NMR (CDCl₃; 400 MHz): δ 11.69 (br s, 1H), 9.56 (s, 1H), 8.36 (d, 1H, J=8.4 Hz), 7.70 (s, 1H), 7.48 (dd, 1H, J=8.4, 2.0 Hz), 7.30 (d, 1H, J=2.0 Hz), 5.79-5.74 (m, 1H), 4.58-4.50 (m, 2H), 2.48-2.41 (m, 2H), 2.40-2.37 (m, 2H), 2.32-2.25 (m, 2H), 2.12-2.07 (m, 2H), 2.05-1.96 (m, 2H), 1.83-1.76 (m, 2H), 1.57-1.53 (m, 2H), 1.10 (s, 6H). Mass spectrum (ESI, m/z): Calcd. for $C_{26}H_{30}N_4O_3$, 447.2 (M+H). found 447.1.

Example 93

4-Cyano-1H-imidazole-2-carboxylic acid [2-(4,4-dimethyl-cyclohex-1-enyl)-4-(3-hydroxy-1,5-dimethyl-8-oxa-bicyclo[3.2.1]oct-3-yl)-phenyl]-amide

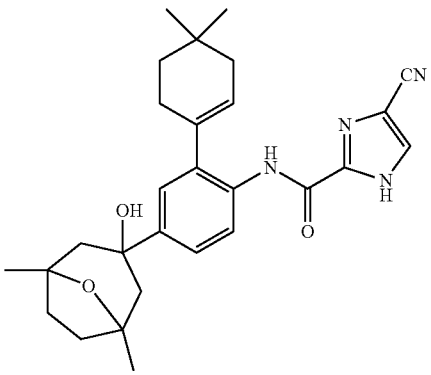 [SMILES: CC1(C)CC=C(c2cc(C3(O)CC4(C)CCC(C)(C3)O4)ccc2NC(=O)c2nc(C#N)c[nH]2)CC1]

The title compound was prepared as described in Example 1, step (h) using 4-cyano-1H-imidazole-2-carboxylic acid [4-bromo-2-(4,4-dimethyl-cyclohex-1-enyl)-phenyl]-amide (as prepared in Example 1, step (g)) and 1,5-dimethyl-8-oxa-bicyclo[3.2.1]octan-3-one (*J. Org. Chem.*, 64(10), 3398-3408 (1999)). $^1$H-NMR (DMSO-$d_6$; 400 MHz): d 14.25 (bs, 1H), 9.72 (s, 1H), 8.29 (s, 1H), 7.90 (d, 1H, J=8.3 Hz), 7.33 (dd, 1H, J=2.3, 8.6 Hz), 7.27 (m, 1H), 5.65 (m, 1H), 4.88 (s, 1H), 2.42-2.37 (m, 2H), 2.26-2.22 (m, 2H), 1.95 (m, 2H), 1.81-1.71 (m, 4H), 1.53-1.47 (m, 4H), 1.23 (s, 6H), 1.00 (s, 6H). Mass spectrum (ESI, m/z): Calcd. for $C_{28}H_{34}N_4O_3$, 475.2 (M+1). found 475.1.

Example 94

4-Cyano-1H-imidazole-2-carboxylic acid [4-(3-cyano-1,5-dimethyl-8-oxa-bicyclo[3.2.1]oct-3-yl)-2-(4,4-dimethyl-cyclohex-1-enyl)-phenyl]-amide

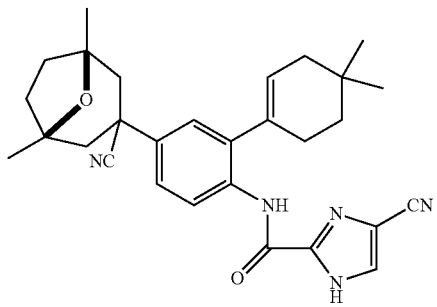 [SMILES: CC1(C)CC=C(c2cc(C3(C#N)C[C@]4(C)CC[C@](C)(C3)O4)ccc2NC(=O)c2nc(C#N)c[nH]2)CC1]

To a slurry of 4-cyano-1H-imidazole-2-carboxylic acid [2-(4,4-dimethyl-cyclohex-1-enyl)-4-(3-hydroxy-1,5-dimethyl-8-oxa-bicyclo[3.2.1]oct-3-yl)-phenyl]-amide (21 mg, 0.044 mmol, as prepared in Example 93) in 1 mL of DCM at 0° C. was added TMSCN (25 μL, 0.19 mmol) followed by SnCl$_4$ (4 mg, 0.01 mmol) dissolved in 0.08 mL of DCM. The reaction was warmed to room temperature and again treated with 25 μL of TMSCN and then SnCl$_4$ (8 mg, 0.02 mmol) in 0.2 mL of DCM. After the reaction became homogeneous 1 mL of MeOH was added followed by 2 mL of water. The mixture was stirred for 5 min, CHCl$_3$ (5 mL) was added and the layers were separated. The organic layer was dried (Na$_2$SO$_4$) and concentrated in vacuo. Purification of the residue twice by preparative TLC (5% MeOH—CHCl$_3$, then 50% EtOAc-hexanes) afforded the title compound (6 mg, 28%). $^1$H-NMR (CD$_3$OD; 400 MHz): δ 8.09 (d, 1H, J=8.3 Hz), 7.70 (s, 1H), 7.27-7.23 (m, 1H), 7.16-7.12 (m, 1H), 5.66-5.64 (m, 1H), 2.80-2.56 (m, 4H), 2.22-2.14 (m, 2H), 2.02-1.97 (m, 2H), 1.81-1.77 (m, 4H), 1.51-1.46 (m, 2H), 1.25 (s, 3H), 1.25 (s, 1H), 0.98 (s, 6H). Mass spectrum (ESI, m/z): Calcd. for $C_{29}H_{33}N_5O_2$ 484.2 (M+1). found 484.0.

Example 95

4-Cyano-1H-imidazole-2-carboxylic acid [4-(4-cyano-2,2,6,6-tetramethyl-tetrahydro-pyran-4-yl)-2-(4,4-dimethyl-cyclohex-1-enyl)-phenyl]-amide

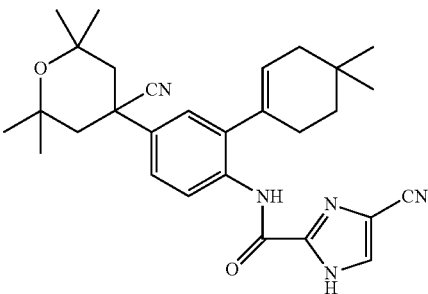 [SMILES: CC1(C)CC=C(c2cc(C3(C#N)CC(C)(C)OC(C)(C)C3)ccc2NC(=O)c2nc(C#N)c[nH]2)CC1]

The title compound was prepared as described in Example 94 using 4-cyano-1H-imidazole-2-carboxylic acid [2-(4,4-dimethyl-cyclohex-1-enyl)-4-(4-hydroxy-2,2,6,6-tetra-methyl-tetrahydro-pyran-4-yl)-phenyl]-amide (as prepared in Example 88): $^1$H-NMR (CD$_3$OD; 400 MHz): δ 8.47 (d, 1H, J=8.6 Hz), 8.00 (s, 1H), 7.62 (dd, 1H, J=2.5, 8.6 Hz), 7.52 (m, 1H), 5.94 (m, 1H), 2.53-2.49 (m, 4H), 2.25 (m, 2H), 2.02-1.99 (m, 2H), 1.79-1.75 (m, 8H), 1.45 (s, 6H), 1.25 (s, 6H). Mass spectrum (ESI, m/z): Calcd. for $C_{29}H_{35}N_5O_2$, 486.2 (M+H). found 486.2.

IV. RESULTS

Fluorescence Polarization Competition Immunoassay

An autophosphorylation, fluorescence polarization competition immunoassay was used to determine the potency for c-fms inhibition exhibited by selected compounds of Formula I. The assay was performed in black 96-well microplates (LJL BioSystems). The assay buffer used was 100 mM 4-(2-hydroxyethyl)piperazine 1-ethanesulfonic acid (HEPES), pH 7.5, 1 mM 1,4-dithio-DL-threitol (DTT), 0.01% (v/v) Tween-20. Compounds were diluted in assay buffer containing 4% dimethylsulfoxide (DMSO) just prior to the assay. To each well, 5 μL of compound were added followed by the addition of 3 μL of a mix containing 33 nM c-fms (Johnson & Johnson PRD) and 16.7 mM MgCl$_2$ (Sigma) in assay buffer. The kinase reaction was initiated by adding 2 μL of 5 mM ATP (Sigma) in assay buffer. The final concentrations in the assay were 10 nM c-fms, 1 mM ATP, 5 mM MgCl$_2$, 2% DMSO. Control reactions were ran in each plate: in positive and negative control wells, assay buffer (made 4% in DMSO) was substituted for the compound; in addition, positive control wells received 1.2 μL of 50 mM ethylenediaminetetraaceticacid (EDTA).

The plates were incubated at room temperature for 45 min. At the end of the incubation, the reaction was quenched with 1.2 μL of 50 mM EDTA (EDTA was not added to the positive control wells at this point; see above). Following a 5-min incubation, each well received 10 μL of a 1:1:3 mixture of anti-phosphotyrosine antibody, 10×, PTK green tracer, 10× (vortexed), FP dilution buffer, respectively (all from PanVera, cat. #P2837). The plate was covered, incubated for 30 min at room temperature and the fluorescence polarization was read on the Analyst. The instrument settings were: 485 nm excitation filter; 530 nm emission filter; Z height: middle of well; G factor: 0.93. Under these conditions, the fluorescence polarization values for positive and negative controls were approximately 300 and 150, respectively, and were used to define the 100% and 0% inhibition of the c-fms reaction. The reported $IC_{50}$ values are averages of three independent measurements.

CSF-1-Driven Mouse Bone-Marrow Derived Macrophages Assay

Macrophages are derived by culturing mouse bone marrow in alpha-MEM supplemented with 10% FCS and 50 ng/ml recombinant mouse CSF-1 in bacteriologic dishes. On the sixth day, macrophages are detached from dishes, washed, and resuspended to 0.05 million cells/ml in alpha-MEM containing 10% FCS. One hundred ul of cell suspension are distributed per well into 96 well culture plates. Wells are further supplemented with the addition of 50 ul media containing 15 ng/ml CSF-1, 3 uM Indomethacin, and 3× of a dilution series of test compounds. The cells are cultured for 30 hrs at 37 degrees and 5% CO2. During the final six hours, cultures are supplemented with an additional 30 ul of media containing a 1:500 dilution of bromodeoxyuridine (BrDU). At the end of the culture period, the plates are spun at 1000 RPM for 1 minute and 130 ul of media is removed with a pipet and replaced with 150 ul of fixative solution for 1 hour @ room temperature. The fixative is then dispelled from the plates and the plates allowed to air dry. Incorporation of BrDU into the fixed, dried cells is quantified using a specific ELISA.

Table 2 lists the assay results for representative compounds of the invention.

TABLE 2

| Example # | 1 nM c-fms; peptide Pi assay IC-50 (µM) | mCSF driven proliferation BMDM (Mouse) IC-50 (µM) |
|---|---|---|
| 1 | 0.0007 | 0.004 |
| 2 | 0.00042 | 0.0022 |
| 3 | 0.0017 | N/A |
| 4 | 0.0018 | 0.014 |
| 5 | 0.0005 | 0.0024 |
| 6 | 0.0016 | 0.015 |
| 7 | 0.00067 | 0.011 |
| 8 | 0.004 | 0.015 |
| 9 | 0.0019 | 0.1 |
| 10 | 0.0079 | >0.3 |
| 11 | 0.0029 | 0.035 |
| 12 | 0.0011 | 0.031 |
| 13 | 0.0008 | 0.0081 |
| 14 | 0.0039 | 0.0095 |
| 15 | 0.0029 | 0.014 |
| 16 | 0.00067 | 0.046 |
| 17 | 0.00056 | >0.3 |
| 18 | 0.0036 | 0.3 |
| 19 | 0.0018 | 0.019 |
| 20 | 0.0018 | 0.02 |
| 21 | 0.0016 | 0.0079 |
| 22 | 0.0008 | >0.3 |
| 23 | 0.0064 | >0.3 |
| 24 | 0.0008 | 0.014 |
| 25 | 0.00049 | 0.0065 |
| 26 | 0.003 | 0.0053 |
| 27 | 0.0029 | 0.0045 |
| 28 | 0.0084 | 0.028 |
| 29 | 0.0016 | 0.011 |
| 30 | 0.0032 | 0.007 |
| 31 | 0.0014 | 0.003 |
| 32 | 0.0032 | 0.019 |
| 33 | 0.0037 | 0.033 |
| 34 | 0.0015 | 0.0172 |
| 35 | 0.0007 | 0.0058 |
| 87 | 0.0011 | 0.0082 |
| 88 | 0.0024 | 0.0064 |
| 89 | 0.013 | 0.02 |
| 90 | 0.0065 | 0.04 |
| 91 | ~0.21 | 0.061 |
| 92 | 0.0022 | 0.012 |
| 93 | 0.0029 | 0.0089 |
| 94 | 0.082 | >0.1 |
| 95 | 0.026 | 0.029 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

The claimed invention is:

1. A compound of Formula I

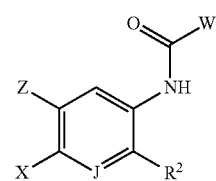

or a tautomer or pharmaceutically acceptable salt thereof, wherein:

W is

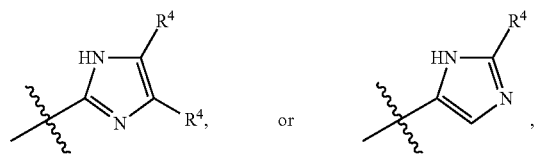

wherein each $R^4$ is independently H, F, Cl, Br, I, OH, $OCH_3$, $OCH_2CH_3$, $SC_{(1-4)}$alkyl, $SOC_{(1-4)}$alkyl, $SO_2C_{(1-4)}$alkyl, —$C_{(1-3)}$alkyl, $CO_2R^d$, $CONR^eR^f$, C≡$CR^g$, or CN;

wherein $R^d$ is H, or —$C_{(1-3)}$alkyl;

$R^e$ is H, or —$C_{(1-3)}$alkyl;

$R^f$ is H, or —$C_{(1-3)}$alkyl; and $R^g$ is H, —$CH_2OH$, or —$CH_2CH_2OH$;

$R^2$ is cycloalkyl, spiro-substituted cycloalkenyl, or phenyl, each of which is optionally independently substituted with one or two of each of the following: chloro, fluoro, hydroxy, $C_{(1-3)}$alkyl, and $C_{(1-4)}$alkyl.

2. The Compound of claim 1 wherein
W is

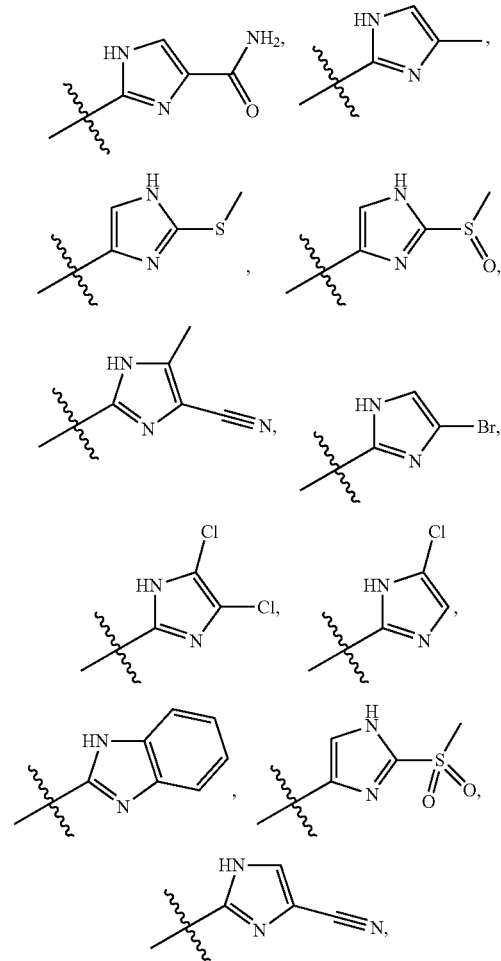

R² is

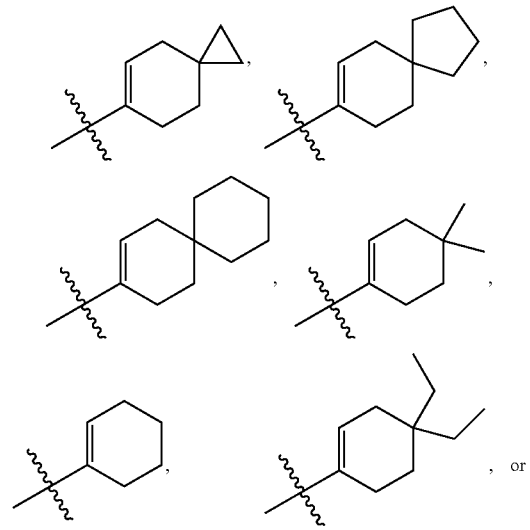

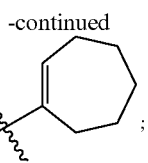

Z is H;
X is

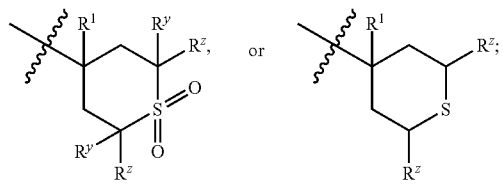

wherein R¹ is —OH, —CN, —NA¹A², —SO₂CH₃, —COORᵃ, —CO₂CH₃, —CH₂—NA¹A², —CONA¹A², —CH₂ORᵃ, —NHCH₂CH₂CO₂Rᵃ, —NHCH₂CH₂ORᵃ, —NHCH₂CH₂NA¹A², —OC₍₁₋₄₎alkylNA¹A², or —OCH₂CO₂Rᵃ;
A¹ is H, or —CH₃;
Z is H, F, or CH₃;
J is CH;
X is

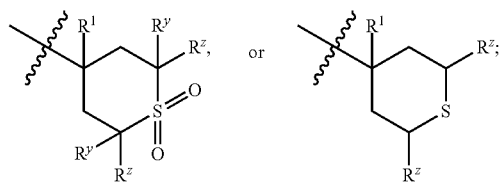

wherein R¹ is ORᵃ, —CN, —NA¹A², —SO₂CH₃, —COORᵃ, —CO₂CH₃, —CH₂—NA¹A², —CONA¹A², —CH₂ORᵃ, —OC₍₁₋₄₎alkylORᵃ, —NHCH₂CH₂CO₂Rᵃ, —NHCH₂CH₂ORᵃ, —NRᵃCH₂CH₂NA¹A², —OC₍₁₋₄₎alkylNA¹A², —OCH₂CO₂Rᵃ, —CH₂CO₂Rᵃ, —CH₂CH₂SO₂C₍₁₋₄₎alkyl, —SO₂CH₂CH₂NA¹A², —SOCH₂CH₂NA¹A², —SCH₂CH₂NA¹A², —NHSO₂CH₂CH₂NA¹A², or phenyl;
R^z and R^y are independently H or —C₍₁₋₄₎alkyl, wherein both R^z may have either syn or anti stereochemistry; alternatively both R^z in a syn relationship may be taken together to form —(CH₂)ₙ—, where n is 2 or 3;
R³ is H, C₍₁₋₄₎alkyl, C₍₁₋₃₎alkyl-CF₃, CH₂CH₂NH₂, CH₂CH₂ORᵃ, —COCH₃, CONH₂, or CO₂Rᵃ;
A¹ is H, —C₍₁₋₄₎alkyl, or CH₂CH₂ORᵃ; and
A² is H, —C₍₁₋₄₎alkyl, CORᵃ, CH₂CON(CH₃)₂, —CH₂CH₂ORᵃ, —CH₂CH₂SC₍₁₋₄₎alkyl, —CH₂CH₂SOC₍₁₋₄₎alkyl, or —CH₂CH₂SO₂C₍₁₋₄₎alkyl;
wherein Rᵃ is H or C₍₁₋₄₎alkyl;
A² is H, —CH₂CH₂OCH₃, —COCH₃, or —CH₃;
Rᵃ is H, or —C₍₁₋₄₎alkyl;
R^y is H, or —CH₃;
R^z is H, —CH₃, or may be taken together as —CH₂CH₂—;
R³ is H, —CH₂CF₃, —COCH₃, —CH₃, —CO₂CH₃, —CONH₂, or —CO₂H;
or a tautomer or pharmaceutically acceptable salt thereof.

3. The compound of claim 2 wherein
R² is

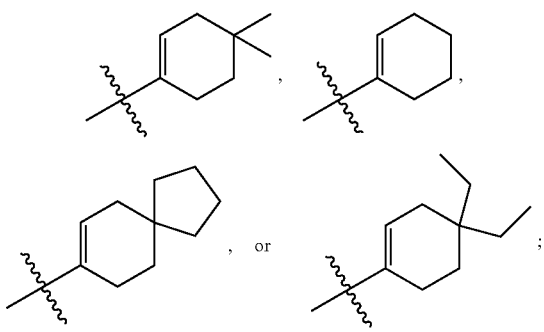

X is

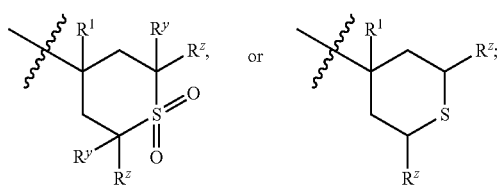

wherein R¹ is —OH, —CN, —NA¹A², —SO₂CH₃, —COOH, —CO₂CH₃, —CH₂—NA¹A², —CONH₂, —CON(CH₃)₂, —CH₂OH, —OCH₂CH₂N(CH₃)₂, —NHCH₂CH₂CO₂CH₃, —NHCH₂CH₂OCH₃, —NHCH₂CH₂NA¹A², —OC$_{(1-4)}$alkylNA¹A², or —OCH₂CO₂H;
A¹ is H, or —CH₃;
A² is H, —CH₂CH₂OCH₃, —COCH₃, or —CH₃;
R$^y$ is H, or —CH₃;
R$^z$ is H, —CH₃, or may be taken together as —CH₂CH₂—;
R³ is H, —CH₂CF₃, —COCH₃, —CH₃, —CO₂CH₃, —CONH₂, or —CO₂H;
or a tautomer or pharmaceutically acceptable salt thereof.

4. The compound of claim 3 wherein
W is

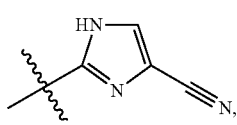 [SMILES: *c1nc(C#N)c[nH]1]

R² is

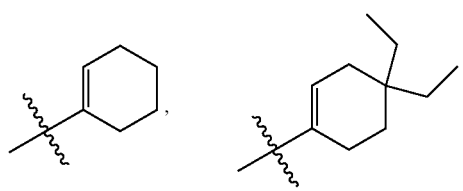

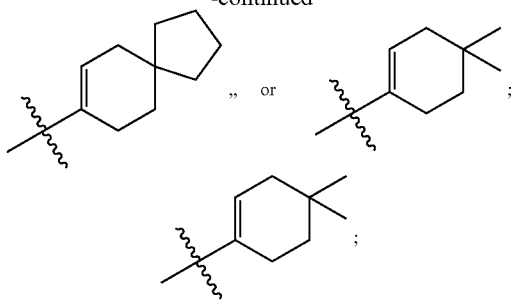

or a tautomer or pharmaceutically acceptable salt thereof.

5. The compound of claim 4 wherein
W is

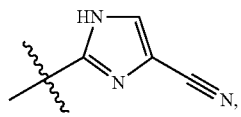 [SMILES: *c1nc(C#N)c[nH]1]

R² is

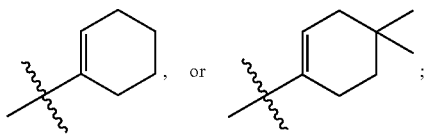

X is

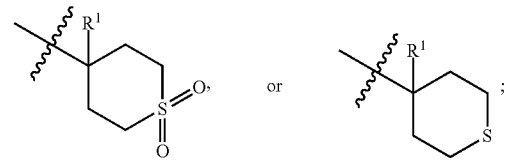

wherein R¹ is —OH, —NH₂, —N(CH₃)₂, —SO₂CH₃, —COOH, —CO₂CH₃, —CONH₂, —CON(CH₃)₂, —CH₂OH, —OCH₂CH₂N(CH₃)₂, —NHCH₂CH₂OCH₃, or —OCH₂CO₂H;
R$^z$ is H, or —CH₃;
R³ is —COCH₃, —CH₂CF₃, or —CO₂H;
or a tautomer or pharmaceutically acceptable salt thereof.

6. The compound selected from the group consisting of:

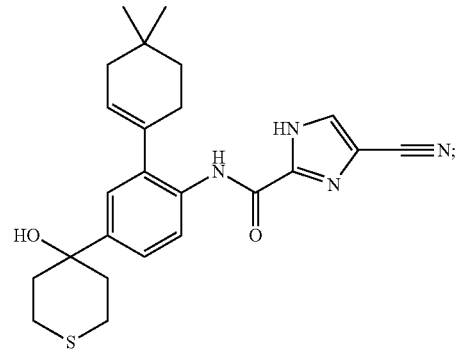

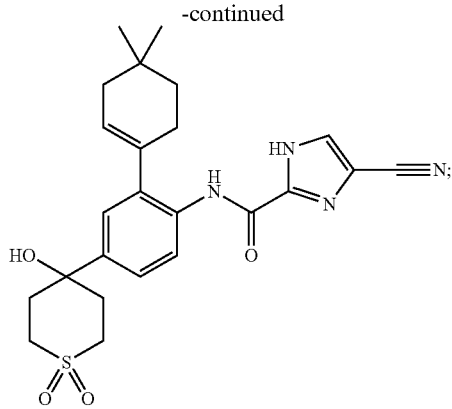

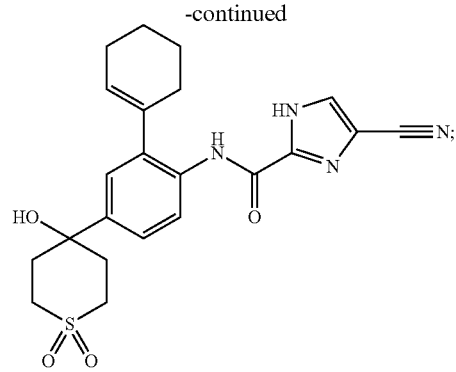

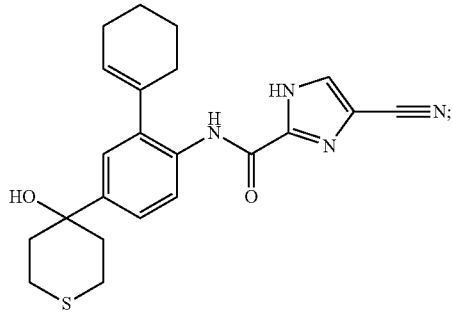

or a tautomer or pharmaceutically acceptable salt thereof.

7. A pharmaceutical composition, comprising a compound of claim 1 and a pharmaceutically acceptable carrier.

8. A pharmaceutical dosage form comprising a pharmaceutically acceptable carrier and from about 0.5 mg to about 10 g of at least one compound of claim 1.

9. A dosage form according to claim 8 adapted for parenteral or oral administration.

* * * * *